US008816047B2

(12) United States Patent
Levetan et al.

(10) Patent No.: US 8,816,047 B2
(45) Date of Patent: Aug. 26, 2014

(54) COMPOSITIONS AND METHODS OF USING PROISLET PEPTIDES AND ANALOGS THEREOF

(75) Inventors: Claresa S. Levetan, Rosemont, PA (US); Victor M. Garsky, Blue Bell, PA (US); Loraine V. Upham, Albuquerque, NM (US)

(73) Assignee: Cure DM Group Holdings, LLC, Wynnewood, PA (US)

( * ) Notice: Subject to any disclaimer, the term of this patent is extended or adjusted under 35 U.S.C. 154(b) by 946 days.

(21) Appl. No.: 12/674,573

(22) PCT Filed: Aug. 29, 2008

(86) PCT No.: PCT/US2008/074868
§ 371 (c)(1),
(2), (4) Date: Feb. 28, 2011

(87) PCT Pub. No.: WO2009/029847
PCT Pub. Date: Mar. 5, 2009

(65) Prior Publication Data
US 2011/0171178 A1 Jul. 14, 2011

Related U.S. Application Data

(60) Provisional application No. 60/969,019, filed on Aug. 30, 2007, provisional application No. 60/979,526, filed on Oct. 12, 2007, provisional application No. 60/991,964, filed on Dec. 3, 2007, provisional application No. 61/031,479, filed on Feb. 26, 2008.

(51) Int. Cl.
A61K 38/04 (2006.01)
A61K 38/00 (2006.01)

(52) U.S. Cl.
USPC .......................................... 530/327; 514/1.1

(58) Field of Classification Search
CPC ............................... A61K 38/04; A61K 38/00
See application file for complete search history.

(56) References Cited

U.S. PATENT DOCUMENTS

| | | | |
|---|---|---|---|
| 4,444,887 A | 4/1984 | Hoffmann | |
| 4,716,111 A | 12/1987 | Osband et al. | |
| 4,757,060 A | 7/1988 | Lukacsko et al. | |
| 4,816,397 A | 3/1989 | Boss et al. | |
| 4,816,567 A | 3/1989 | Cabilly et al. | |
| 5,028,535 A | 7/1991 | Buechler et al. | |
| 5,223,409 A | 6/1993 | Ladner et al. | |
| 5,225,539 A | 7/1993 | Winter | |
| 5,403,484 A | 4/1995 | Ladner et al. | |
| 5,427,908 A | 6/1995 | Dower et al. | |
| 5,436,169 A | 7/1995 | Iovanna et al. | |
| 5,516,637 A | 5/1996 | Huang et al. | |
| 5,530,101 A | 6/1996 | Queen et al. | |
| 5,565,332 A | 10/1996 | Hoogenboom et al. | |
| 5,571,698 A | 11/1996 | Ladner et al. | |
| 5,580,717 A | 12/1996 | Dower et al. | |
| 5,580,859 A | 12/1996 | Felgner et al. | |
| 5,585,089 A | 12/1996 | Queen et al. | |
| 5,631,224 A | 5/1997 | Efendic et al. | |
| 5,658,727 A | 8/1997 | Barbas et al. | |
| 5,698,426 A | 12/1997 | Huse | |
| 5,733,743 A | 3/1998 | Johnson et al. | |
| 5,750,753 A | 5/1998 | Kimae et al. | |
| 5,766,886 A | 6/1998 | Studnicka et al. | |
| 5,780,225 A | 7/1998 | Wigler et al. | |
| 5,807,715 A | 9/1998 | Morrison et al. | |
| 5,821,047 A | 10/1998 | Garrard et al. | |
| 5,834,590 A * | 11/1998 | Vinik et al. | 530/350 |
| 5,840,531 A | 11/1998 | Vinik et al. | |
| 5,959,086 A | 9/1999 | Iovanna et al. | |
| 5,969,108 A | 10/1999 | McCafferty et al. | |
| 6,311,415 B1 | 11/2001 | Lind | |
| 6,407,213 B1 | 6/2002 | Carter et al. | |
| 6,645,934 B1 | 11/2003 | Rodemann et al. | |
| 6,946,151 B2 | 9/2005 | Chatterji | |
| RE39,062 E | 4/2006 | Vinik et al. | |
| RE39,299 E | 9/2006 | Vinik et al. | |
| 7,166,439 B2 | 1/2007 | Vinik et al. | |
| 7,393,919 B2 * | 7/2008 | Levetan et al. | 530/327 |
| 7,576,121 B2 | 8/2009 | Campbell et al. | |
| 7,714,103 B2 * | 5/2010 | Levetan et al. | 530/326 |
| 7,989,415 B2 * | 8/2011 | Levetan et al. | 514/1.1 |
| 2003/0035803 A1 | 2/2003 | McMichael | |
| 2003/0212000 A1* | 11/2003 | Van Antwerp | 514/12 |
| 2004/0132644 A1 | 7/2004 | Vinik et al. | |

(Continued)

FOREIGN PATENT DOCUMENTS

| | | | |
|---|---|---|---|
| EP | 0303233 | A2 | 2/1989 |
| EP | 239400 | B1 | 8/1994 |

(Continued)

OTHER PUBLICATIONS

Reed et al. A new rat model of type 2 diabetes: the fat-fed, streptozotocin-treated rat. Metabolism. Nov. 2000;49(11):1390-4 (abstract). http://www.ncbi.nlm.nih.gov/pubmed/11092499 Source Shaman Pharmaceuticals, South San Francisco, CA 94080-4812, USA.*

Gannon et al., Development 127(3): 2883-2895 (2000); Yamagata et al., Diabetes 51(1): 114-123 (2002); and Zulewski et al., Diabetes 50(3): 521-533 (2001) (cited in para 80, present specification).*

Agardh, et al., Clinical evidence for the safety of GAD65 immunomodulation in adult-onset autoimmune diabetes, *J. Diabetes Complications* (2005) 19(4):238-246.

Ames, et al., Conversion of murine Fabs isolated from a combinatorial phage display library to full length immunoglobulins, *J. Immunol. Methods* (1995) 184:177-186.

Andersen, et al., Oral Glucose Augmentation of Insulin Secretion, *J. Clin. Invest.* (1978) 62:152-161.

(Continued)

Primary Examiner — Maury Audet
(74) Attorney, Agent, or Firm — Pepper Hamilton LLP

(57) ABSTRACT

Embodiments relate to proislet peptides, preferably HIP, that exhibit increased stability and efficacy, and methods of using the same to treating a pathology associated with impaired pancreatic function, including type 1 and type 2 diabetes and symptoms thereof.

19 Claims, 27 Drawing Sheets

(56) References Cited

U.S. PATENT DOCUMENTS

| | | | |
|---|---|---|---|
| 2005/0084449 | A1 | 4/2005 | Landes et al. |
| 2005/0249806 | A1 | 11/2005 | Proehl et al. |
| 2006/0198839 | A1 | 9/2006 | Levetan |
| 2007/0087971 | A1 | 4/2007 | Levetan et al. |
| 2007/0184504 | A1 | 8/2007 | Vinik et al. |
| 2008/0300190 | A1 | 12/2008 | Levetan et al. |
| 2009/0068145 | A1* | 3/2009 | Levetan et al. ............. 424/85.7 |
| 2009/0142338 | A1* | 6/2009 | Levetan ................. 424/133.1 |
| 2010/0093605 | A1 | 4/2010 | Levetan et al. |
| 2011/0082080 | A1* | 4/2011 | Levetan ................... 514/7.3 |
| 2011/0171178 | A1* | 7/2011 | Levetan et al. ............. 424/85.7 |
| 2011/0280833 | A1 | 11/2011 | Levetan et al. |

FOREIGN PATENT DOCUMENTS

| | | | |
|---|---|---|---|
| EP | 1329458 | A2 | 12/2000 |
| EP | 592106 | B1 | 11/2004 |
| EP | 519596 | B1 | 2/2005 |
| EP | 2559700 | A2 | 2/2013 |
| EP | 2570431 | A2 | 3/2013 |
| WO | WO 90/02809 | A1 | 3/1990 |
| WO | WO 91/09967 | A1 | 7/1991 |
| WO | WO 91/10737 | A1 | 7/1991 |
| WO | WO 91/10741 | A1 | 7/1991 |
| WO | WO 91/16428 | A1 | 10/1991 |
| WO | WO 92/01047 | A1 | 1/1992 |
| WO | WO 92/18619 | A1 | 10/1992 |
| WO | WO 92/22324 | A1 | 12/1992 |
| WO | WO 93/11236 | A1 | 6/1993 |
| WO | WO 93/17105 | A1 | 9/1993 |
| WO | WO 95/15982 | A2 | 6/1995 |
| WO | WO 95/20401 | A1 | 8/1995 |
| WO | WO 96/19236 | A1 | 6/1996 |
| WO | WO 96/26215 | A1 | 8/1996 |
| WO | WO 96/33735 | A1 | 10/1996 |
| WO | WO 96/34096 | A1 | 10/1996 |
| WO | WO 97/13844 | A1 | 4/1997 |
| WO | WO 98/16654 | A1 | 4/1998 |
| WO | WO 98/24893 | A2 | 6/1998 |
| WO | WO 98/46645 | A2 | 10/1998 |
| WO | WO 98/50433 | A2 | 11/1998 |
| WO | WO 03/033808 | A2 | 4/2003 |
| WO | WO 03/074549 | A2 | 9/2003 |
| WO | WO 03/105897 | A1 | 12/2003 |
| WO | WO 2005/035761 | A1 | 4/2005 |
| WO | WO 2006/059106 | A2 | 6/2006 |
| WO | WO 2006/096565 | A2 | 9/2006 |
| WO | WO 2006/128082 | A2 | 11/2006 |
| WO | WO 2006/128083 | A2 | 11/2006 |
| WO | WO 2007/102526 | A1 | 9/2007 |

OTHER PUBLICATIONS

Atherton, et al., Solid Phase Peptide Synthesis: A Practical Approach, *IRL Press*, Oxford (1989) (TOC).

Ausubel, et al., Current Protocols in Molecular Biology, vol. 1, John Wiley & Sons (2008) (TOC).

Ausubel, et al., Short Protocols in Molecular Biology, Current Protocols in Molecular Biology, 2nd ed., John Wiley & Sons (1992) (TOC).

Baca, et al., Antibody Humanization Using Monovalent Phage Display, *J. Biol. Chem.* (1997) 272(16):10678-10684.

Bach, et al., Tolerance to Islet Autoantigens in Type 1 Diabetes, *Ann. Rev. Immun.* (2001) 19:131-161.

Better, et al., *Escherichia coli* Secretion of an Active Chimeric Antibody Fragment, *Science* (1988) 240:1041-1043.

Bitter, et al., Expression and Secretion Vectors for Yeast, *Methods in Enzymol.* (1987) 153:516-544.

Bodanszky Peptide Chemistry, A Practical Textbook, 2nd ed., Springer-Verlag, Berlin (1993) (TOC).

Bonner-Weir, et al., The pancreatic ductal epithelium serves as a potential pool of progenitor cells, *Pediatric Diabetes* (2004) 5 (Suppl 2):16-22.

Brinkmann, et al., Phage display of disulfide-stabilized Fv fragments, *J. Immunol. Methods* (1995) 182:41-50.

Burton, et al., Human Antibodies from Combinatorial Libraries, *Advances in Immunology* (1994) 57:191-280.

Buse, et al., Amylin replacement with pramlinlide in type 1 and type 2 diabetes: A physiological approach to overcome barriers with insulin therapy, *Clin. Diab.* (2002) 20:137-144.

Caldas, et al., Design and synthesis of germline-based hemi-humanized single-chain Fv against the CD18 surface antigen, *Protein Eng.* (2000) 13(5):353-360.

Casteels, et al., Prevention of Type I Diabetes in Nonobese Diabetic Mice by Late Intervention with Nonhypercalcemic Analogs of 1,25-Dihydroxyvitamin D3 in Combination with a Short Induction Course of Cyclosporin A, *Endocrionology* (1998) 139(1):95-102.

Cockett, et al., High Level Expression of Tissue Inhibitor of Metalloproteinases in Chinese Hamster Ovary Cells Using Glutamine Synthetase Gene Amplification, *Bio/Technology* (1990) 8:662-667.

Colbere-Garapin, et al., A New Dominant Hybrid Selective Marker for Higher Eukaryotic Cells, *J. Mol. Biol.* (1981) 150:1-14.

Couto, et al., Anti-BA46 Monoclonal Antibody Mc3: Humanization Using a Novel Positional Consensus and in Vivo and in Vitro Characterization, *Cancer Res.* (1995,) 55(8):1717-1722.

Couto, et al., Designing Human Consensus Antibodies with Minimal Positional Templates, *Cancer Res.* (1995) 55(23 Suppl):5973s-5977s.

Creutzfeldt, The Incretin Concept Today, *Diabetologia* (1979) 16:75-85.

Creutzfeldt, et al., Inhibition of Gastric Inhibitory Polypeptide (GIP) Release by Insulin and Glucose in Juvenile Diabetes, *Diabetes* (1980) 29(2):140-145.

Creutzfeldt, et al., New developments in the incretin concept, *Diabetologia* (1985) 28:565-573.

Davis, et al., The effects of HDV-insulin on carbohydrate metabolism in Type 1 diabetic patients, *J. Diabetes Comp.* (2001) 15(5):227-233.

Delovitch, et al., The Nonobese Diabetic Mouse as a Model of Autoimmune Diabetes: Immune Dysregulation Gets the NOD, *Immunity* (1997) 7:727-738.

Dicesar, et al., Vitamin D Deficiency is More Common in Type 2 Than in Type 1 Diabetes, *Diabetes Care* (Jan. 2006) 29(1):174.

Dupre, et al., Exendin-4 Normalized Postcibal Glycemic Excursions in Type 1 Diabetes, *J. Clin. Endocrin. Metab.* (2004) 89(7):3469-3473.

Dupre, et al., Stimulation of Insulin Secretion by Gastric Inhibitory Polypeptide in Man, *J. Clin. Endocrin. Metab.* (1973) 37:826-828.

Ebert, et al., Gastric Inhibitory Polypeptide, *Clin. in Gastroenterology* (1980) 9(3):679-698.

Edwards, et al., Glucagon-Like Peptide 1 Has a Physiological Role in the Control of Postprandial Glucose in Humans, *Diabetes* (1999) 48:86-93.

Elahi, et al., Pancreatic α- and β-cell responses to GIP infusion in normal man, *Am. J. Physiol.* (1979) 237:E185-E191.

Elahi, et al., The insulinotropic actions of glucose-dependent insulinotropic polypeptide (IP) and glucagon-like peptide-1 (7-37) in normal and diabetic subjects, *Regulatory Peptide* (1994) 51(1):63-74.

Foecking, et al., Powerful and versatile enhancer-promoter unit for mammalian expression vectors, *Gene* (1986) 45:101-105.

Gillies, et al., High-level expression of chimeric antibodies using adapted cDNA variable region cassettes, *J. Immunol. Methods* (1989) 125:191-202.

Grant, Epidemiology of disease risks in relation to vitamin D insufficiency, *Prog. Biophys. Mol. Biol.* (Feb. 28, 2006) 92:65-79.

Gutniak, et al., Subcutaneous Injection of the Incretin Hormone Glucagon-Like Peptide 1 Abolishes Postprandial Glycemia in NIDDM, *Diabetes Care* (1994) 17(9):1039-1044.

Haines, et al., Ex Vivo and In Vivo Gene Delivery to the Brain, *Current Protocols in Human Genetics*, John Wiley & Sons, NY (1994) 4(13).

Haines, et al., Vectors for Gene Therapy, *Current Protocols in Human Genetics*, John Wiley & Sons, NY (1994) 3(12).

Hammerling, et al., Monoclonal Antibodies and T-Cell Hybridomas, *Perspectives and technical advances*, Elsevier, NY (1981) (TOC).

(56) References Cited

OTHER PUBLICATIONS

Hao, et al., Beta-cell differentiation from nonendocrine epithelial cells of the adult human pancreas, *Nature Medicine* (2006) 12(3):310-316.

Harlow, et al., Antibodies: A Laboratory Manual, Cold Spring Harbor Laboratory Press, 2nd ed. (1988) (TOC).

Heaney, et al., Human serum 25-hydroxycholecalciferol response to extended oral dosing with cholecalciferol[1-3], *Am. J. Clin. Nutr.* (2003) 77:204-210.

Herold, et al., A Single Course of Anti-CD3 Monoclonal Antibody hOKT3γ1 (Ala-Ala) Results in Improvement in C-Peptide Responses and Clinical Parameters for at Least 2 Years after Onset of Type 1 Diabetes, *Diabetes* (2005) 54(6):1763-1769.

Herold, et al., Anti-CD3 Monoclonal Antibody in New-Onset Type 1 Diabetes Melitus, *New Eng. J. Med.* (May 20, 2002) 346(22):1692-1698.

Holick, et al., Prevalence of Vitamin D Inadequacy among Postmenopausal North American Women Receiving Osteoporosis Therapy, *J. Clin. Endocrinol. Metab.* (2005) 90(6):3215-3224.

Holick, High Prevalence of Vitamin D Inadequacy and Implications for Health, *Mayo Clin. Proc.* (Mar. 2006) 81(3):353-373.

Holst, et al., Incretin hormones—an update, *Scand. J. Clin. Lab. Invest.* (2001) 61(Sup. 234):75-86.

Hopp, et al., Prediction of protein antigenic determinants from amino acid sequences, *PNAS USA* (1981) 78(6):3824-3828.

Ilic, et al., Is the paradoxical first trimester drop in insulin requirement due to an increase in C-peptide concentration in pregnant Type I diabetic women?, *Diabetologia* (2000) 43:1329-1330.

Inouye, et al., Up-promoter mutations in the *lpp* gene of *Escherichia coli*, *Nucleic Acids Res.* (1985) 13(9):3101-3109.

International Search Report and Written Opinion dated Dec. 23, 2008 (PCT/US2008/074868).

International Search Report and Written Opinion dated Feb. 26, 2007 (PCT/US2006/020644).

International Search Report and Written Opinion dated Aug. 22, 2008 (PCT/US2007/85378).

Jamal, et al., Morphogenetic Plasticity of Adult Human Pancreatic Islets of Langerhans, *Cell Death Differ.* (Apr. 8, 2005) 12:702-712.

Jones, et al., A supplementary infusion of glucose-dependent insulinotropic polypeptide (GIP) with a meal does not significantly improve the β cell response or glucose tolerance in type 2 diabetes mellitus, *Diabetes Res. Clin. Prect.* (Nov. 6, 1989) 7(4):263-269.

Jovanovic, et al., Declining Insulin Requirement in the Late First Trimester of Diabetic Pregnancy, *Diabetes Care* (2001) 24:1130-1136.

Kettleborough, et al., Isolation of tumor cell-specific single-chain Fv from immunized mice using phage-antibody libraries and the reconstruction of whole antibodies from these antibody fragments, *Eur. J. Immunol.* (1994) 24:952-958.

Krarup, et al., Diminished Immumoreactive Gastric Inhibitory Polypeptide Response to a Meal in Newly Diagnosed Type 1 (Insulin-Dependent) Diabetics, *J. Clin. Endocrin. Metab.* (Jun. 1983) 56(6):1306-1312.

Krarup, et al., Effect of Porcine Gastric Inhibitory Polypeptide on β-cell Function in Type I and Type II Diabetes Mellitus, *Metabolism* (1987) 36(7):677-682.

Krarup, et al., Gastric Inhibitory Polypeptide in Newly Diagnosed Ketotic Type 1 (Insulin-dependent) Diabetics, *Acta Med. Scand.* (1988) 223(5):437-441.

Kreymann, et al., Glucagon-Like Peptide-1 7-36: A Physiological Incretin in Man, *Lancet* (1987) 2:1300-1304.

Kriegler, Gene Transfer and Expression, *A Laboratory Manual*, Stockton Press, NY (1990) (TOC).

Larsen, et al., Glucagon-Like Peptide-1 Infusion Must be Maintained for 24 h/day to Obtain Acceptable Glycemia in Type 2 Diabetic Patients Who Are Poorly Controlled on Sulphonylurea Treatment, *Diabetes Care* (2001) 24(8):1416-1421.

Larsen, et al., One-Week Continuous Infusion of GLP-1(7-37) Improves the Glycaemic Control in NIDDM, Abstracts from 56th Ann. Meeting in San Francisco, CA, *Diabetes* (1996) 45(Suppl. 2):860:233A (Abstract).

Lernmark, et al., Autoimmunity of Diabetes, *Endocrinology and Metabolism Clinics of North America* (1991) 20(3):589-617.

Levetan, et al., Impact of Pramlintide on Glucose Fluctuations and Postprandial Glucose, Glucagon, and Triglyceride Excursions Among Patients with Type 1 Diabetes Intensively Treated with Insulin Pumps, *Diabetes Care* (2003) 26(1):1-8.

Levetan, et al., Impact of Pramlintide on the Amplitude of Glycemic Excursions, Abstracts from 61st Ann. Meeting in San Francisco, CA, *Diabetes* (2001) 50(Suppl. 2):2105-PO:A501 (Abstract).

Levetan, et al., Reduced Glucose Fluctuations Following 4 Weeks of Pramlintide Treatment in Patients with Type 1 Diabetes Intensively Treated with Insulin Pumps, Abstracts from 62nd Ann. Meeting in San Francisco, CA, *Diabetes* (2002) 51(Suppl. 2):429-P:A106 (Abstract).

Lewis, et al., Improved glucose control in nonhospitalized pregnant diabetic patients, *Obstet. & Gynecol.* (1976) 48(3):260-267.

Li, et al., Islet loss and alpha cell expansion in type 1 diabetes induced by multiple low-dose streptozotocin administration in mice, *J. Endocrinol.* (2000) 165:93-99.

List, et al., Glucagon-like peptide 1 agonists and the development and growth of pancreatic β-cells, *Am. J. Physiol. Endocrin. Metab.* (2004) 286(6): E875-E881.

Logan, et al., Adenovirus tripartite leader sequence enhances translation of mRNAs late after infection, *PNAS USA* (1984) 81:3655-3659.

Ludvigsson et al., GAD Treatment and Insulin Secretion in Recent-Onset Type 1 Diabetes, N Engl J Med (2008):359: 1-12.

Lugari, et al., Effect of Nutrient Ingestion on Glucagon-Like Peptide 1 (7-36 Amide) Secretion in Human Type 1 and Type 2 Diabetes, *Horm. Metab. Res.* (2000) 32:424-428.

Lynn, et al., A novel pathway for regulation of glucose-dependent insulinotropic polypeptide (GIP) receptor expression in β cells, *FASEB* (2003) 17:91-93.

Marquez, et al., Inositolphosphoglycans Possibly Mediate the Effects of Glucagon-Like Peptide-1 (7-36) amide on Rat Liver and Adipose Tissue, *Cell Biochem. Funct.* (1998) 16(1):51-56.

Mathis, et al., β-Cell death during progression to diabetes, *Nature* (Dec. 2001) 414(6865):792-798.

Meier, et al., Intravenous glucagon-like peptide 1 normalizes blood glucose after major surgery inpatients with type 2 diabetes, *Critical Care Medicine* (Mar. 2004) 32(3):848-851.

Meier, et al., Gastric Inhibitory Polypeptide: the neglected incretin revisited, *Regulatory Peptides* (2002) 107:1-13.

Meneilly, et al., Effects of 3 Months of Continuous Subcutaneous Administration of Glucagon-Like Peptide 1 in Elderly Patients with Type 2 Diabetes, *Diabetes Care* (2003) 26(10):2835-2841.

Merrifield, Solid Phase Peptide Synthesis, The Synthesis of a Tetrapeptide, *J. Am. Chem. Soc.* (1963) 85:2149-2154.

Morea, et al., Antibody Modeling: Implications for Engineering and Design, *Methods* (2000) 20(3):267-279.

Morgan, et al., Human Gene Therapy, *Ann. Rev. Biochem.* (1993) 62:191-217.

Morrison, Transfectomas Provide Novel Chimeric Antibodies, *Science* (1985) 229:1202-1207.

Mulligan, et al., Selection for animal cells that express the *Escherichin coli* gene coding for xanthine-guanine phosphoribosyltransferase, *PNAS USA* (1981) 78(4):2072-2076.

Mulligan, The Basic Science of Gene Therapy, *Science* (1993) 260:926-932.

Mullinax, et al., Expression of a Heterodimeric Fab Antibody Protein in One Cloning Step, *BioTechniques* (1992) 12(6):864-869.

Nauck, et al., Additive Insulinotropic Effects of Exogenous Synthetic Human Gastric Inhibitory Polypeptide and Glucagon-Like Peptide-1-(7-36) Amide Infused at Near-Physiological Insulinotropic Hormone and Glucose Concentrations, *J. Clin. Endocrin. Metab.* (1993) 76(4):912-917.

Nauck, et al., Effects of subcutaneous glucagon-like peptide 1 (GLP-1 [7-36 amide]) in patients with NIDDM, *Diabetologia* (1996) 39(12):1546-1553.

(56) References Cited

OTHER PUBLICATIONS

Ogawa, et al., Cure of Overt Diabetes in NOD Mice by Transient Treatment with Anti-Lymphocyte Serum and Exendin-4, *Diabetes* (2004) 53(7):1700-1705.

Ohare, et al., Transformation of mouse fibroblasts to methotrexate resistance by a recombinant plasmid expressing a prokaryotic dihydrofolate reductase, *PNAS USA* (1981) 78(3):1527-1531.

Oi, et al., Chimeric Antibodies, *Bio Techniques* (1986) 4(3):214-222.

Padlan, A Possible Procedure for Reducing the Immunogenicity of Antibody Variable Domains While Preserving Their Ligand-Binding Properties, *Molecular Immunology* (1991) 28(4/5):489-498.

Pederson, et al., Comparison of Surface Accessible Residues in Human and Murine Immunoglobulin Fv Domains, *J. Mol. Biol.* (1994) 235(3):959-973.

Persic, et al., An integrated vector system for the eukaryotic expression of antibodies or their fragments after selection from phage display libraries, *Gene* (1997) 187:9-18.

Pozzilli, et al., Low Levels of 25-hydroxyvitamin $D^3$ and 1,25-dihydroxyvitamin D3 in Patients with Newly Diagnosed Type 1 Diabetes, *Horm. Metab. Res.* (2005) 37(11):680-683.

Rabinovitch, et al., Combination Therapy With Sirolimus and Interleukin-2 Prevents Spontaneous and Recurrent Autoimmune Diabetes in NOD Mice, *Diabetes* (2002) 51:638-645.

Rafaeloff, et al., Cloning and Sequencing of the Pancreatic Islet Neogenesis Associated Protein (INGAP) Gene and Its Expression in Islet Neogenesis in Hamsters, *J. Clin. Invest.* (May 1997) 99(9):2100-2109.

Raz, et al., β-cell function in new-onset type 1 diabetes and immunomodulation with a heat-shock protein peptide (DiaPep277): a randomized, double-blind, phase II trial, *Lancet* (Nov. 2001) 358(9295):1749-1753.

Reis, et al., Vitamin D endocrine system and the genetic susceptibility to diabetes, obesity and vascular disease, A review of evidence, *Diabetes Metab.* (2005) 31:318-325.

Riachy, et al., 1,25-dihydroxyvitamin D3 protects human pancreatic islets against cytokine-induced apoptosis via down-regulation of the fas receptor, *Apoptosis* (Feb. 2006) 11(2):151-159.

Riechmann, et al., Reshaping human antibodies for therapy, *Nature* (1988) 332:323:327.

Rigg, et al., Effects of Exogenous insulin on excursions and diurnal rhythm of plasma glucose in pregnant diabetic patients with and without residual, *Am. J. Obstet. Gynecol.* (1980) 136:537-544.

Roguska, et al., A Comparison of two murine monoclonal antibodies humanized by CDR-grafting and variable domain resurfacing, *Protein Eng.* (Oct. 1996) (10):895-904.

Roguska, et al., Humanization of murine monoclonal antibodies through variable domain resurfacing, *PNAS* (1994) 91:969-973.

Rosenberg, et al., A Pentadecapeptide Fragment of Islet Neogenesis-Associated Protein Increases Beta-Cell Mass and Reverses Diabetes in C57BL/6J Mice, *Ann. Surg.* (2004) 240(5):875-884.

Rosenberg, et al., Induction of Islet Cell Differentiation and New Islet Formation in the Hamster-Further Support for a Ductular Origin, *Pancreas* (Jul. 1996) 13(1):38-46.

Rosenberg, et al., Islet-cell regeneration in the diabetic hamster pancreas with restoration of normoglycaemia can be induced by a local growth factor(s), *Diabetologia* (1996) 39(3):256-262.

Rosenberg, et al., Trophic Stimulation of the Ductular-Islet Cell Axis: A New Approach to the Treatment of Diabetes, *Adv. Exp. Med. Biol.* (1992) 321:95-104.

Sandhu, A rapid procedure for the humanization of monoclonal antibodies, *Gene* (1994) 150(2):409-410.

Santerre, et al., Expression of prokaryotic genes for hygromycin B and G418 resistance as dominant-selection markers in mouse L cells, *Gene* (1984) 30:147-156.

Sawai, et al., Direct Production of the Fab Fragment Derived from the Sperm Immobilizing Antibody Using Polymerase Chain Reaction and cDNA Expression Vectors, *AJRI* (1995) 34:26-34.

Scopes, Protein Purification, *Principles and Practice*, 3rd ed., Springer, NY (1994) (TOC).

Studnicka, et al., Human-engineered monoclonal antibodies retain full specific binding activity by preserving non-CDR complementarity-modulating residues, *Protein Engineering* (1994) 7(6):805-814.

Tam, et al., INGAP Peptide improves nerve function and enhances regeneration in streptozotocin-induced diabetic C57BL/6 mice, *FASEB J.* (Sep. 2, 2004) 18(4):1-23.

Tan, et al., 'Superhumanized' Antibodies: Reduction of Immunogenic Potential by Complementarity-Determining Region Grafting with Human Germline Sequences: Application to an Anti-CD28, *J. Immunol.* (2002) 169:1119-1125.

Thorens, et al., Glucagon-Like Peptide-1 and Control of Insulin Secretion, *Diabetes Metab.* (1995) 21(5):311-318.

Tolstoshev, Gene Therapy, Concepts, Current Trials and Future Directions, *Ann. Rev. Pharmacol. Toxicol.* (1993) 32:573-596.

Van Heeke, et al., Expression of Human Asparagine Synthetase in *Escherichia coli*, *J. Biol. Chem.* (1989) 264(10):5503-5509.

Vieth, et al., Efficacy and safety of vitamin D3 intake exceeding the lowest observed adverse effect level 1-3, *Am. J. Clin. Nutr.* (2001) 73:288-294.

Vilsboll, et al., Incretin Secretion in Relation to Meal Size and Body Weight in Healthy Subjects and People with Type 1 and Type 2 Diabetes Mellitus, *J. Clin. Endocrin. Metab.* (2003) 88(6):2706-2713.

Vinik, et al., Induction of Pancreatic Islet Neogenesis, *Horm. Metab. Res.* (Jun. 1997) 29(7):278-293.

Vukkadapu, et al., Dynamic interaction between T cell-mediated β-cell damage and β-cell repair in the run up to autoimmune diabetes of the NOD mouse, *Physiol. Genomics* (2005) 21(2):201-211.

Wang, et al., Glucagon-like peptide-1 Can Reverse the Age-related Decline in Glucose Tolerance in Rats, *J. Clin. Invest.* (Jun. 1997) 99(12):2883-2889.

Want, et al., Reduced Postprandial Glucose, Glucagon and Triglyceride Excursions Following 4 Weeks of Pramlintide Treatment in Patients with Type 1 Diabetes Treated Intensively with Insulin Pumps, *Diabetes* (Jun. 14, 2002) 51(suppl. 2):474-P.

Wigler, et al., Transformation of mammalian cells with an amplifiable dominant-acting gene, *Proc. Natl. Acad. Sci. USA* (Jun. 1980) 77(6):3567-3570.

Wu, et al., Adapters, Linkers and Methylation, *Methods in Enzymol.* (1987) 152:343-349.

Wu, et al., Delivery systems for gene therapy, *Biotherapy* (1991) 3(1):87-95.

Xu, et al., Exendin-4 Stimulates Both β-Cell Replication and Neogenesis, Resulting in Increased β-Cell Mass and Improved Glucose Tolerance in Diabetic Rats, *Diabetes* (Dec. 1999) 48:2270-2276.

Yoon, et al., Selective β-Cell Loss and α-Cell Expansion in Patients with Type 2 Diabetes Mellitus in Korea, *J. Clin. Endocrinol. Metab.* (May 2003) 88(5):2300-2308.

Young, et al., Amylin's physiology and its role in diabetes, *Curr. Opin. Endocrin. Diabetes* (1997) 4(4):282-290.

Zander, et al., Effect of 6-week course of glucagon-like peptide 1 on glycaemic control, insulin sensitivity, and β-cell function in type 2 diabetes: a parallel-group study, *Lancet* (Mar. 2002) 359:824-830.

Bach, et al., Tolerance to Islet Autoantigens in Type 1 Diabetes, *Ann. Rev. Immun.* (Apr. 2001) 19:131-161.

Haines, et al., Ex Vivo and In Vivo Gene Delivery to the Brain, *Current Protocols in Human Genetics*, John Wiley & Sons, NY (Apr. 1994) 4(13).

Haines, et al., Vectors for Gene Therapy, *Current Protocols in Human Genetics*, John Wiley & Sons, NY (Apr. 1994) 3(12).

Heaney, et al., Human serum 25-hydroxycholecalciferol response to extended oral dosing with cholecalciferol1-3, *Am. J. Clin. Nutr.* (Jan. 2003) 77(1):204-210.

International Search Report and Written Opinion dated Dec. 23, 2008.

International Search Report and Written Opinion dated Feb. 26, 2007.

International Search Report and Written Opinion dated Aug. 22, 2008.

Lernmark, et al., Autoimmunity of Diabetes, *Endocrinology and Metabolism Clinics of North America* (Sep. 1991) 20(3):589-617.

(56) References Cited

OTHER PUBLICATIONS

Levetan, et al., Impact of Pramlintide on Glucose Fluctuations and Postprandial Glucose, Glucagon, and Triglyceride Excursions Among Patients with Type 1 Diabetes Intensively Treated with Insulin Pumps, *Diabetes Care* (Jan. 2003) 26(1):1-8.

Levetan, et al., Impact of Pramlintide on the Amplitude of Glycemic Excursions, *Abstracts from 61st Ann. Meeting in San Francisco, CA, Diabetes* (Jun. 22-26, 2001) 50(Suppl. 2):2105-PO:A501 (Abstract).

Levetan, et al., Reduced Glucose Fluctuations Following 4 Weeks of Pramlintide Treatment in Patients with Type 1 Diabetes Intensively Treated with Insulin Pumps, *Abstracts from 62nd Ann. Meeting in San Francisco, CA, Diabetes* (Jun. 14-18, 2002) 51(Suppl. 2):429-P:A106 (Abstract).

Biron et al., A Monomeric 310-Helix is Formed in Water by a 13-Residue Peptide Representing the Neutralizing Determinant of HIV-1 on gp41, *Biochemistry* (2002) 41(42):12687-12696.

Levetan, et al., Reduced Postprandial Glucose, Glueagon and Triglyceride Excursions Following 4 Weeks of Pramlintide Treatment in Patients with Type 1 Diabetes Treated Intensively with Insulin Pumps, *Abstracts from 62nd Ann. Meeting in San Francisco, CA, Diabetes* (Jun. 2002) 51(Suppl. 2):474-P:A117 (Abstract).

Mishra, et al., Studies of Synthetic Peptides of Human Apolipoprotein A-I Containing Tandem Amphipathic α-Helixes, *Biochemistry* (1998) 37(28):10313-10324.

Levetan et al. "Discovery of a Human Peptide Sequence Signaling Islet Neogenesis" Dec. 2008, *Endocrine Practice* 14(9):1075-1083.

Yang et al. "Lisofylline: a Potential Lead for the Treatment of Diabetes" Jan. 1, 2005, *Biochemical Pharmacology* 69(1):1-5.

Igarashi, et al. Role of GLP-1, *Internal Secretion/Diabetes Department*, Jan. 28, 2005, vol. 20, No. 1, p. 69-74.

Ronit et al., Closing and Sequencing of the Pancreatic Islet Neogenesis Associated Protein (INGAP) Gene and Its Expression in Islet Neogenesis in Hamsters, *J. CLin. Invest.* (May 1997) 99(9):2100-2109.

Yamaoka, Regeneration therapy for diabetes mellitus, *Expert Opin. Biol. Ther* (2003) 3(3):425-433.

Dusetti et al. "Molecular Cloning, Genomic Organization, and Chromosomal Localization of the Human Pancreatitis-Associated Protein (PAP) Gene" 1994, *Genomics* 19:108-114.

Andersen, et al. "Latent Autoimmune Diabetes in Adults Differs Genetically from Classical Type 1 Diabetes Diagnosed After the Age of 35 Years" 2010, *Diabetes Care* 33(9):2062-2064.

Butler, et al. "β-Cell Deficit and Increased β-Cell Apoptosis in Humans With Type 2 Diabetes" 2003, *Diabetes* 52(1):102-110.

Delprato et al. "Beta- and Alpha-cell Dysfunction in Type 2 Diabetes" 2004, *Horm. Metab. Res.* 36(11-12):775-781.

Fineberg, et al. "Antibody Response to Inhaled Insulin in Patients with Type 1 or Type 2 Diabetes: An Analysis of Initial Phase II and III Inhaled Insulin (Exubera) Trials and a Two-Year Extension Trial" 2005, *The Journal of Clin. Endrocrin. Metab.* 90(6):3287-3294.

Kapur, et al. "Short-Term Effects of INGAP and Reg Family Peptides on the Appearance of Small β-Cells Clusters in Non-Diabetic Mice" 2012, *Islets* 4(1):40-48.

Palmer, et al. "Is Latent Autoimmune Diabetes in Adults Distinct from Type 1 Diabetes or Just Type 1 Diabetes at an Older Age" 2005, *Diabetes* 54(Supp 2):S62-S67.

Palmer, et al. "What's in a Name Latent Autoimmune Diabetes of Adults, Type1.5, Adult-Onset, and Type 1 Diabetes" 2003, *Diabetes Care* 26(2):536-538.

Sigal et al. "Physical Activity/Exercise and Type 2 Diabetes" 2004, *Diabetes Care* 27(10):2518-2539.

dePril et al., Ubiquitin-Conjugating Enzyme E2-25K Increases Aggregate Formation and Cell Death in Polyglutamine Diseases, *Mol. Cell. Neuroscience* (Jan. 2007) 34(1):10-19.

European Search Report and Written Opinion dated Jan. 29, 2013 for EP12183674.

European Search Report and Written Opinion dated Mar. 21, 2013 for EP 12183685.

Rosenberg et al., Pancreatic and Islet Transplantation, *Current Gastroenterology Reports* (2000) 2:165-172.

Wang et al., YAC/BAC-Based Physical and Transcript Mapping Around the Gracile Axonal Dystrophy (gad) Locus Identifies Uchl1, Pmx2b, Atp3a2, and Hip2 Genes, *Genomics* (2000) 66:333-336.

\* cited by examiner

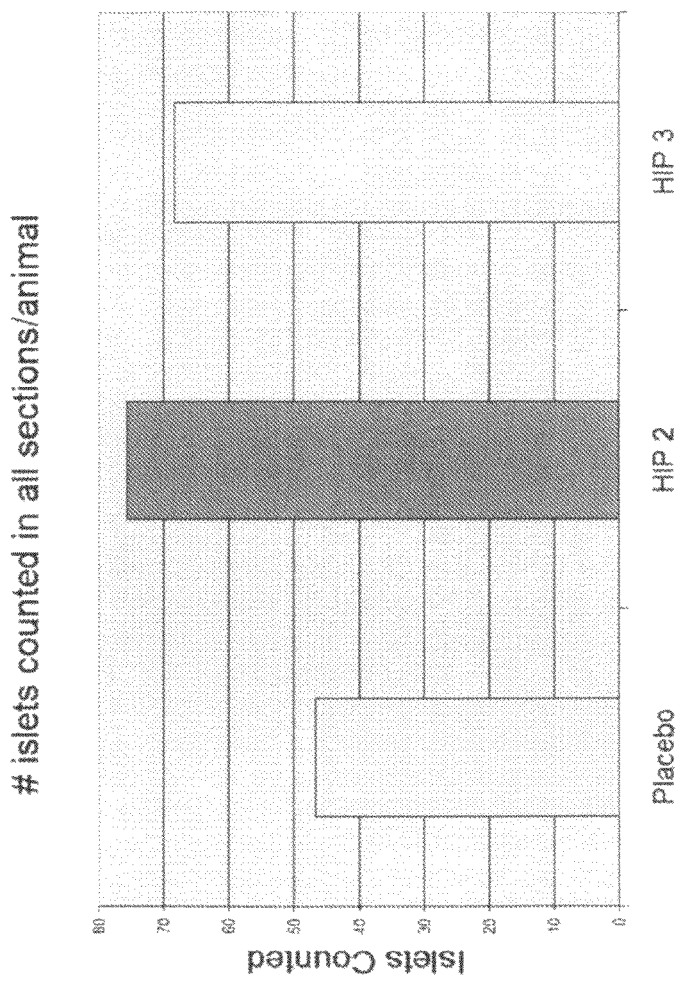

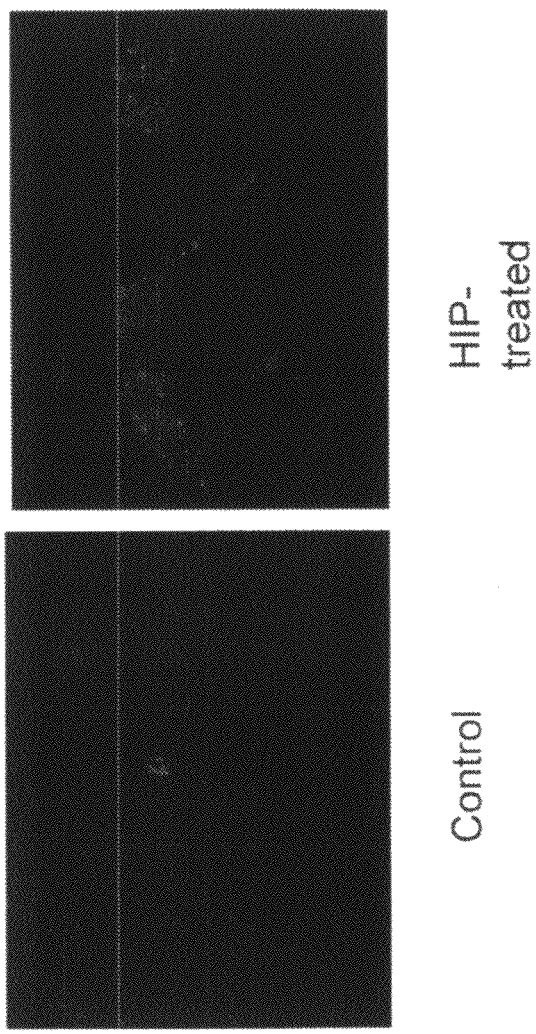

COMPOSITIONS AND METHODS OF USING PROISLET PEPTIDES AND ANALOGS THEREOF

CROSS-REFERENCE TO RELATED APPLICATIONS

This application is a U.S. national stage filing under 35 U.S.C. §371 of PCT Application PCT/US2008/074868 filed Aug. 29, 2008, which claims priority to U.S. Provisional Application No. 60/969,019 filed Aug. 30, 2007, U.S. Provisional Application No. 60/979,526 filed Oct. 12, 2007, U.S. Provisional Application No. 60/991,964 filed Dec. 3, 2007 and U.S. Provisional Application No. 61/031,479 filed Feb. 26, 2008. All aforementioned applications are herein incorporated by reference in their entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Not applicable
1. Field
Not applicable
2. Description of Related Art
Not applicable

BRIEF SUMMARY

Embodiments disclosed herein provide formulations, derivatives and modifications of proislet peptides designed to increase their solubility, bioavailability and in-serum-resistance to protease cleavage thereby improving their effectiveness as a therapeutic agent and methods of using the same.

In one embodiment, proislet peptides and derivatives thereof are blocked with a N-terminal acetyl group and a C-terminal amide group.

In one embodiment, HIP and derivatives thereof are blocked with a N-terminal acetyl group and a C-terminal amide group (HIP3Blocked (SEQ ID NO: 5), HIP1Blocked (SEQ ID NO: 6) and HIP2Blocked (SEQ ID NO:7)). Such modifications appear to render the sequence less susceptible to protease cleavage in serum with those proteases that normally recognize free ends, thereby effectively increasing the Tmax and bioavailability of the peptide. Peptides modified in this manner demonstrate increased efficacy thereby requiring decreased dosages when administered by for example, IV, IM, SubQ or intraperitoneal routes.

In another embodiment, proislet peptides and derivatives thereof are modified by adding a cysteine residue to the N-terminal of the peptide.

In another embodiment, HIP and derivatives thereof are modified by adding a cysteine residue to the C-terminal of HIP (HIP3Cys (SEQ ID NO: 8), HIP1Cys (SEQ ID NO: 9) and HIP2Cys (SEQ ID NO: 10)); resulting in a compound which is capable of forming dimers in solution (HIP3CysDimer (SEQ ID NO: 11), HIP1CysDimer (SEQ ID NO: 12) and HIP2CysDimer (SEQ ID NO: 13)). Such a modification appears to increase the stability of HIPCys variants by avoiding those proteases which recognize HIP or HIPCys variants in monomer form.

In another embodiment, cysteine proislet peptide variants are blocked with a N-terminal acetyl group and a C-terminal amide group.

In another embodiment, HIPCys variants are blocked with a N-terminal acetyl group and a C-terminal amide group (HIP3CysBlocked (SEQ ID NO: 14), HIP1CysBlocked (SEQ ID NO: 15) and HIP2CysBlocked (SEQ ID NO: 16)). Such modifications appear to render the sequence less susceptible to protease cleavage in serum with those proteases that normally recognize free ends and resulting in a compound which is capable of forming dimers in solution (HIP3CysBlockedDimer (SEQ ID NO: 17), HIP1CysBlockedDimer (SEQ ID NO: 18) and HIP2CysBlockedDimer (SEQ ID NO: 19)) thereby increasing the stability of HIPCysBlocked variants by avoiding those proteases which recognize HIP or HIPCysBlocked variants in monomer form.

In another embodiment, the cysteine proislet peptide variants are modified by covalently binding a dimeric maleimide activated 40 Kd PEG construct to the C-terminal cysteine residue.

In another embodiment, HIPCys variants are modified by covalently binding a dimeric maleimide activated 40 Kd PEG construct to the C-terminal cysteine residue (HIP3CysPEG (SEQ ID NO: 20), HIP1CysPEG (SEQ ID NO: 21) and HIP2CysPEG (SEQ ID NO: 22)). Such a modification appears to improve the stability of HIPCys in serum resulting in increased bioavailability and dosing efficacy of HIPCys variants in therapeutic strategies for stimulating islet neogenesis and reversing diabetes in vivo.

In another embodiment, the CysBlocked proislet peptide variants are modified by covalently binding a dimeric maleimide activated 40 Kd PEG construct.

In another embodiment, HIPCysBlocked variants are modified by covalently binding a dimeric maleimide activated 40 Kd PEG construct (HIP3CysBlockedPEG (SEQ ID NO: 23), HIP1CysBlockedPEG (SEQ ID NO: 24) and HIP2CysBlockedPEG (SEQ ID NO: 25)). Such a modification appears to improve the stability of HIPCysBlocked variants in serum resulting in increased bioavailability and dosing efficacy of HIPCysBlocked variants in therapeutic strategies for stimulating islet neogenesis and reversing diabetes in vivo.

Further embodiments provide methods for administering the Optimized proislet peptide compounds, including Optimized HIPs (SEQ ID NOs: 5-25), alone or in combination with other therapeutic agents for stimulating pancreatic islet cell regeneration. In various embodiments, the methods disclosed herein can be practiced by administration of a therapeutically effective amount of Optimized proislet peptide alone, in combination with insulin, in combination with insulin and another agent, and in combination with one or more agents other than insulin.

Other embodiments provide pharmaceutical formulations and unit dose forms of Optimized proislet peptide compounds, including Optimized HIP. In one embodiment, the pharmaceutical formulation provided contains Optimized HIP alone or in combination with one or more other active pharmaceutical ingredients (APIs). In one embodiment, the API is an or agents in soluble liposome preparations that allow the Optimized HIP to be administered by a variety of routes, including subcutaneously, intramuscularly, intravenously, and even orally, depending on the formulation selected. In one embodiment, the formulation is for general systemic administration, but in other embodiments, the formulation comprises a targeting agent for targeted administration to specific locations, receptors, cells, tissues, organs, or organ systems within a subject.

In other embodiments, provided are methods of treating a pathology associated with impaired pancreatic function in a subject in need of such treatment. The method may comprise the step of administering one or more agents for stimulating pancreatic islet cell regeneration in addition to the Optimized proislet peptide compounds, including Optimized HIP. In one aspect of this embodiment, the agents are selected from HIP or HIP-related peptide other than Optimized HIP, amylin/Pramlintide (SYMLIN™), exendin-4 (EXENATIDE™), GIP, GLP-1, GLP-1 receptor agonists, GLP-1 analogs, hamster INGAP peptide and related peptides, Liraglutide (NN2211), and a dipeptidyl peptidase inhibitor, which blocks the degradation of GLP-1.

In another embodiment, methods of treating a pathology associated with impaired pancreatic function in a subject in need of such treatment are provided. The method may comprises one or more of the steps of (1) intensifying glycemic control; (2) administering oral vitamin D3 (cholecalciferol) or vitamin D2 (ergocalciferol) to maintain 25-hydroxyvitamin levels above 40 ng/ml; (3) administering one or more immune therapies for protecting new islet cell formation, including administration of immunosuppressive agents; (4) administering Optimized proislet peptide compounds, including Optimized HIP in combination with insulin but decreasing the insulin administered over time; and (5) repeatedly administering a therapy for protection of islets, preferably on a 3 to 24 month basis, depending on the selected immune therapy, in addition to the step of administering Optimized HIP.

In another embodiment, methods of treating a pathology associated with impaired pancreatic function in a subject in need of such treatment are provided. The method may comprise one or more of the steps of: (1) intensifying glycemic control; (2) administering oral vitamin D3 (cholecalciferol) to maintain 25-hydroxyvitamin levels above 40 ng/ml; (3) administering an agent for stimulating pancreatic islet regeneration in addition to Optimized proislet peptide compounds, including Optimized HIP, including but not limited to HIP and HIP analogs other than Optimized HIP; (4) co-administering an agent selected from the group consisting of amylin/Pramlintide (SYMLIN™), exendin-4 (EXENATIDE™; BYETTA™), Gastrin, Epidermal Growth Factor and Epidermal Growth Factor analog GIP, GLP-1, GLP-1 receptor agonists, GLP-1 analogs, INGAP, Liraglutide (NN2211), and a dipeptidyl peptidase IV inhibitor, which blocks the degradation of GLP-1; and (5) reducing, or tapering off, administration of another diabetes therapy.

In another embodiment, methods of treating a pathology associated with impaired pancreatic function in a subject in need of such treatment are provided. The method may comprise in addition to administering Optimized proislet peptide compounds, including Optimized HIP, the step of administering one or more agents that inhibit, block, or destroy the autoimmune cells that target pancreatic islets. Such therapies are termed "immune therapies" above. In various aspects of this embodiment, the agents that inhibit, block, or destroy the autoimmune cells that target pancreatic islets are selected from the group consisting of the following given individually or in combination with one another. Anti CD-3 antibodies including hOKT3γ1(Ala-Ala) (teplizumab); ChAglyCD3 that target the immune response and specifically block the T-lymphocytes that cause beta cell death in type 1 diabetes; the Cytotoxic T-lymphocyte antigen 4, CLTA-4 Ig (Abatacept); Sirolimus (Rapamycin) alone in combination with either Tacrolimus (FK506) or IL-2 (rapamune); Rapamune alone or in combination with Proleukin (aldesleukin); a heat-shock protein 60 (Diapep277); an anti-Glutamic Acid Decarboxylase 65 (GAD65) vaccine; the diabetes-suppressive dendritic cell vaccine, GSK189075, diazoxide and statin drugs including atorvastatin utilized as an agent to preserver beta cell function, Mycophenolate Mofetil alone or in combination with Daclizumab; the anti-CD20 agent, Rituximab; Campath-1H (Anti-CD52 Antibody), lysofylline; polyclonal anti-T-lymphocyte globulin (ATG/Thyrnoglobulin), Granulocyte colony-stimulating factor, Neulasta (Pegfilgrastim), Vitamin D, both 25 hydroxy and 1,25 hydroxyvitamin D supplementation; IBC-VSO vaccine, which is a synthetic, metabolically inactive form of insulin designed to prevent pancreatic beta-cell destruction; interferon-alpha; a vaccine using $CD4^+$ $CD25^+$ antigen-specific regulatory T cells or any agent or agents designed to suppress the immune attack upon beta cells within the islets of Langerhans, Prochymal (Human Adult Stem Cells), the anti-inflamatory Anakinra and the antinflamatory agent, Deoxyspergualin, an anti-inflamatory agent that blocks proinflammatory cytokine production and inhibits T-cells and B-cells, These or similar agents can be used in the combination therapies that utilize regulatory T cells either directly or through the use of immunotherapy to arrest the destruction of insulin-producing cells.

In another embodiment, methods of treating a pathology associated with impaired pancreatic function in a subject in need of such treatment, wherein at least one symptom of the pathology associated with impaired pancreatic function is treated or reduced as a result of the administration of Optimized proislet peptide compounds, including Optimized HIP are provided. In one aspect of this embodiment, the symptom is selected from low levels of insulin or insulin activity, insulin resistance, hyperglycemia, hemoglobin A1C level greater than 6.0%, frequent urination, excessive thirst, extreme hunger, unusual weight loss or gain, being overweight, increased fatigue, irritability, blurry vision, genital itching, odd aches and pains, dry mouth, dry or itchy skin, impotence, vaginal yeast infections, poor healing of cuts and scrapes, excessive or unusual infections, loss or worsening of glycemic control, fluctuations in blood glucose, fluctuations in blood glucagon, and fluctuations in blood triglycerides, with hyperglycemia ultimately leading to microvascular and macrovascular complications, which include visual symptoms that lead to blindness, accelerated kidney impairment that can lead to renal failure necessitating dialysis and kidney transplant and neuropathy leading to foot ulcers and amputations. Additionally, recent studies have demonstrated both microvascular and macrovascular/cardiovascular risk reduction among type 1 diabetes patients who have improved glycemic control.

In another embodiment, methods of treating a pathology associated with impaired pancreatic function in a subject in need of such treatment are provided. The pathology associated with impaired pancreatic function is any one of type 1 diabetes, new onset type 1 diabetes, type 2 diabetes, latent autoimmune diabetes of adulthood, pre-diabetes, impaired fasting glucose, impaired glucose tolerance, insulin resistant syndrome, metabolic syndrome/dysmetabolic syndrome, being overweight, obesity, hyperlipidemia, hypertriglyceridemia, eating disorders, anovulatory cycles and polycystic ovarian syndrome.

Embodiments of the disclosure also provide antibodies which selectively bind to an Optimized proislet peptide compounds, including Optimized HIP. In one embodiment, the antibody is a monoclonal antibody. In another embodiment, the antibody is a polyclonal antibody. Such antibodies can be used in diagnostic methods provided herein, which methods comprise detecting Optimized HIP levels in the serum or tissue of a mammal. In one embodiment the diagnostic method is used to monitor treatment with Optimized HIP to ensure that therapeutically effective levels are being achieved in a patient receiving such therapy.

Embodiments of the disclosure also provide kits for treating a patient having type 1 or type 2 diabetes or other condition in which there are aberrant insulin levels, perturbation in glucose metabolism or insulin resistance, comprising a therapeutically effective dose of Optimized proislet peptide compounds, including Optimized HIP and optionally at least one agent for stimulating GLP-1 receptors or enhancing GLP-1 levels, promoting beta cell regeneration, increased satiety, decreased food intake and weight loss, either in the same or separate packaging, and instructions for its use. Further embodiments provide a kit for measuring Optimized proislet peptide compounds, including Optimized HIP levels in a sample, the kit comprising a Optimized proislet peptide antibody, including Optimized HIP-specific antibody and optionally Optimized proislet peptide compounds, including Optimized HIP and optionally a labeling means.

DESCRIPTION OF DRAWINGS

The file of this patent contains at least one photograph or drawing executed in color. Copies of this patent with color drawing(s) or photograph(s) will be provided by the Patent and Trademark Office upon request and payment of necessary fee.

For a fuller understanding of the nature and advantages of the present invention, reference should be had to the following detailed description taken in connection with the accompanying drawings, in which:

FIG. 4A is a graph depicting the number of islets in mice treated with HIP2 and HIP3.

FIG. 5 is an immunofluorescent stain for insulin on mouse pancreatic tissue treated with HIP.

DETAILED DESCRIPTION

Figure 1:
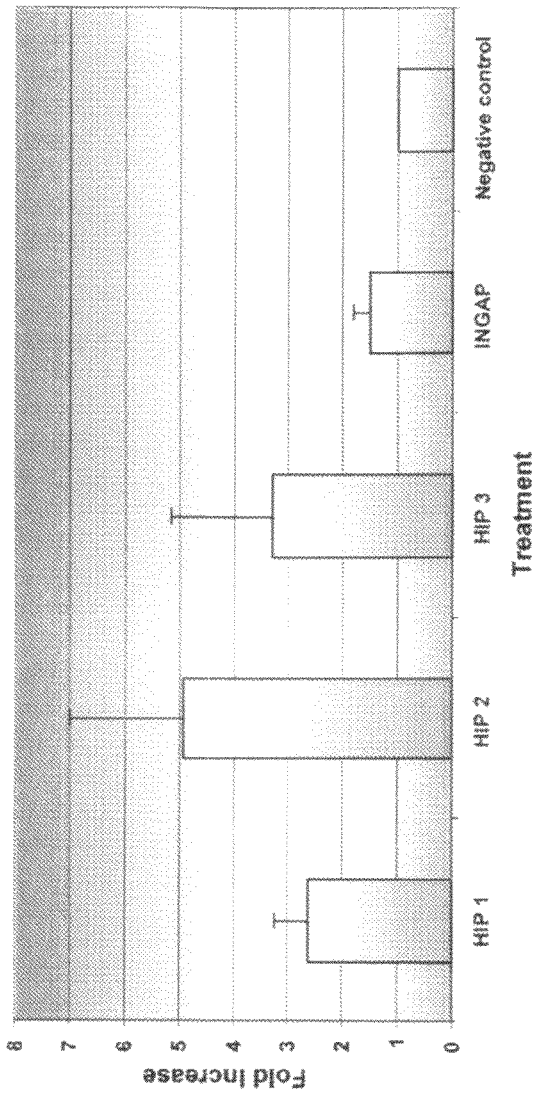
FIG. 1 is a graph depicting the insulin levels after incubation in culture with human pancreatic ductal tissue with HIP1, HIP2 and HIP3.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

Insulin has been, since 1922, the primary if not only available therapy for the treatment of type 1 diabetes and other conditions related to the lack of or diminished efficacy or production of insulin. However, diabetic patients on insulin do not have normal glucose metabolism, because insulin is only part of the missing and aberrant pancreatic function.

To date, there has been no single or combination therapy that has been successfully used to treat the underlying disease mechanisms of either type 1 or type 2 diabetes. Development of a successful treatment that stimulates regeneration of insulin-producing cells within the pancreas will represent a significant treatment breakthrough for patients with diabetes. Some literature misleadingly uses the term "islet cells" to refer either just to beta cells or to entire islets. However, it is important to distinguish between beta cells and islets because some treatment alternatives seek to increase the number of beta cells, whereas there have been no treatments available to endogenously replace entire islets other than islet transplantation.

Despite decades of research and the advent of pancreatic islet transplantation in 1974 and newer claims of success resulting from the Edmonton Protocol for islet transplantation, these approaches have not been very successful in the United States. For example, at four years post-transplant, fewer than 10% of patients who have received islet transplants remain insulin independent. Additionally, there is an 18% rate of serious side effects. It is well established that at the onset of type 1 diabetes, patients have already lost the majority of their islets and their number of islets continues to steadily decline. However, more recent studies have found that at the time of diagnosis of type 2 diabetes, patients exhibit a loss of at least 50% of the islet mass and number. As with type 1 patients, the number and mass of islets continues to decline, not from autoimmune attack, but because the beta cells effectively become "burned out." Although this decline occurs more rapidly in type 1 patients, there is still a decline of 10-20% per year among type 2 patients.

In a normally functioning pancreas, small numbers of islets die naturally on a day-by-day basis and are replaced as required to keep glucose levels under control. On average, this regenerative process known as islet neogenesis replaces islets at a rate of approximately 2% per month. In nondiabetic patients, the beta cell mass within the existing islets can expand or contract depending on the insulin needs of the individual. This process is referred to as "beta cell proliferation" does not occur in patients with type 1 diabetes and is limited in type 2 patients.

The study of islet neogenesis is not new. In 1920, it was reported that an obstructive pancreatic stone resulted in atrophy to most of the pancreas but an increase in islets. It was then hypothesized that ligating (binding) the pancreatic ducts might lead to the identification of a substance that could be useful in the treatment of diabetes. Surgeons ligated the pancreatic ducts of diabetic children in the hopes of producing substances that would form new islets. Although the positive effects of these procedures were short-lived, they demonstrated the potential for islet restoration in man.

Pancreatic ductal ligation studies that were intended to create a hamster model for pancreatitis resulted in the formation of many new islets. This research led to the isolation of a hamster peptide referred to as the Islet Neogenesis Associated Peptide, or INGAP. In the clinical development of INGAP, it was further demonstrated that new human islets could be differentiated from the stem-cell-like islet progenitor cells that reside throughout the adult pancreas even decades after the onset of type 1 diabetes.

Separate from the concept of using ductal ligation to produce new islets, research was carried out regarding the potential regeneration of islets during pregnancy. It has been reported that islets were being formed in late embryogenesis and stated that the islet population continues to grow postnatally through a process of metamorphosis from surrounding ductal tissue.

The primary way in which patients with type 1 or late-stage type 2 diabetes manage their disease is by administering insulin, either via subcutaneous injection or by using a subcutaneous pump infusion. As well as the obvious lifestyle disadvantages, insulin therapy does not match the body's normal control mechanisms and therefore does not fully manage glucose fluctuations. As shown by the adjacent chart, even the best-controlled type 1 diabetic patients do not have anything remotely like a normal glucose metabolism. This is because insulin secretion is only part of the missing pancreatic function.

Investigators have evaluated whether endogenous production of insulin can be stimulated by drug treatment. For example, over the past several decades, several therapies have been studied in which a peptide involved in glucose metabolism, or analogs of such peptides, have been administered to diabetic patients. These therapies include the administration of peptides with amino acid sequences similar to those of Glucagon Like Peptide-1 (GLP-1), and such peptides include: GLP-1 receptor analogs, Exendin-4, Exenatide/BYETTA™, which is derived from the Gila Monster, Januvia™, Gastric Inhibitory Peptide/Glucose-Dependent Insulinoptropic polypeptide (GIP), compounds homologous to GLP-1, such as Liraglutide (NN2211), Dipeptidyl Peptidase-4 Inhibitors, which inhibit the breakdown of GLP-1, Gastrin, Epidermal Growth Factor and Epidermal Growth Factor Analogs, and Hamster derived Islet Neogenesis Associated Peptide (INGAP).

None of these treatments have proven effective in reversing the underlying mechanisms of diabetes. Generation of new islets not only forms insulin-producing beta cells, it also forms the other cells involved in the glucose metabolism. Consequently, if enough new islets are generated, the patient is ultimately able to recover glycemic control. Therefore, islet neogenesis presents the possibility not only to treat, but actually to reverse diabetes.

For any islet cell neogenesis agent to be effective, the pancreas must be "elastic" with respect to its ability to generate new islet cells. Proof of the elasticity of the pancreas with respect to the generation of new pancreatic islets throughout one's lifetime in response to pancreatic islet death or apoptosis has replaced the long held concept that the number of insulin producing islet structures is fixed at birth and maintained throughout life, whereas the plasticity and ability of beta cells to proliferate within existing islets has been well established. It is currently accepted that pancreatic islet neogenesis occurs from preexisting pancreatic cells through differentiation of progenitor cells found amongst both the endocrine and exocrine fractions of the pancreas. Data demonstrates that, even decades after the onset of type 1 diabetes, pancreatic islets can be regenerated.

For example, patients with type 1 diabetes are able to make normal levels of C-peptide during pregnancy. Several teams have found a paradoxical rise in C-peptide levels during the first trimester of pregnancy into the normal range in as many as one-third of all pregnant type 1 patients. This rise in C-peptide is accompanied by a significant reduction in insulin requirements with some patients being able to discontinue insulin transiently during the first trimester of pregnancy. This rise in C-peptide during pregnancy that occurs within 10 weeks of gestation among patients, despite no measurable C-peptide prior to pregnancy, implies the restoration of functioning islet structures. It is hypothesized that the islet neogenesis that occurs during pregnancy results from the concomitant rise in endogenous steroid production and a down regulation of the immune system preventing immune attack on the fetus, which likely also plays a role in suppression of lymphocyte attack on the islets. Along with immune suppression, it is also speculated that there is an up regulation of maternal islet growth promoting factors during pregnancy to compensate for the lowering of the maternal glucose setpoint in pregnancy. Animal models have also demonstrated that islet neogenesis precedes the development of beta cell expansion during pregnancy and it has been demonstrated that human pancreatic progenitor cells differentiate into islets. Similarly, patients who have been on long term immunosuppression for kidney transplantation have been observed to regenerate insulin producing islets.

Over the past decade, clinical trials have been conducted to evaluate the impact of a number of immune modulators that may arrest the destruction of the beta cells of the pancreas. Anti CD-3 antibodies such as hOKT3γ1(Ala-Ala) and ChAglyCD3 that target the immune response and specifically block the T-lymphocytes that cause beta cell death in type 1 diabetes have been utilized for this purpose, as have treatments involving the administration of Sirolimus (Rapamycin), Tacrolimus (FK506), a heat-shock protein 60 (DIAPEP277™), an anti-Glutamic Acid Decarboxylase 65 (GAD65) vaccine, Mycophenolate Mofetil alone or in combination with Daclizumab, the anti-CD20 agent, polyclonal Anti-T-lymphocyte globulin (ATG), lysofylline, Rituximab, Campath-1H (Anti-CD52 Antibody), Vitamin D, IBC-VSO vaccine, which is a synthetic, metabolically inactive form of insulin designed to prevent pancreatic beta-cell destruction, and interferon-α vaccination using CD4+CD25+ antigen-specific regulatory T cells. These therapeutic approaches are intended to utilize regulatory T cells either directly or through the use of immunotherapy to arrest the destruction of insulin-producing cells. The aim of these trials is to determine the ability of such agents to preserve islet function by preventing further immune attack on the beta cells of the islets of the pancreas.

Additionally, recent studies have found that vitamin D may play an important immune modulating role in the prevention of type 1 diabetes. Up to 54.7% of populations in the US, regardless of latitude, have low 25 hydroxyvitamin D levels. Vitamin D deficiency has been demonstrated, not only to be associated with the increased risk of type 1 diabetes and seen at the onset of type 1 diagnosis, but also is commonly seen among both patients with type 1 and 2 diabetes. Maintaining levels above 40 ng/ml are recommended to sustain normal immune function. No adverse effects have been seen with doses up to 10,000 IU/day.

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

It must also be noted that as used herein and in the appended claims, the singular forms "a", "an", and "the" include plural reference unless the context clearly dictates otherwise. Thus, for example, reference to a "fibroblast" is a reference to one or more fibroblasts and equivalents thereof known to those skilled in the art, and so forth.

As used herein, the term "about" means plus or minus 10% of the numerical value of the number with which it is being used. Therefore, about 50% means in the range of 45%-55%. As used herein, "proislet peptide" refers to proteins or peptides derived from such proteins that stimulate islet cell neogenesis, including, but not limited to, human REG3A (SEQ ID NO: 1), human REG3G (SEQ ID NO: 28), human REG1A, human REG1B, human REG4, hamster INGAP (SEQ ID NO: 27), hamster REG2, hamster REG3G, rat REG1, rat PAP/REG3B, rat PAPS, rat REG3G, mouse REG1, mouse REG2, mouse REG3A, mouse REG3B, mouse REG3G, mouse REG3S, mouse REG4, bovine PTP, chimpanzee, cow, dog, sheep and analogs and homologs of such proteins, and peptides fragments derived from such proteins or homologs thereof. The protein sequences of such proislet peptides are publicly available. Proislet peptides further include peptides which are fragments of REG3A, INGAP or homolog proteins that contain the active fourteen amino acid sequence of HIP2 (or the corresponding sequence for each homolog) (see Table 1 below) and are less than 150 amino acids, less than 125 amino acids, less than 100 amino acids, less than 75 amino acids, less than 50 amino acids or less than 25 amino acids. Examples of such peptides (which provide the active fourteen amino acid sequence) include, but are not limited to, the following:

TABLE 1

| Human REG3A | I G L H D P T Q G T E P N G | SEQ ID NO: 4 |
|---|---|---|
| Chimp | I G L H D P T Q G S E P D G | SEQ ID NO: 60 |
| Hamster INGAP | I G L H D P S H G T L P N G | SEQ ID NO: 61 |
| Mouse REG3A | I G L H D P T M G Q Q P N G | SEQ ID NO: 62 |
| Norway Rat REG3 | I W L H D P T M G Q Q P N G | SEQ ID NO: 63 |
| Cow | I G L H D P T E G S E P D A | SEQ ID NO: 64 |
| Dog | M G L H D P T E G Y E P N A | SEQ ID NO: 65 |
| Sheep | I G L H D P T E G S E P N A | SEQ ID NO: 66 |
| Human REG1A | I G L H D P K K N R R W H W | SEQ ID NO: 67 |
| Human REG1B | I G L H D P K K N R R W H W | SEQ ID NO: 68 |

TABLE 1-continued

| | | |
|---|---|---|
| Rat REG1 | I G L H D P K N N R R W H W | SEQ ID NO: 69 |
| Mouse REG1 | T G L H D P K R N R R W H W | SEQ ID NO: 70 |
| Mouse REG2 | T G L H D P K S N R R W H W | SEQ ID NO: 71 |
| Hamster REG2 | I G L H D P K N N R R W H W | SEQ ID NO: 72 |
| Rat REG3 | I W L H D P T M G Q Q P N G | SEQ ID NO: 73 |
| Rat PAP/REG3B | I G L H D P T L G G E P N G | SEQ ID NO: 74 |
| Rat PAP3 | I G L H D P T L G Q E P N R | SEQ ID NO: 75 |
| Mouse REG3A | I G L H D P T M G Q Q P N G | SEQ ID NO: 76 |
| Mouse REG3B | I G L H D P T L G A E P N G | SEQ ID NO: 77 |
| Mouse REG3G | I G L H D P T L G Y E P N R | SEQ ID NO: 78 |
| Rat REG3G | I G L H D P T L G Q E P N R | SEQ ID NO: 79 |
| Hamster REG3G | I G L H D P T L G Q E P N G | SEQ ID NO: 80 |
| Human REG3G | I G L H D P T Q G S E P D G | SEQ ID NO: 81 |
| Mouse REG3S | I G L H D L S L G S L P N E | SEQ ID NO: 82 |
| Bovine PTP | I G L H D P T E G S E A N A | SEQ ID NO: 83 |
| Hamster INGAP | I G L H D P S H G T L P N G | SEQ ID NO: 84 |
| Human REG4 | I G L H D P Q K R Q Q W Q W | SEQ ID NO: 85 |
| Mouse REG4 | I G L H D P Q K K Q L W Q W | SEQ ID NO: 86 |
| Chimp | I G L H D P T Q G S E P D G | SEQ ID NO: 87 |
| Cow | I G L H D P T E G S E P D A | SEQ ID NO: 88 |
| Dog | M G L H D P T E G Y E P N A | SEQ ID NO: 89 |
| Sheep | I G L H D P T E G S E P N A | SEQ ID NO: 90 |

Such peptide fragments include, but are not limited to, HIP1, HIP2, HIP3, INGAP peptide (SEQ ID NO: 26), and homologs thereof, identified below. There has been a similar human gene found in man to the rat gene, which is referred to as the Reg gene, and is the gene upon which HIP has been found in humans and a high homology between species of Human proIslet Peptide and other mammalian species. The following species homology chart shows that the HIP related sequence is exquisitely conserved through evolution. It is likely that each of these sequences will have some efficacy in humans, but none is exactly matched to the human active sequence of HIP.

Species Homology

| | | |
|---|---|---|
| Human REG3A | W I G L H D P T Q G T E P N G E | SEQ ID NO: 30 |
| Chimp | W I G L H D P T Q G S E P D G G | SEQ ID NO: 31 |
| Hamster INGAP | W I G L H D P S H G T L P N G S | SEQ ID NO: 32 |
| Mouse REG3A | W I G L H D P T M G Q Q P N G G | SEQ ID NO: 33 |
| Norway Rat REG3 | W I W L H D P T M G Q Q P N G G | SEQ ID NO: 34 |
| Cow | W I G L H D P T E G S E P D A G | SEQ ID NO: 35 |
| Dog | W M G L H D P T E G Y E P N A D | SEQ ID NO: 36 |
| Sheep | W I G L H D P T E G S E P N A G | SEQ ID NO: 37 |

The table above compares a sixteen amino acid stretch of a human peptide containing the fourteen amino acid HIP2 sequence compared to other species.

| | | |
|---|---|---|
| Human REG3A | W I G L H D P T Q G T E P N G | SEQ ID NO: 3 |
| Chimp | W I G L H D P T Q G S E P D G | SEQ ID NO: 38 |
| Hamster INGAP | W I G L H D P S H G T L P N G | SEQ ID NO: 39 |
| Mouse REG3A | W I G L H D P T M G Q Q P N G | SEQ ID NO: 40 |
| Norway Rat REG3 | W I W L H D P T M G Q Q P N G | SEQ ID NO: 41 |
| Cow | W I G L H D P T E G S E P D A | SEQ ID NO: 42 |
| Dog | W M G L H D P T E G Y E P N A | SEQ ID NO: 43 |
| Sheep | W I G L H D P T E G S E P N A | SEQ ID NO: 44 |
| Human REG3A | I G L H D P T Q G T E P N G | SEQ ID NO: 4 |
| Chimp | I G L H D P T Q G S E P D G | SEQ ID NO: 45 |
| Hamster INGAP | I G L H D P S H G T L P N G | SEQ ID NO: 46 |
| Mouse REG3A | I G L H D P T M G Q Q P N G | SEQ ID NO: 47 |
| Norway Rat REG3 | I W L H D P T M G Q Q P N G | SEQ.ID NO: 48 |
| Cow | I G L H D P T E G S E P D A | SEQ ID NO: 49 |

-continued

| Dog | M G L H D P T E G Y E P N A | SEQ ID NO: 50 |
|---|---|---|
| Sheep | I G L H D P T E G S E P N A | SEQ ID NO: 51 |
| Human REG3A | I G L H D P T Q G T E P N G E | SEQ ID NO: 2 |
| Chimp | I G L H D P T Q G S E P D G G | SEQ ID NO: 52 |
| Hamster INGAP | I G L H D P S H G T L P N G S | SEQ ID NO: 27 |
| Mouse REG3A | I G L H D P T M G Q Q P N G G | SEQ ID NO: 53 |
| Norway Rat REG3 | I W L H D P T M G Q Q P N G G | SEQ ID NO: 54 |
| Cow | I G L H D P T E    S E P D A G | SEQ ID NO: 55 |
| Dog | M G L H D P T E G Y E P N A D | SEQ ID NO: 56 |
| Sheep | I G L H D P T E G S E P N A G | SEQ ID NO: 57 |

As used herein, "Optimized proislet peptide" refers to variations of a proislet peptide, including, but not limited to, human REG3A, human REG3G, human REG1A, human REG1B, human REG4, hamster INGAP, hamster REG2, hamster REG3G, rat REG1, rat PAP/REG3B, rat PAP3, rat REG3G, mouse REG1, mouse REG2, mouse REG3A, mouse REG3B, mouse REG3G, mouse REG3S, mouse REG4, bovine PTP, chimpanzee, cow, dog, sheep and analogs and homologs of such proteins, and peptides fragments derived from such proteins or homologs thereof, HIP1, HIP2 and/or HIP3 or homologs of such peptides (SEQ ID NOs: 31-90), wherein the peptide has been modified to increase the stability, solubility or bioavailability of such peptides as described in the various embodiments. For purposes of this disclosure, stability refers to the peptide's resistance to degradation by in-serum proteases which target and degrade non-Optimized proislet peptides, REG3A, REG3G, INGAP, REG3G peptide, INGAP peptide, HIP1, HIP2 and/or HIP3 or homologs of such peptides. Also, for purposes of this disclosure, bioavailability refers to the amount of peptide available for in vivo therapeutic use by the target cells, pathways and/or systemic mechanisms based on the peptide's ability to avoid degradation by proteases and other systemic pathways that degraded non-Optimized proislet peptides, human REG3A, human REG3G, human REG1A, human REG1B, human REG4, hamster INGAP, hamster REG2, hamster REG3G, rat REG1, rat PAP/REG3B, rat PAP3, rat REG3G, mouse REG1, mouse REG2, mouse REG3A, mouse REG3B, mouse REG3G, mouse REG3S, mouse REG4, bovine PTP, chimpanzee, cow, dog, sheep and analogs and homologs of such proteins, HIP1, HIP2 and/or HIP3 or homologs of such peptides. Preferably, Optimized proislet peptides refers to REG3G peptide, INGAP peptide, HIP3, HIP1 and/or HIP 2 or homologs that are blocked by the addition of a C-terminal amide group and a N-terminal acetyl group, pegylated, and a combination thereof.

As used herein, "Optimized HIP" refers to variations of HIP, HIP1 and/or HIP2 wherein the peptide has been modified to increase the stability, solubility or bioavailability of HIP, HIP1 or HIP2 as described in embodiments herein. For purposes of this disclosure, stability refers to the peptide's resistance to degradation by in-serum proteases which target and degrade non-Optimized HIP3, HIP1 and/or HIP2. Also, for purposes of this disclosure, bioavailability refers to the amount of peptide available for in vivo therapeutic use by the target cells, pathways and/or systemic mechanisms based on the peptide's ability to avoid degradation by proteases and other systemic pathways that degraded non-Optimized HIP3, HIP1 and/or HIP2. Preferably, Optimized HIP refers to HIP3, HIP1 and/or HIP 2 that are blocked by the addition of a C-terminal amide group and a N-terminal acetyl group, pegylated, and a combination thereof.

As used herein, "treating" a condition or patient refers to taking steps to obtain beneficial or desired results, including clinical results. For purposes of this disclosure, beneficial or desired clinical results include, but are not limited to, alleviation or amelioration of one or more symptoms of diabetes, diminishment of extent of disease, delay or slowing of disease progression, amelioration, palliation or stabilization of the disease state, and other beneficial results described below. Symptoms of diabetes include low or inadequate levels of insulin or insulin activity, frequent urination, excessive thirst, extreme hunger, unusual weight loss, increased fatigue, irritability, blurry vision, genital itching, odd aches and pains, dry mouth, dry or itchy skin, impotence, vaginal yeast infections, poor healing of cuts and scrapes, excessive or unusual infections, hyperglycemia, loss of glycemic control, fluctuations in postprandial blood glucose, fluctuations in blood glucagon, fluctuations in blood triglycerides. Diabetes may be diagnosed by methods well known to one of ordinary skill in the art. For example, commonly, diabetics have a plasma blood glucose result of greater than 126 mg/dL of glucose. Pre diabetes, which may also be treated by the compositions and methods disclosed herein, is commonly diagnosed in patients with a blood glucose level between 100 and 125 mg/dL of glucose. Other symptoms may also be used to diagnose diabetes, related diseases and conditions, and diseases and conditions affected by diminished pancreatic function.

As used herein, "reduction" of a symptom or symptoms (and grammatical equivalents of this phrase) means decreasing of the severity or frequency of the symptom(s), or elimination of the symptom(s).

The term "inhibiting" includes the administration of a compound of the present disclosure to prevent the onset of the symptoms, alleviating the symptoms, or eliminating the disease, condition or disorder.

As used herein, a "pathology associated with impaired pancreatic function" is one in which the pathology is associated with a diminished capacity in a subject for the pancreas of the subject to produce and/or secrete hormones and/or cytokines. Preferably this hormone or cytokine is insulin. Pathologies that are associated with impaired pancreatic function include type 1 diabetes, new onset type 1 diabetes, type 2 diabetes, latent autoimmune diabetes of adulthood, pre-diabetes, impaired fasting glucose, impaired glucose tolerance, insulin resistant syndrome, metabolic syndrome, being overweight, obesity, hyperlipidemia, hypertriglyceridemia, eating disorders and polycystic ovarian syndrome.

As used herein, "administering" or "administration of" a drug or therapeutic to a subject (and grammatical equivalents of this phrase) includes both direct administration, including self-administration, directly into or onto a target tissue or to administer a therapeutic to a subject whereby the therapeutic positively impacts the tissue to which it is targeted, and indirect administration, including the act of prescribing a drug. For example, as used herein, a physician who instructs a patient to self-administer a drug and/or provides a patient with a prescription for a drug is administering the drug to the patient.

As used herein, a "subject" or "patient" is a mammal, typically a human, but optionally a mammalian animal of veterinary importance, including but not limited to horses, cattle, sheep, dogs, and cats.

As used herein, a "manifestation" of a disease refers to a symptom, sign, anatomical state (e.g., lack of islet cells), physiological state (e.g., glucose level), or report (e.g., triglyceride level) characteristic of a subject with the disease.

As used herein, a "therapeutically effective amount" of a drug or agent is an amount of a drug or agent that, when administered to a subject with a disease or condition will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

As used herein, a "prophylactically effective amount" of a drug is an amount of a drug that, when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose and may occur only after administration of a series of doses. Thus, a prophylactically effective amount may be administered in one or more administrations.

By "pharmaceutically acceptable", it is meant the carrier, diluent or excipient must be compatible with the other ingredients of the formulation and not deleterious to the recipient thereof.

As used herein, "TID", "QD" and "QHS" have their ordinary meanings of "three times a day", "once daily," and "once before bedtime", respectively.

Administration of an agent "in combination with" includes parallel administration (administration of both the agents to the patient over a period-of time, such as administration of a monoclonal antibody and a peptide hormone such as an incretin hormone or analog on alternate days for one month), co-administration (in which the agents are administered at approximately the same time, e.g., within about a few minutes to a few hours of one another), and co-formulation (in which the agents are combined or compounded into a single dosage form suitable for oral, subcutaneous or parenteral administration).

"DPP-4 Inhibitors" are dipeptidyl peptidase-4 inhibitors.

"Hamster INGAP" is a non-human islet neogenesis associated peptide having the sequence Ile-Gly-Leu-His-Asp-Pro-Ser-His-Gly-Thr-Leu-Pro-Asn-Gly-Ser (SEQ ID NO: 26). This peptide is a fragment of the Hamster INGAP protein having the sequence Ile-Gly-Leu-His-Asp-Pro-Ser-His-Gly-Thr-Leu-Pro-Asn-Gly-Ser (SEQ ID NO: 27).

"GIP" is Gastric Inhibitory Peptide, also known as Glucose-Dependent Insulinotropic Polypeptide.

"GLP-1" is Glucagon-like Peptide 1.

"HIP3" (Ile-Gly-Leu-His-Asp-Pro-Thr-Gln-Gly-Thr-Glu-Pro-Asn-Gly-Glu (SEQ ID NO: 2)) is a Human proIslet Peptide in purified, synthetic, or recombinant form. HIP3 has a molecular weight of about 1564.6.

"HIP1" (Trp-Ile-Gly-Leu-His-Asp-Pro-Thr-Gln-Gly-Thr-Glu-Pro-Asn-Gly (SEQ ID NO: 3)) is a Human proIslet Peptide in purified, synthetic, or recombinant form.

"HIP2" (Ile-Gly-Leu-His-Asp-Pro-Thr-Gln-Gly-Thr-Glu-Pro-Asn-Gly (SEQ ID NO: 4)) is a Human proIslet Peptide in purified, synthetic, or recombinant form. HIP2 has a molecular weight of about 1435.5.

HIP3Blocked or HIP3B (Ac-Ile-Gly-Leu-His-Asp-Pro-Thr-Gln-Gly-Thr-Glu-Pro-Asn-Gly-Glu-NH2) (SEQ ID NO: 5)) is a Human proIslet Peptide which has been blocked with a N-terminal acetyl group and a C-terminal amide group, in purified, synthetic, or recombinant form. HIPB has a molecular weight of about 1605.7.

HIP1Blocked (Ac-Trp-Ile-Gly-Leu-His-Asp-Pro-Thr-Gln-Gly-Thr-Glu-Pro-Asn-Gly-NH2 (SEQ ID NO: 6)) is a Human proIslet Peptide which has been blocked with a N-terminal acetyl group and an C-terminal amide group, in purified, synthetic, or recombinant form.

HIP2Blocked or HIP2B (Ac-Ile-Gly-Leu-His-Asp-Pro-Thr-Gln-Gly-Thr-Glu-Pro-Asn-Gly-NH2) (SEQ ID NO: 7)) is a Human proIslet Peptide which has been blocked with a N-terminal acetyl group and an C-terminal amide group, in purified, synthetic, or recombinant form. HIP2B has a molecular weight of about 1476.6.

INGAP PeptideBlocked or INGAPB is a INGAP Peptide which has been blocked with a N-terminal acetyl group and an C-terminal amide group, in purified, synthetic, or recombinant form.

HIP3Cys (Ile-Gly-Leu-His-Asp-Pro-Thr-Gln-Gly-Thr-Glu-Pro-Asn-Gly-Glu-Cys) (SEQ ID NO: 8)) is a Human proIslet Peptide which has an additional C-terminal cysteine residue, in purified, synthetic or recombinant form.

HIP1Cys (Trp-Ile-Gly-Leu-His-Asp-Pro-Thr-Gln-Gly-Thr-Glu-Pro-Asn-Gly-Cys) (SEQ ID NO: 9)) is a Human proIslet Peptide which has an additional C-terminal cysteine residue, in purified, synthetic or recombinant form.

HIP2Cys (Ile-Gly-Leu-His-Asp-Pro-Thr-Gln-Gly-Thr-Glu-Pro-Asn-Gly-Cys) (SEQ ID NO: 10)) is a Human proIslet Peptide which has an additional C-terminal cysteine residue, in purified, synthetic or recombinant form.

INGAP PeptideCys or INGAPCys is INGAP Peptide which has an additional C-terminal cysteine residue, in purified, synthetic or recombinant form.

HIP3CysDimer (Ile-Gly-Leu-His-Asp-Pro-Thr-Gln-Gly-Thr-Glu-Pro-Asn-Gly-Cys)$_2$ (SEQ ID NO: 11)) is a Human proIslet Peptide dimer wherein each monomer has been modified to include a C-terminal cysteine residue, in purified, synthetic, or recombinant form. The dimer forms via the creation of a disulfide bond between the cysteine residues of the individual monomers.

HIP1CysDimer (Trp-Ile-Gly-Leu-His-Asp-Pro-Thr-Gln-Gly-Thr-Glu-Pro-Asn-Gly-Glu-Cys)$_2$ (SEQ ID NO: 12)) is a Human proIslet Peptide dimer wherein each monomer has been modified to include a C-terminal cysteine residue, in purified, synthetic, or recombinant form. The dimer forms via the creation of a disulfide bond between the cysteine residues of the individual monomers.

HIP2CysDimer (Ile-Gly-Leu-His-Asp-Pro-Thr-Gln-Gly-Thr-Glu-Pro-Asn-Gly-Cys)$_2$ (SEQ ID NO: 13)) is a Human proIslet Peptide dimer wherein each monomer has been modified to include a C-terminal cysteine residue, in purified, synthetic, or recombinant form. The dimer forms via the creation of a disulfide bond between the cysteine residues of the individual monomers. HIP2 has a molecular weight of about 1435.5.

INGAPCysDimer is an INGAP Peptide dimer wherein each monomer has been modified to include a N-terminal cysteine residue, in purified, synthetic, or recombinant form.

HIP3CysBlocked (Ac-Ile-Gly-Leu-His-Asp-Pro-Thr-Gln-Gly-Thr-Glu-Pro-Asn-Gly-Glu-Cys-NH2) (SEQ ID NO: 14)) is a Human proislet Peptide which has been modified to include a C-terminal cysteine residue and has been blocked with a N-terminal acetyl group and a C-terminal amide group, in purified, synthetic, or recombinant form.

HIP1CysBlocked (Ac-Trp-Ile-Gly-Leu-His-Asp-Pro-Thr-Gln-Gly-Thr-Glu-Pro-Asn-Gly-Cys-NH2) (SEQ ID NO: 15)) is a Human proislet Peptide which has been modified to include a C-terminal cysteine residue and has been blocked with a C-terminal acetyl group and a C-terminal amide group, in purified, synthetic, or recombinant form.

HIP2CysBlocked (Ac-Ile-Gly-Leu-His-Asp-Pro-Thr-Gln-Gly-Thr-Glu-Pro-Asn-Gly-Cys-NH2) (SEQ ID NO: 16)) is a Human proIslet Peptide which has been modified to include a C-terminal cysteine residue and has been blocked with a N-terminal acetyl group and a C-terminal amide group, in purified, synthetic, or recombinant form.

INGAPCysBlocked is INGAP Peptide which has been modified to include a C-terminal cysteine residue and has been blocked with a N-terminal acetyl group and a C-terminal amide group, in purified, synthetic, or recombinant form.

HIP3CysBlockedDimer (Ac-Ile-Gly-Leu-His-Asp-Pro-Thr-Gln-Gly-Thr-Glu-Pro-Asn-Gly-Glu-Cys-NH2)$_2$ (SEQ ID NO: 17) is a Human proislet Peptide dimer wherein each monomer has been modified to include a C-terminal cysteine residue and has been blocked with a N-terminal acetyl group and a C-terminal amide group, in purified, synthetic, or recombinant form. The dimer forms via the creation of a disulfide bond between the cysteine residues of the individual monomers.

HIP1CysBlockedDimer (Ac-Trp-Ile-Gly-Leu-His-Asp-Pro-Thr-Gln-Gly-Thr-Glu-Pro-Asn-Gly-Cys-NH2)$_2$ (SEQ ID NO: 18) is a Human proislet Peptide dimer wherein each monomer has been modified to include a C-terminal cysteine residue and has been blocked with a C-terminal acetyl group and a C-terminal amide group, in purified, synthetic, or recombinant form. The dimer forms via the creation of a disulfide bond between the cysteine residues of the individual monomers.

HIP2CysBlockedDimer or HIP2B Cys Dimer (Ac-Ile-Gly-Leu-His-Asp-Pro-Thr-Gln-Gly-Thr-Glu-Pro-Asn-Gly-Cys-NH2)$_2$ (SEQ ID NO:19) is a Human pro Islet Peptide dimer wherein each monomer has been modified to include a C-terminal cysteine residue and has been blocked with a N-terminal acetyl group and an C-terminal amide group, in purified, synthetic, or recombinant form. The dimer forms via the creation of a disulfide bond between the cysteine residues of the individual monomers. HIP2B Cys Dimer has a molecular weight of about 3157.5.

INGAPCysBlocked Dimer is INGAP Peptide dimer wherein each monomer has been modified to include a C-terminal cysteine residue and has been blocked with a N-terminal acetyl group and an C-terminal amide group, in purified, synthetic, or recombinant form. The dimer forms via the creation of a disulfide bond between the cysteine residues of the individual monomers.

HIP3CysPEG (Ile-Gly-Leu-His-Asp-Pro-Thr-Gln-Gly-Thr-Glu-Pro-Asn-Gly-Glu-Cys(PEG)) (SEQ ID NO: 20) is a Human proIslet Peptide which has been modified to include a C-terminal cysteine residue to which has been covalently bonded to a dimeric maleimide activated 40 Kd PEG construct, in purified, synthetic, or recombinant form.

HIP1 CysPEG (Trp-Ile-Gly-Leu-His-Asp-Pro-Thr-Gln-Gly-Thr-Glu-Pro-Asn-Gly-Cys(PEG)) (SEQ ID NO: 21) is a Human proIslet Peptide which has been modified to include a C-terminal cysteine residue to which has been covalently bonded to a dimeric maleimide activated 40 Kd PEG construct, in purified, synthetic, or recombinant form.

HIP2CysPEG (Ile-Gly-Leu-His-Asp-Pro-Thr-Gln-Gly-Thr-Glu-Pro-Asn-Gly-Cys(PEG)) (SEQ ID NO: 22) is a Human proIslet Peptide which has been modified to include a C-terminal cysteine residue to which has been covalently bonded to a dimeric maleimide activated 40 Kd PEG construct, in purified, synthetic, or recombinant form.

INGAPCysPEG is INGAP Peptide which has been modified to include a C-terminal cysteine residue to which has been covalently bonded to a dimeric maleimide activated 40 Kd PEG construct, in purified, synthetic, or recombinant form.

HIP3CysBlockedPEG (Ac-Ile-Gly-Leu-His-Asp-Pro-Thr-Gln-Gly-Thr-Glu-Pro-Asn-Gly-Glu-Cys(PEG)-NH2) (SEQ ID NO: 23) is a Human proIslet Peptide which has been blocked with a N-terminal acetyl group and a C-terminal amide group, and modified to include an C-terminal cysteine residue to which has been covalently bonded to a dimeric maleimide activated 40 Kd PEG construct, in purified, synthetic, or recombinant form.

HIP1CysBlockedPEG (Ac-Trp-Ile-Gly-Leu-His-Asp-Pro-Thr-Gln-Gly-Thr-Glu-Pro-Asn-Gly-Cys(PEG)-NH2) (SEQ ID NO: 24) is a Human proIslet Peptide which has been blocked with a N-terminal acetyl group and a C-terminal amide group, and modified to include an C-terminal cysteine residue to which has been covalently bonded to a dimeric maleimide activated 40 Kd PEG construct, in purified, synthetic, or recombinant form.

HIP2CysBlockedPEG or HIP2B Cys-PEG (Ac-Ile-Gly-Leu-His-Asp-Pro-Thr-Gln-Gly-Thr-Glu-Pro-Asn-Gly-Cys(PEG)-NH2) (SEQ ID NO: 25) is a Human proislet Peptide which has been blocked with a N-terminal acetyl group and a C-terminal amide group, and modified to include an C-terminal cysteine residue to which has been covalently bonded to a dimeric maleimide activated 40 Kd PEG construct, in purified, synthetic, or recombinant form. HIP2B Cys(PEG) has a molecular weight of about 44,782.

INGAPCysBlocked PEG is INGAP Peptide which has been blocked with a C-terminal acetyl group and an N-terminal amide group, and modified to include a C-terminal cysteine residue to which has been covalently bonded to a dimeric maleimide activated 40 Kd PEG construct, in purified, synthetic, or recombinant form.

REG3G is human regenerating islet-derived protein 3 gamma precursor having the sequence MLPPMALPS-VSWMLLSCLILLCQVQ-GEETQKELPSPRISCPKGSKAYGSPCYALFLSPKS WMDADLACQKRPSGKLVSVLSGAEGS-FVSSLVRSISNSYSYIWIGLHDPTQGSEPDGDG WEWSSTDVMNYFAWEKNPSTILNPGH-CGSLSRSTGFLKWKDYNCDAKLPYVCKFKD (SEQ ID NO: 28). REG3G peptide is human regenerating islet-derived protein 3 gamma precursor peptide derived from REG3G having the sequence IGLHDPTQGSEPDG (SEQ ID NO: 29). Other REG3G peptides are WIGLHDPTQGSEPDG (SEQ ID NO: 58) and IGLHDPTQGSEPDGD (SEQ ID NO: 59).

Embodiments of the present disclosure provide detailed strategies for optimizing the stability and solubility of proislet peptides, including HIP, for improved use as a therapeutic agent. HIP is a peptide fragment of the human protein regenerating islet-derived 3 alpha protein (REG3A) (NM_

138937.1), also known as pancreatitis-associated protein precursor (NP-002571) located on chromosome 2, location 2p12 position 79240075 (SEQ ID NO: 1). HIP3, HIP1 and HIP2 induce or stimulate islet neogenesis from progenitor cells resident within the pancreas. These neogenesis agents used in accordance with the methods of the current disclosure result in Optimized forms of proislet peptides, including HIP, which demonstrate increased in vivo stability, solubility and efficacy when used as a therapeutic agent to treat diseases. These diseases include but are not limited to diabetes mellitus (type 1 diabetes), type 2 diabetes (non-insulin dependent diabetes mellitus and insulin requiring adult onset diabetes, diabetes in childhood and adolescence), and Latent Autoimmune Diabetes in Adults (LADA).

Embodiments of the disclosure also provide pharmaceutical compositions and therapies for the treatment of pancreatic dysfunction, including type 1 and type 2 diabetes, with such compositions. In one embodiment, these compositions comprise Optimized proislet peptides, including Optimized HIP. In another embodiment, these compositions include Optimized proislet peptides, including Optimized HIP and other agents that affect glucose metabolism. Included among these other agents are agents that are involved in pancreatic islet neogenesis and agents that inhibit, block, or destroy the autoimmune cells that target pancreatic islet cells. In one embodiment, the therapies disclosed herein are practiced by administering a therapeutically effective dose of Optimized proislet peptides, including Optimized HIP, to a mammal in need of such therapy. In another embodiment, the therapies disclosed herein are practiced by administering a therapeutically effective dose of Optimized proislet peptides, including Optimized HIP, to a mammal in need of such therapy in combination with another agent (such as a hormone or compound) that affects glucose metabolism, including but not limited to hormones or compounds that are involved in beta cell regeneration, satiety, and gastric emptying, such as GLP-1, GIP, GLP-1 receptor analogs, GLP-1 analogs, and Dipeptidyl Peptidase-4 Inhibitors, which prevent destruction of GLP-1, and agents that inhibit, block, or destroy the autoimmune cells that target pancreatic cells. In this latter embodiment, the Optimized HIP and the other agent may be administered separately or may first be admixed to provide a combination composition and administered simultaneously.

Microarray analysis of gene expression in NOD mice has shown the upregulation of the Reg genes specifically in islet neogenesis. In addition, Reg genes have been known to upregulate in late fetal development to populate the pancreas of a developing human to maintain its own glucose metabolism post partum. Co-transplantation of fetal tissue with non-endocrine pancreatic epithelial cells (NEPECs) has been shown to result in stimulation of new islet structures from the NEPEC population. The upregulation of Reg in the co-transplanted fetal material was likely the stimulus for this effect.

In vivo studies have shown that HIP1, HIP2 and HIP3, when introduced into diabetic mice, stimulate differentiation of progenitor cells within the pancreas into new islet structures.

Although effective in the neogenesis of islet structures, there remains the need for optimizing the proislet peptides, including HIP variants, so as to improve their solubility, stability and bioavailability for administration as therapeutic agents. Modifications to the proislet peptides, including HIP variants, that will decrease their chances of protease degradation will increase their efficacy thereby reducing the dosage needed for a positive therapeutic effect. These modifications result in what has been labeled as "Optimized proislet peptides" or "Optimized HIP".

In one embodiment, Optimized proislet peptides, including Optimized HIP, is provided by the present disclosure in purified, synthetic, or recombinant form and is administered in accordance with the methods disclosed herein to induce pancreatic islet neogenesis.

Further, Optimized proislet peptides, including Optimized HIP, may be stably stored for long periods of time. Optimized HIP is stable for months when stored at 20° C. in isotonic saline.

In a specific embodiment, Optimized proislet peptides, including Optimized HIP, is functionally hyperactive, i.e., capable of exhibiting greater activity of one or more of the functional activities associated with REG3A, other HIP peptides, and non-human HIP homologues, such as the hamster INGAP.

Due to the degeneracy of nucleotide coding sequences, a variety of DNA sequences which encode the same or a substantially similar amino acid sequences as Optimized proislet peptides, including Optimized HIP, may be used in the practice of the present disclosure to prepare expression vectors for the production of recombinant Optimized proislet peptides, including Optimized HIP variants. These include, but are not limited to, nucleic acid sequences comprising all or portions of Optimized proislet peptides, including Optimized HIP, that are altered by the substitution of different codons that encode the same or a functionally equivalent amino acid residue within the sequence, thus producing a silent change. The Optimized proislet peptides, including Optimized HIP, and derivatives thereof include, but are not limited to, those containing, as a primary amino acid sequence, all or part of the amino acid sequences of Optimized proislet peptides, including Optimized HIP variants, including altered sequences in which functionally equivalent amino acid residues are substituted for residues within the sequence resulting in a silent change. For example, one or more amino acid residues within the sequence can be substituted by another amino acid of a similar polarity that acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Optimized proislet peptides, including Optimized HIP derivatives, also include, but are not limited to, those containing, as a primary amino acid sequence, all or part of the amino acid sequence of the proislet peptide, including HIP, including altered sequences in which amino acid residues are substituted for residues with similar chemical properties. In a specific embodiment, 1, 2, 3, 4, or 5 amino acids of Optimized HIP are substituted resulting in analogs and/or derivatives of Optimized HIP.

In a specific embodiment, chimeric or fusion proteins may be used in the methods disclosed herein. As used herein, a "chimeric protein" or "fusion protein" comprises Optimized proislet peptides, including Optimized HIP, or an analog or derivative thereof operatively-linked to a non-proislet peptide or HIP polypeptide or an analog or derivative thereof. Within the fusion protein, Optimized proislet peptide or HIP and the non-proislet or HIP polypeptide are "operatively-linked", that is they are fused in-frame with one another. The non-proislet or HIP polypeptide can be fused to the N-terminus or C-terminus of Optimized proislet peptide or HIP. For example, the fusion protein may be Optimized HIP containing a heterologous signal sequence at its N-terminus. In certain host cells (e.g., mammalian host cells), expression and/or secretion of Optimized HIP or an analog or derivative thereof can be increased through use of a heterologous signal sequence. In yet another example, the fusion protein is an Optimized HIP-immunoglobulin fusion protein in which the Optimized HIP sequence is fused to sequences derived from a member of the immunoglobulin protein family. The Optimized HIP-immunoglobulin fusion protein can be incorporated into pharmaceutical compositions and administered to a subject to inhibit an immunological response according to the present disclosure.

Optimized proislet peptides, including Optimized HIP, or an analog or derivative thereof, or an Optimized proislet peptides, including Optimized HIP,-chimeric or fusion protein for use in the methods disclosed herein may be chemically modified for the purpose of improving bioavailability, and/or increasing efficacy, solubility and stability. For example, the protein may be covalently or non-covalently linked to albumin, transferrin or additional polyethylene glycol (PEG) moieties.

Optimized proislet peptides, including Optimized HIP, or an analog or derivative thereof, or an Optimized proislet peptide or HIP-chimeric or fusion protein for use in the methods disclosed herein can be produced by standard recombinant DNA techniques in accordance with the teachings herein and known in the art. For example, DNA fragments coding for the different polypeptide sequences may be ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Furthermore, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence. Moreover, many expression vectors are commercially available that already encode a fusion moiety (e.g., a GST polypeptide). An Optimized HIP-encoding nucleic acid can be cloned into such an expression vector such that the fusion moiety is linked in-frame to Optimized HIP. The fusion protein can be an Optimized HIP fused to a His tag or epitope tag (e.g. V5) to aid in the purification and detection of the recombinant Optimized HIP, or to mask the immune response in a subject. The short amino acid sequences of Optimized HIP and its analogs and derivatives make synthetic production of these valuable peptides readily practicable as well, and a variety of automated instruments for peptide synthesis are commercially available, and synthetic methods for peptide synthesis not requiring automation have long been known and can be used in accordance with the teachings herein to prepare Optimized HIP or an analog or derivative thereof.

In some embodiments, Optimized proislet peptides, including Optimized HIP, or an analog or derivative thereof, or an Optimized proislet peptide or HIP-chimeric or fusion protein can be modified so that it has an extended half-life in vivo using any methods known in the art. For example, the Fc fragment of human IgG or inert polymer molecules such as high molecular weight polyethyleneglycol (PEG) can be attached to Optimized HIP or an analog or derivative thereof with or without a multifunctional linker either through site-specific conjugation of the PEG to the N- or C-terminus of the protein or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to Optimized HIP or an analog or derivative thereof. Unreacted PEG can be separated from Optimized HIP-PEG conjugates by size-exclusion or by ion-exchange chromatography. PEG-derivatized conjugates can be tested for in vivo efficacy using methods known to those of skill in the art.

Embodiments of the present disclosure provide Optimized proislet peptide formulations, including Optimized HIP formulations, and Optimized proislet or HIP-based therapies and methods for delivery of Optimized proislet peptide or HIP variants in the treatment of diabetes and the various other indications involving impaired pancreatic function.

In one embodiment, a proislet peptide is optimized by the addition of a C-terminal amide group and a N-terminal acetyl group thereby effectively blocking proteolytic activity by those proteases that recognize and degrade free ends of peptides in serum and resulting in the Optimized proislet peptide compounds.

In one embodiment, HIP3, HIP1 and/or HIP2 is optimized by the addition of a C-terminal amide group and a N-terminal acetyl group thereby effectively blocking proteolytic activity by those proteases that recognize and degrade free ends of peptides in serum and resulting in the Optimized HIP compounds HIP3Blocked (SEQ ID NO: 5), HIP1Blocked (SEQ ID NO: 6) and HIP2Blocked (SEQ ID NO: 7), respectively. These blocking groups are added by were prepared by Solid Phase Peptide Synthesis (SPPS). The fundamental premise of solid phase synthesis is that amino acids can be assembled into a peptide of any desired sequence while one end of the chain is anchored to an insoluble support. As mentioned above, in practical SPPS the carboxyl terminus of the peptide is linked to the polymer. After the desired sequence of amino acids has been linked together on the support, a reagent can be applied to cleave the peptide chain from the support and liberate the crude peptide into solution. All the reactions involved in the synthesis are carried to completion if possible, so that a homogeneous product could be obtained.

When the C-terminal of a peptide is an amide the derivative is a peptide amide. Peptide-amides are extremely important derivatives since many naturally occurring peptide hormones are present as the amide. To synthesize peptide amides solid phase resins have been developed which yield peptide amides directly upon cleavage. When the N-terminal is an acetyl group, the peptide is assembled from the C-terminal to the N-terminal. The N-terminal is then acetylated using acetic anhydride in the presence of a base.

In another embodiment proislet peptides are modified by the addition of a C-terminal cysteine residue resulting in the Cys proislet peptide compounds. These Optimized proislet peptide compounds are capable of forming dimers in solution wherein a disulfide bond is formed between the cysteines of the individual monomers resulting in the Optimized proislet peptide compounds proislet peptide CysDimer.

In another embodiment HIP3, HIP1 and/or HIP2 are modified by the addition of a C-terminal cysteine residue resulting in the Optimized HIP compounds HIP3Cys (SEQ ID NO: 8), HIP1Cys (SEQ ID NO: 9) and HIP2Cys (SEQ ID NO: 10), respectively. These Optimized HIP compounds are capable of forming dimers in solution wherein a disulfide bond is formed between the cysteines of the individual monomers resulting in the Optimized HIP compounds HIP3CysDimer (SEQ ID NO: 11), HIP1CysDimer (SEQ ID NO: 12) and HIP2CysDimer (SEQ ID NO: 13), respectively. The cysteine residue is added by which 4 grams of crude peptide was wet with 2 ml acetic acid and diluted with ~500 ml DI water, then pH was adjusted to ~8.2 by adding 20% NH$_4$OH solution dropwise and allowed to stir overnight at room temperature. Reaction was not completed overnight, hence added potassium ferrycyanide solution until a permanent yellowish green color persisted. At this stage reaction was complete as determined by Ellman test and HPLC analysis. The oxidation solution was then treated with a spatula of AG-1×2 (chloride form) resin for 30 minutes and filtered on a P4 funnel and finally pH was adjusted to ~5 prior to HPLC purification.

In another embodiment the Cys prisolet peptides are blocked by the addition of a C-terminal amide group and a N-terminal acetyl group thereby protecting the compound from degradation by proteases that recognize free ends in serum and resulting in the Optimized HIP compounds proislet peptide CysBlocked. Additionally, these compounds are capable of forming dimers in solution wherein a disulfide bond is formed between the cysteines of the individual monomers resulting in the Optimized proislet compounds proislet peptide CysBlockedDimer. These blocking groups are added as discussed above.

In another embodiment HIP3Cys (SEQ ID NO: 8), HIP1Cys (SEQ ID NO: 9) and/or HIP2Cys (SEQ ID NO: 10) are blocked by the addition of a C-terminal amide group and a N-terminal acetyl group thereby protecting the compound from degradation by proteases that recognize free ends in serum and resulting in the Optimized HIP compounds HIP3CysBlocked (SEQ ID NO: 14), HIP1CysBlocked (SEQ ID NO: 15) and HIP2CysBlocked (SEQ ID NO: 16), respectively. Additionally, these compounds are capable of forming dimers in solution wherein a disulfide bond is formed between the cysteines of the individual monomers resulting in the Optimized HIP compounds HIP3CysBlockedDimer (SEQ ID NO: 17), HIP1CysBlockedDimer (SEQ ID NO: 18) and HIP2CysBlockedDimer (SEQ ID NO: 19), respectively. These blocking groups are added as discussed above.

In another embodiment the Cys proislet peptideare optimized by covalently binding a dimeric maleimide activated 40 Kd PEG construct to the C-terminal cysteine residue resulting in the Optimized HIP compounds proislet peptide CysPEG. The PEG construct may be covalently bound to the C-terminal cysteine residue by having the monomeric purified form of CS504 peptide (1.1 equivalent) dissolved in acetate buffer (pH=6.5). A solution of PEG maleimide (1 equivalent) can prepared in DI water and added to the peptide solution with stirring. The pH of the resulting solution can be again adjusted to ~6.5 with dilute NH$_4$OH solution, stirred at room temperature for 30 minutes and acidified with few drops of acetic acid and finally purified by RP-HPLC.

In another embodiment HIP3Cys (SEQ ID NO: 8), HIP1Cys (SEQ ID NO: 9) and/or HIP2Cys (SEQ ID NO: 10) are optimized by covalently binding a dimeric maleimide activated 40 Kd PEG construct to the C-terminal cysteine residue resulting in the Optimized HIP compounds HIP3CysPEG (SEQ ID NO: 20), HIP1CysPEG (SEQ ID NO: 21) and HIP2CysPEG (SEQ ID NO: 22), respectively. The PEG construct is covalently bound to the C-terminal cysteine residue by having the monomeric purified form of CS504 peptide (1.1 equivalent) dissolved in acetate buffer (pH=6.5). A solution of PEG maleimide (1 equivalent) was prepared in DI water and added to the peptide solution with stirring. The pH of the resulting solution was again adjusted to ~6.5 with dilute NH$_4$OH solution, stirred at room temperature for 30 minutes and acidified with few drops of acetic acid and finally purified by RP-HPLC.

In another embodiment proislet peptide CysPEG are optimized by the addition of a C-terminal amide group and a N-terminal acetyl group thereby protecting the compound from degradation by proteases that recognize free ends in serum and resulting in the Optimized HIP compounds proislet peptide CysPEGBlocked. The blocking groups are added as discussed above.

In another embodiment HIP3CysPEG (SEQ ID NO: 20), HIP1CysPEG (SEQ ID NO: 21) and HIP2CysPEG (SEQ ID NO: 22) are optimized by the addition of a C-terminal amide group and a N-terminal acetyl group thereby protecting the compound from degradation by proteases that recognize free ends in serum and resulting in the Optimized HIP compounds HIP3CysPEGBlocked (SEQ ID NO: 23), HIP1CysPEGBlocked (SEQ ID NO: 24) and HIP2CysPEGBlocked (SEQ ID NO: 25), respectively. The blocking groups are added as discussed above.

The Optimized proislet peptide or HIP or analog or derivative therapies or combination therapies of the present disclosure can be used to treat any mammal, including humans and animals, suffering from a disease, symptom, or condition related to a diminished production or secretion of insulin due to the loss of or diminished beta cell function or the need for greater insulin production than can be provided to the subject via differentiation of new islet structures from progenitor cells utilizing Optimized HIP compounds and methods of treatment. Such diseases and conditions include type 1 diabetes mellitus, type 2 diabetes, pre-diabetes, impaired fasting glucose, fasting hyperinsulinemia, including but not limited to patients with type 1a diabetes patients or patients with Latent Autoimmune Diabetes of Adulthood who may manifest antibodies (anti-GAD65 antibodies, anti-islet antibodies, or anti-insulin antibodies) or those patients with type 1 diabetes with insulin deficiency without autoimmunity directed toward the beta cells (type 1b diabetes). Moreover, embodiments of the present disclosure can be practiced with therapeutic benefit for patients newly diagnosed as having type 1 diabetes, the siblings and first degree relatives of patients with type 1 diabetes, and people with positive antibodies and other autoimmune conditions that indicate a predilection to type 1 diabetes. In one embodiment, the methods disclosed herein are practiced to reverse type 1 diabetes in a patient in need of such treatment.

The combination therapies and related methods and compositions can also be employed as adjunctive therapy to insulin therapy in type 1 diabetes in children and adults, to ameliorate glucose swings in patients with diabetes, and in patients with poorly controlled diabetes, hypoglycemic unawareness, and recurrent hypoglycemia in type 1 diabetes.

The Optimized proislet peptide or HIP or analog or derivative therapies and related methods and compositions can be used to treat patients having newly diagnosed type 2 diabetes, type 2 diabetes in children and adults with hyperglycemia, type 2 diabetes being concurrently treated with insulin, oral diabetic or other subcutaneous diabetic therapies, and poorly controlled type 2 diabetes. In some patients, both children and adults, the methods and compositions disclosed herein can reverse type 1 and 2 diabetes. The methods and compositions disclosed herein can also be used to treat both children and adults having atypical forms of diabetes and patients having the conditions of postprandial hyperglycemia.

The Optimized proislet peptide or HIP or analog or derivative therapies and related methods and compositions can also be used to treat patients who are children, as well, as adult patients, in need of weight loss, reduction in triglycerides, LDL cholesterol, including but not limited to achieve weight loss or treat obesity, overweight in patients having diabetes as well as those who do not have type 1 or 2 diabetes. In one embodiment, the methods and compositions disclosed herein are used to treat a patient having morbid obesity. In other embodiments, the methods and compositions disclosed herein are used to treat a patient having morbid obesity or patients having anorexia, bulimia, or other eating disorders.

The single agent Optimized therapies and related methods and compositions can also be used to treat children and adults having dysmetabolic syndrome or metabolic syndrome, as well as patients exhibiting the conditions of neuropathic pain syndromes secondary to altered glucose metabolism, and those with hypertriglyceridemia with and without diabetes, and postprandial hypertriglyceridemia. In one embodiment, these methods are practiced to treat polycystic ovarian syndrome in a patient in need of such treatment.

Other patients that can benefit from the Optimized proislet peptide or HIP or analog or derivative therapies and related methods include children and adult patients diagnosed as having conditions such as fasting hyperglycemia, pre-diabetes, impaired fasting glucose, impaired glucose tolerance, and hyperglycemic conditions generally.

The Optimized proislet peptide or HIP or analog or derivative therapies and related methods and compositions can also be used to treat patients having neuropathic pain syndromes and neuropathy, regardless of whether the patient is diagnosed as diabetic.

The Optimized proislet peptide or HIP or analog or derivative therapies and related methods and compositions can also be used to treat patients having recurrent pancreatitis or pancreatic cancer and can be used in all modalities aimed at achieving new islet structures derived from progenitor cells in the pancreas.

In one embodiment, the agent that stimulates islet differentiation from pancreatic progenitor cells into insulin producing islet structures is selected from Optimized proislet peptide or HIP or an analog or derivative thereof. In another embodiment, a combination of Optimized proislet peptide, including HIP, and another agent to stimulate islet cell neogenesis. This additional agent can be, for example, amylin and/or an analog, including but not limited to Pramlintide (SYMLIN™), GLP-1 receptor analogs, exendin-4 (EXENATIDE™), Liraglutide (NN2211), GLP-1, GLP-1 analogs GIP, GLP-1, hamster INGAP, other incretin-mimetic hormones, and/or similarly acting compounds and agents, and agents that extend the half-life or increase the level or activity of any of the foregoing compounds and agents, such as, for example, dipeptidyl peptidase-4 inhibitors, which delay the degradation of GLP-1. There are numerous GLP-1 mimetics that act via direct agonist activity on the GLP-1 receptors or by inhibiting the degradation of GLP-1. These agents are useful in certain embodiments of the present disclosure. GLP-1 mimetics can be used in conjunction with HIP and/or targeted immune therapy for the treatment of type 1 diabetes, and, they can be used to improve glycemic control, increase satiety, delay gut glucose absorption and lead to a reversal of the underlying mechanisms resulting in type 1 diabetes. These agents and methods may prevent progression of impaired glucose tolerance in diabetes; to prevent pre-diabetes, progression of impaired fasting glucose to impaired glucose tolerance and diabetes; to reverse newly diagnosed type 2 diabetes; to treat type 2 diabetes, and to treat or prevent overweight, obesity, polycystic ovarian syndrome, and neuropathic pain syndromes.

Methods, agents, and pharmaceutical formulations useful in the practice of the present disclosure to achieve pancreatic islet differentiation from progenitor cells in the adult pancreas and include those described for other purposes in the following references, each of which is incorporated herein by reference: Rosenberg et al., 1992, *Adv. Exp. Med. Biol.* 321: 95-104; March 1996, *Diabetologia* 39(3):256-62; July 1996, *Pancreas* 13(1):38-46; and November 2004, *Ann. Surg.* 240 (5):875-84; Vinik et al., June 1997, *Horm. Metab. Res.* 29(6): 278-93. The successful stimulation of islet regeneration or differentiation of pancreatic progenitor cells can be shown through the increased production and/or secretion of insulin in a subject.

In one embodiment, amylin or an analog of amylin such as Symlin™ or Pramlintide is employed prior to administration or in concomitant administration with Optimized HIP. Amylin may be administered prior to islet regeneration and continued through the islet regeneration period administration in accordance with the teachings of the reference Young et al., 1997, *Curr. Opin. Endocrin. Diabetes* 4: 282-290, incorporated herein by reference. In one embodiment, amylin and/or an analog, including but not limited to pramlintide, is administered subcutaneously to optimize glycemic control prior to the initiation of Optimized HIP and may then be and used alone or in conjunction with other islet stimulating peptides, such as Optimized HIP or a Optimized HIP analog or derivative. In one embodiment, amylin or pramlintide is dosed at 0.3-0.8 micrograms per kilogram patient weight. In one embodiment, this dose is administered subcutaneously before meals, for example, QHS and 3 AM. In one embodiment, the therapeutically effective dose is delivered subcutaneously or via an infusion device/pump and/or a transdermal, intranasal, buccal, microneedle delivery system, oral encapsulation method. In another embodiment, the therapeutically effective dose is administered utilizing sustained release formulations requiring administration by injection or other delivery method no more frequently than once a week, once every 2 weeks, or once monthly. As noted above, in some embodiments, amylin or pramlintide is co-administered with another islet stimulating agent.

In one embodiment, a GLP-1 receptor analog, including exendin-4 or an analog of exendin 4 is employed in the method with Optimized HIP at doses of 5-10 mcg with meals. Exendin-4 can be formulated and administered for purposes of the present disclosure in accordance with the teachings of the following references, each of which is incorporated herein by reference: Alcantara et al., 1998, *Cell Biochem. Funct.* 16(1): 51-6; Dupre et al., 2004, *J. Clin. Endocrin. Metab.* 89(7): 3469-73; Edwards et al., 1999, *Diabetes* 48: 86-93; and Xu et al., 1999, *Diabetes* 48: 2270-76. In one embodiment, exendin-4 is dosed in the range of 5-10 micrograms before meals. In one embodiment, exendin-4 is administered subcutaneously alone or in conjunction with Optimized HIP and/or other islet stimulating peptides. In one embodiment, the therapeutically effective dose is administered subcutaneously. In another embodiment, delivery of exendin-4 is via transdermal, buccal, oral encapsulation methods, intranasal or microneedle delivery systems. In another embodiment, the therapeutically effective dose is contained in a sustained release formulation that requires administration no more frequently than once a week, once every 2 weeks, or once monthly. In one embodiment, exendin-4 is co-administered with Optimized HIP or another islet cell neogenesis or progenitor cell transformation agent among patients with type 1 or 2 diabetes, or those with obesity, overweight, insulin resistant syndrome, impaired fasting glucose, pre-diabetes, polycystic ovarian syndrome, the metabolic syndrome or eating disorders.

GIP and GLP-1 belong to the incretin family of growth hormones (see the references Creutzfeldt, 1979, *Diabetologia* 16: 75-85; Creutzfeldt and Ebert, 1985, *Diabetologia* 28:

565-573; Hoist et al., 2001, *Scand. J. Clin. Lab. Invest. Suppl.* 234: 75-85; and Vilsboll et al., June 2003, *J. Clin. Endocrin. Metab.* 88(6):2706-13, each of which is incorporated herein by reference), and in one embodiment, an incretin hormone or analog with or without the concomitant usage of Optimized HIP is employed in the method to stimulate differentiation to islets from progenitor cells in the adult pancreas.

In various embodiments, GIP or a GIP analog is employed with Optimized proislet peptide, including HIP. GIP can be formulated and administered for purposes of the present disclosure in accordance with the teachings of the following references, each of which is incorporated herein by reference: Andersen et al., 1978, *J. Clin. Invest.* 62: 152-161; Creutzfeldt et al., February 1980, *Diabetes* 29(2):140-5; Dupre et al., 1973, *J. Clin. Endocrin. Metab.* 37: 826-828; Ebert et al., 1980, *Clinical Gastroenterology* 9(3): 679-98; Elahi et al., 1979, *Am. J. Physiol.* 237: E185-E191, and 1994, *Regulatory Peptide* 51(1): 63-74; Krarup et al., June 1983, *J. Clin. Endocrin. Metab.* 56(6):1306-12; Krarup et al., 1987, *Metabolism* 36(7): 677-82; Krarup et al., 1988, *Acta Med. Scand.* 223(5): 437-41; Lynn et al., 2003, *FASEB* 17:19-93; Meir et al., 2002, Regulatory Peptides 107:1-3; and Nauk et al., 1993, *J. Clin. Endocrin. Metab.* 76(4): 912-7.

In one embodiment, GIP is administered intravenously or subcutaneously in combination with Optimized proislet peptide, including HIP, or an analog or derivative thereof and dosed at 2-10 nanograms per kilogram patient weight to provide a 30-minute continuous infusion by either intravenous or subcutaneous delivery time beginning 3-5 minutes before meals, before bedtime, and beginning at 3 AM. In one embodiment GIP is administered subcutaneously before meals, QHS, and 3AM. In one embodiment, GIP is administered orally or using an infusion device or a transdermal, buccal, intranasal or microneedle delivery systems. In another embodiment, a sustained release formulation requiring administration no more frequently than once every week, once every 2 weeks, or once monthly injections is employed. Suitable compositions for administering GIP in accordance with the methods disclosed herein are described for other purposes in the reference Jones et al., 6 Nov. 1989, *Diabetes Res. Clin. Pract.* 7(4):263-9.

In various embodiments, GLP-1 or an analog, or a GLP-1 receptor agonist or a Dipeptidyl Peptidase-4 Inhibitor is employed in combination with Optimized proislet peptide, including HIP, or an analog or derivative thereof, in the method to stimulate islet differentiation from progenitor cells, GLP-1, GLP-1 receptor agonists, GLP-1 analogs and DPP-4 inhibitors can be formulated and administered for purposes of the present disclosure in accordance with the teachings of the following references, each of which is incorporated herein by reference: Elahi et al., 1994, *Regulatory Peptides* 51(1): 63-74; Gutniak et al., 1994, *Diabetes Care* 17:1039-44; Kreymann et al., 1987, *Lancet* 2: 1300-1304; Larsen et al., 1996, *Diabetes* 45(Suppl. 2):233A (Abstract); Larsen et al., 2001, *Diabetes Care* 24(8): 1416-21; List et al., 2004, *Am. J. Physiol. Endocrin. Metab.* 286(6): E875-81; Lugari et al., 2000, *Horm. Metab. Res.* 32: 424-428; Marquez et al., March 1998, *Cell. Biochem. Funct.* 16(1):51-6; Meier et al., March 2004, *Critical Care Medicine* 32(3):848-851; Meneilly et al., 2003, *Diabetes Care* 26: 2835-41; Nauk et al., 1996, *Diabetologia* 39(12):1546-53; Thorens et al., December 1995, *Diabetes Metab.* 21(5):311-8; Vilsboll et al., 2003, *J. Clin. Endocrin. Metab.* 88(6): 2706-13; Wang et al., 1997, *J. Clin. Invest.* 99: 2883-2889; and Zander et al., 2002, *Lancet* 359: 824-30.

In various embodiments, GLP-1, a GLP-1 receptor agonist, or a GLP-1 analog is administered subcutaneously or DPP-4 inhibitors are given orally in combination with Optimized proislet peptide, including HIP, or an analog or derivative thereof and dosed in the range of 400-800 mg per day at 8-20 mg per kilogram patient weight. In one embodiment GLP-1 is administered orally or subcutaneously before meals, QHS. In one embodiment, GLP-1 is administered using a continuous subcutaneous infusion device at a rate of 1-30 ng/kilogram body weight/minute or a transdermal, buccal, or microneedle delivery system to provide a 30-minute continuous infusion by either intravenous or subcutaneous delivery time beginning 3-5 minutes before meals, before bedtime, and beginning at 3 AM. In another embodiment, a sustained release formulation requiring administration no more frequently than once every week, once every 2 weeks, or once monthly injections is employed.

In one embodiment, liraglutide (NN2211) is administered subcutaneously in combination with Optimized proislet peptide, including HIP, or an analog or derivative thereof in doses of 10-40 micrograms per kilogram body weight. In another embodiment liraglutide is administered subcutaneously before meals, QHS, and 3AM. In another embodiment, liraglutide is administered using an infusion device or a transdermal, buccal, or microneedle delivery system to provide a 30-minute continuous infusion by either intravenous or subcutaneous delivery time beginning 3-5 minutes before meals, before bedtime, and beginning at 3 AM. In another embodiment, a sustained release formulation requiring administration no more frequently than once every week, once every 2 weeks, or once monthly injections is employed.

In one embodiment of the combination therapies, liraglutide or NN2211 is administered at a dose of about 20 micrograms per kg of patient weight daily in combination with Optimized proislet peptide, including HIP. This dose will provide patients the ability to reduce bolus insulin before meals by 10-20% with reduced fluctuations and decreased postprandial glucose, glucagon, and triglycerides. Administration of liraglutide in accordance with the methods disclosed herein can be used to improve glycemic control, as measured, for example and without limitation, by hemoglobin A 1C, in type 1 diabetes; to prevent progression of impaired glucose tolerance in diabetes; to prevent progression of impaired fasting glucose to impaired glucose tolerance and diabetes; to reverse newly diagnosed type 2 diabetes; and to treat type 2 diabetes.

In an embodiment of the combination therapy, liraglutide or NN2211 is administered at a dose of about 20 micrograms per kg of patient weight to an adult patient in the morning, about 4 hours before food intake, and at bedtime for three consecutive weeks during Optimized proislet peptide or HIP therapy. For patients initiating treatment with C-peptide levels lower than about 1.0 ng/mL, C-peptide levels are monitored, and when they rise above 0.5 ng/mL, the antibody hOKT3g1 (ala-ala) is administered for 12 consecutive days.

In the combination therapies, exendin-4 or synthetic exendin-4 or another GLP-1 analog, GLP-1 receptor agonist, or Dipeptidyl Peptidase-4 Inhibibtor is administered prior to meals alone or with Optimized proislet peptide or HIP or another islet differentiation agent to improve glycemic control prior to or during the initiation of Optimized HIP therapies. Such agents, when delivered prior to meals may result in a reduction in the need for insulin of at least 20% and appropriate tapering of insulin and diabetic medications will be conducted while Optimized HIP is administered. As Optimized HIP and/or other agents are delivered in both type 1 and type 2 patients, careful tapering of insulin and other diabetes medications will take place to protect against hypoglycemia as new islet cells are differentiated from progenitor cells.

Ultimately, insulin and diabetes medications, including Optimized HIP, will be tapered off, as the pancreas is repopulated with new functional islets. For patients initiating treatment with C-peptide levels lower than about 1.0 ng/mL, C-peptide levels are monitored, and when they rise above 0.5 ng/mL, careful monitoring and tapering of exogenous insulin doses will occur.

Among patients with type 1 diabetes, prior to initiation of Optimized proislet peptide, including HIP, and/or other peptide compounds (SYMLIN™, hamster INGAP, GLP-1, GLP-1 receptor agonists, GLP-1 analogs, DPP-4 inhibitors are used with (preceding, during, or following) immune therapy will be administered to protect newly formed islets. For example, the antibody hOKT3g1 (ala-ala) is administered for 12 consecutive days with its efficacy demonstrated following the first treatment out to 24 months, whereas a similar humanized monoclonal antibody, ChAglyCD3 may be administered for 6 consecutive days, then repeated yearly. Diamyd's GAD65 compound is delivered in two subcutaneous injections, one month apart. DIAPEP277™, a heat shock protein 60, has demonstrated success among newly diagnosed diabetes patients utilizing a subcutaneous injections of 1 mg with 40 mg mannitol in vegetable oil at study entry, 1 month, and 6 months. Based upon the immune modulator selected, the cyclicity of treatment will be determined. In another embodiment, DIAPEP277™, a heat shock protein 60 vaccine, and IBC-VSO vaccine, which is a synthetic, metabolically inactive form of insulin designed to prevent pancreatic beta-cell destruction, interferon-alpha, or vaccination using $CD4^+CD25^+$ antigen-specific regulatory T cells or a similar agent is used in the combination therapy. In another embodiment, immunomodulation agents, including, but not limited to, anti-CD3 immunotherapy agents and polyclonal Anti-T-lymphocyte globulin, are used in combination with Optimized HIP. Such agents also include: Sirolimus (Rapamycin), Tacrolimus (FK506), a heat-shock protein 60 (DIAPEP277™), anti-Glutamic Acid Decarboxylase65 (GAD65) vaccine, Mycophenolate Mofetil alone or in combination with Daclizumab, the anti-CD20 agent Rituximab, Campath-1H (Anti-CD52 Antibody) and/or Vitamin D.

Some autoimmune cells target pancreatic beta cells and so play a causative role in some of the diseases and conditions treatable in accordance with the methods disclosed herein. See the references Bach et al., 2001, *Ann. Rev. Immun.* 19: 131-161; Lernmark et al., *Endocrin. Metab. Clin. N. Am.* 20(3): 589-617; and Mathis et al., December 2001, *Nature* 414(6865): 792-798, each of which is incorporated herein by reference.

Prior methods of treatment involving the introduction of immune agents among patients with type 1 diabetes, protect only those islet cells which have yet been destroyed by immune attack and do not address to need to repopulate the pancreas with new islet structures with fully functionally beta cells. These methods combine generalized and specific immune modulation aimed at reducing destruction of beta cells and a methodology of differentiating new islet cells from progenitor cells within the adult pancreas.

The methods of the present disclosure may employ agents that specifically inhibit the activity of or block or destroy the autoimmune cells that target pancreatic beta cells that produce insulin, amylin, or glucagon. Such agents include immunomodulatory peptides that arrest pancreatic islet cell destruction. For example, one such agent is a monoclonal antibody that can delay the progression of islet cell loss or slow or stop the onset of type 1 diabetes. Anti-CD3 antibodies constitute a general class of agents useful in the methods disclosed herein. For example, suitable anti-CD3 antibodies for purposes of the present disclosure include the TRX4 (Ala-Ala and ChAglyCD3) antibody under development by TolerRx and the humanized anti-CD3 antibody described in the reference Herold et al., 30 May 2002, *NEJM* 346(22):1692-1698, incorporated herein by reference. In one embodiment, the humanized anti-CD3 antibody is delivered intravenously, 14 days per year in the dosage of 1-1.42 μg/kg on day 1, 5.67 μg/kg on day 2, 11.3 μg/kg on day 3, 22.6 μg/kg on day 4 and 45.4 μg/kg on days 5-14. These therapies may be repeated annually following the 3-6 month usage of Optimized HIP, while insulin is being tapered as new islet cell formation occurs. During the Optimized HIP treatment phase, Vitamin D and the usage of Pramlintide/Symlin™ may be continued. Following the discontinuation of Optimized proislet peptide, including HIP, and insulin therapy, immune modulation may be repeated annually for the anti-CD3 antibodies, though recent study has found their efficacy to continue for as long as 24 months.

In another embodiment, the immuno-modulatory compound is a heat shock protein that can arrest or slow islet cell destruction. Such proteins include DIAPEP277™, a heat-shock protein under development by Develogen AG. In one embodiment, DIAPEP277™ is delivered subcutaneously by giving 1 mg in 40 mg mannitol in vegetable oil subcutaneously at baseline and at one month and then twice at 3 month intervals. In one embodiment of the combination therapy, Optimized proislet peptide, including HIP, or a Optimized HIP analog or derivative is co-administered with DIAPEP277™ as follows. The DIAPEP277™ is first administered subcutaneously at a dose of about 1 mg, about 30 days prior to the initiation of the Optimized proislet peptide, including HIP, or analog or derivative-based therapy. A second administration of the DIAPEP277™ is then made at the time (90 days after the first administration) of initiating the Optimized HIP or analog or derivative-based therapy.

In another embodiment, the immuno-modulatory compound is Polyclonal Anti-T-Lymphocyte Globulin (ATG). Four dosages of ATG doses are given. The first dosage of ATG is 9 mg/kg of body weight, then 3 consecutive doses of 3 mg/kg) will be administered intravenously over 4 hours. One hour before the first ATG administration, a cutaneous tolerance test (0.2 ml of the final solution) will be performed. In one embodiment of the combination therapy, ATG is delivered prior to the usage of Optimized HIP or a Optimized HIP analog or derivative. The last dosage of ATG is delivered a minimum of 14 days prior to the initiation of the Optimized HIP or analog or derivative-based therapy. A second administration of the ATG may be required based on quarterly measurements of anti-GAD65 antibodies and other immune markers suggesting autoimmune attack at 24 months after the initial treatment with ATG. Earlier treatment may be required if there is a significant rise in autoimmune antibodies directed toward the pancreas.

The Optimized proislet peptide, including HIP, or analog or derivative thereof may be delivered via subcutaneous injection, orally via hepatic targeted vesicle, or other liposomal agent, or via 24 hour continuous subcutaneous infusion at a therapeutically effective dose, as described above. In one embodiment, the daily dose is about 5 to 20 mg per kg of patient body weight per 24 hours. In one embodiment, the daily dose is ~600-800 mg. The Optimized proislet peptide or analog or derivative-based therapy is continued for a 3-6 month period and monitored closely by C-peptide production. The immune therapy will be delivered cyclically based upon the immune agent selected. For example, the DIAPEP277™ is administered at 3 month intervals for a total of 6 months, and would initially be delivered 3 months prior to Optimized HIP or analog or derivative-based therapy.

The immuno-modulatory agents useful in the methods disclosed herein can be formulated, administered, and dosed as known in the art or as described herein. Pharmaceutical formulations and additional dosing and administration protocols for practice of the methods disclosed herein are described below.

Compositions of Optimized proislet peptide, including HIP, or an analog or derivative thereof, e.g., and pharmaceutically acceptable salts and esters thereof are synergistically or additively effective to differentiate progenitor cells into new islet cells in treating diabetes or a similar disorders when combined with various other compounds. These compounds include Optimized proislet peptide, including HIP, and analogs or derivatives thereof, amylin and/or an analog, including but not limited to Symlin/Pramlintide, GLP-1, GLP-1 receptor agonists, such as exendin-4, Liraglutide (NN2211), GLP-1 analogs, Dipeptidyl Peptidase-4 Inhibitors, GIP, hamster INGAP, and other incretin-mimetic hormones, and/or similarly acting compounds and agents, and agents that extend the half-life or increase the level or activity of any of the foregoing compounds and agents, such as, for example, dipeptidyl peptidase inhibitors, which delay the degradation of GLP-1, and agents that inhibit, block, or destroy the autoimmune cells that target beta cells including but not limited to: anti CD-3 antibodies, including hOKT31 (Ala-Ala) and ChAglyCD3, ATG, Sirolimus (Rapamycin), Tacrolimus (FK506), a heat-shock protein 60 (DIAPEP277™) a anti-Glutamic Acid Decarboxylase 65 (GAD65) vaccine, Mycophenolate Mofetil alone or in combination with Daclizumab, the anti-CD20 agent Rituximab, Campath-1H (Anti-CD52 Antibody), lysofylline, and Vitamin D, IBC-VSO vaccine which is a synthetic, metabolically inactive form of insulin designed to prevent pancreatic beta-cell destruction, and interferon-α vaccination using $CD4^+CD25^+$ antigen-specific regulatory T cells or a similar agent designed to prevent pancreatic beta-cell destruction. In this last embodiment, interferon-α vaccination using $CD4^+CD25^+$ antigen-specific regulatory T cells or a similar agent is used in the combination therapy for utilizing regulatory T cells either directly or through the use of anti-CD3 immunotherapy.

Compounds such as Sirolimus (Rapamycin), Tacrolimus (FK506), TRX4 antibody, humanized anti-CD3 antibody, DYAMID™ anti-GAD65 antibody, and DIAPEP277™ are also synergistically or additively effective when added to usage of Optimized HIP or an agent to differentiate progenitor cells into new islet cells in treating diabetes or a similar disorders.

An improvement in a drug therapeutic regimen can be obtained by the combined administration of two agents having therapeutic effect, if the interaction of the two or more agents is such that their combined effect reduces the incidence of adverse event (AE) of either or both agents used in the co-therapy. This reduction in the incidence of adverse effects can be a result of, e.g., administration of lower doses of either or both agent used in the co-therapy. For example, if the effect of drug A alone is 25% and has an adverse event incidence of 45% when used at the labeled dose; and the effect of drug B alone is 25% and has an adverse event incidence of 30% when used at the labeled dose, but when the two drugs are combined at lower than labeled doses of each, if the overall effect is 35% and the adverse incidence rate is 20%, there is an improvement in the drug therapeutic regimen. The combination therapies provided by the present disclosure include those exhibiting such improvements.

Pharmaceutical Compositions, Dosing and Administration

In preferred embodiments, Optimized proislet peptides, including HIP, are delivered in a concentration about 0.5 to about 5 mg/kg/day, more preferably in divided subcutaneous injections in humans. Thus a 60 kg individual would potentially receive 60 mg/day divided into two to three, 20 mg dosages delivered after meals. In other preferred embodiments, Optimized proislet peptides, including HIP, may also be delivered via an oral encapsulation method with dosages in the range of about 0.5 to about 5 mg/kg/day, preferably delivered orally in divided dosages after meals.

Figure 23:
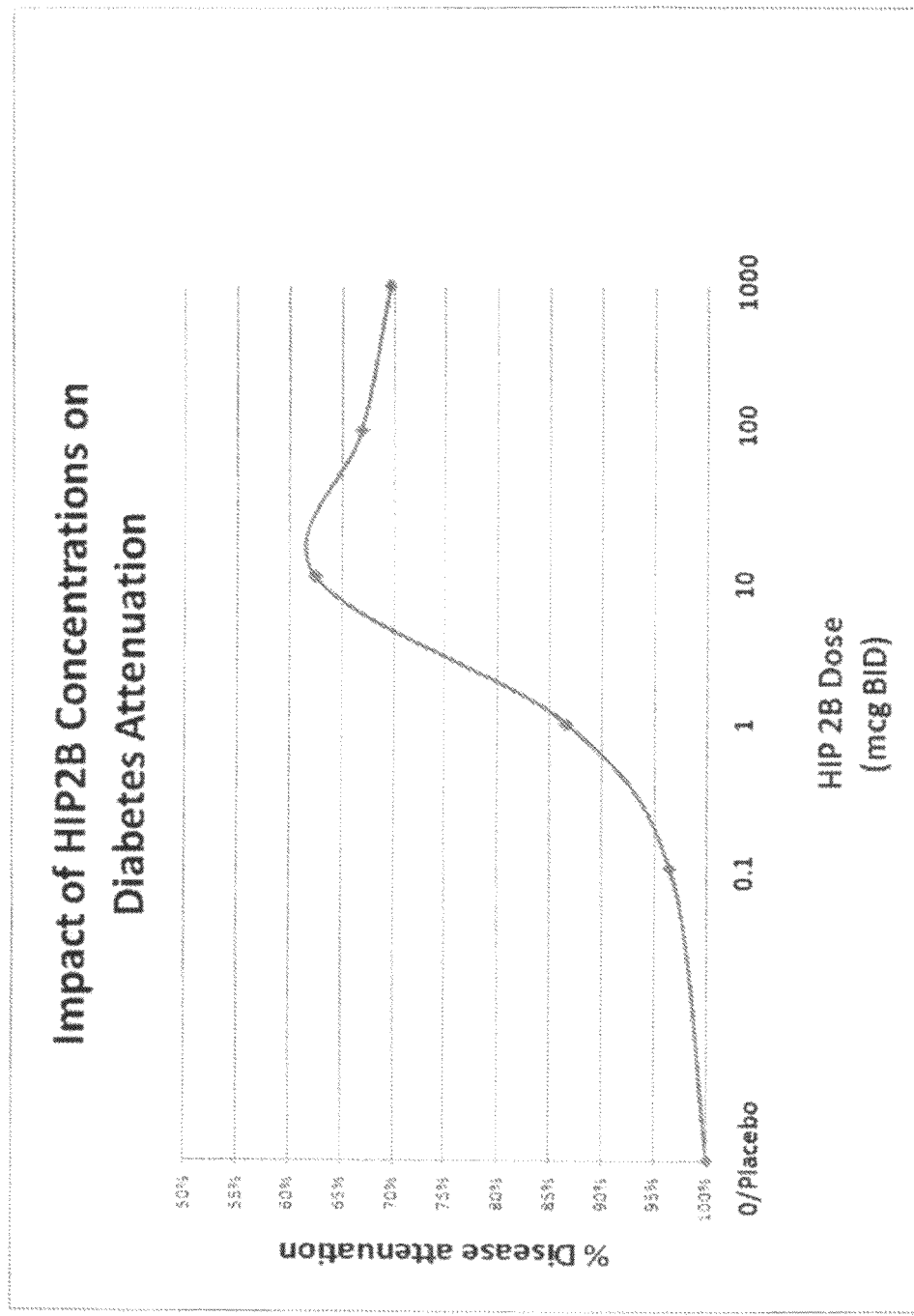
FIG. 23 depicts the impact of differing concentration of HIP2B on the attenuation of diabetes.

Based upon dosage ranging studies (Example 13) utilizing HIP2 and Optimized HIP2B in dose ranges from 1000 micrograms twice daily to 0.1 micrograms per day delivered IP to STZ-rendered diabetic mice, HIP2B could be utilized in a dosage of approximately 10% of that of HIP2 and the equivalent of approximately 1 mg/kg compared to 10 mg/kg (600 mg/day) dosage used in human trials of hamster-derived INGAP (FIG. 23)

For example, in some aspects, the various embodiments are directed to a pharmaceutical composition comprising a compound, as defined above, and a pharmaceutically acceptable carrier or diluent, or an effective amount of a pharmaceutical composition comprising a compound as defined above.

The compounds disclosed herein can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of the present disclosure (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the compounds of the present disclosure and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present disclosure. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The compounds of the present disclosure can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present disclosure can also be formulated in rectal compositions such as suppositories or retention enemas, e.g., containing conventional suppository bases such as cocoa butter or other glycerides.

In addition to the formulations described previously, the compounds of the present disclosure can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present disclosure, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present disclosure can also be administered in combination with other active ingredients, such as, for example, adjuvants, protease inhibitors, or other compatible drugs or compounds where such combination is seen to be desirable or advantageous in achieving the desired effects of the methods described herein.

Methods of Preparing Optimized HIP and Analogs or Derivatives Thereof

Any techniques known in the art can be used in synthesizing and purifying Optimized HIP or an analog or derivative thereof, including, but not limited to, de novo chemical synthesis and purification by precipitation, adsorption (e.g., column chromatography, membrane adsorbents, radial flow columns, batch adsorption, high-performance liquid chromatography, ion exchange chromatography, inorganic adsorbents, hydrophobic adsorbents, immobilized metal affinity chromatography, affinity chromatography), or gel filtration, electrophoresis, liquid phase partitioning, detergent partitioning, organic solvent extraction, and ultrafiltration. During purification, the biological activity of Optimized proislet peptides, including HIP, or an analog or derivative thereof may be monitored by one or more in vitro or in vivo assays. The purity of Optimized proislet peptide or an analog or derivative thereof can be assayed by any methods known in the art, such as but not limited to, gel electrophoresis. See Scopes, supra. In some embodiments, Optimized proislet peptide, including HIP, or an analog or derivative thereof employed in a composition disclosed herein can be in the range of 80 to 100 percent of the total mg protein, or at least 80%, at least 85%, at least 90%, at least 95%, or at least 98% of the total mg protein. In one embodiment, Optimized proislet peptide, including HIP or an analog or derivative thereof employed in a composition that is at least 99% of the total protein. In another embodiment, Optimized proislet peptide, including HIP or an analog or derivative thereof is purified to apparent homogeneity, as assayed, e.g., by sodium dodecyl sulfate polyacrylamide gel electrophoresis. In one embodiment, Optimized proislet peptide, including HIP is synthesized and tested by HPLC to a purity greater than 95%.

Methods known in the art can be utilized to produce Optimized proislet peptide, including HIP or an analog or derivative thereof recombinantly. A nucleic acid sequence encoding Optimized proislet peptide, including HIP or an analog or derivative thereof can be inserted into an expression vector for propagation and expression in host cells.

An expression construct, as used herein, refers to a nucleic acid sequence encoding a Optimized proislet peptide, including HIP or an analog or derivative thereof operably associated with one or more regulatory regions that enable expression of a Optimized HIP or an analog or derivative thereof in an appropriate host cell. "Operably-associated" refers to an association in which the regulatory regions and the Optimized proislet peptide, including HIP or an analog or derivative thereof to be expressed are joined and positioned in such a way as to permit transcription, and ultimately, translation.

The regulatory regions that are necessary for transcription of Optimized proislet peptide, including HIP or an analog or derivative thereof can be provided by the expression vector. A translation initiation codon (ATG) may also be provided if a Optimized proislet peptide, including HIP or an analog or derivative thereof gene sequence lacking its cognate initiation codon is to be expressed. In a compatible host-construct system, cellular transcriptional factors, such as RNA polymerase, will bind to the regulatory regions on the expression construct to effect transcription of the Optimized proislet peptide, including HIP sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In order to attach DNA sequences with regulatory functions, such as promoters, to a Optimized proislet peptide, including HIP or an analog or derivative thereof gene sequence or to insert a Optimized proislet peptide, including HIP or an analog or derivative thereof gene sequence into the cloning site of a vector, linkers or adapters providing the appropriate compatible restriction sites may be ligated to the ends of the cDNAs by techniques well known in the art. Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA using PCR with primers containing the desired restriction enzyme site.

An expression construct comprising a Optimized proislet peptide, including HIP or an analog or derivative thereof sequence operably associated with regulatory regions can be directly introduced into appropriate host cells for expression and production of a proislet peptide, including Optimized HIP or an analog or derivative thereof without further cloning. The expression constructs can also contain DNA sequences that facilitate integration of a proislet peptide, including Optimized HIP or an analog or derivative thereof sequence into the genome of the host cell, e.g., via homologous recombination. In this instance, it is not necessary to employ an expression vector comprising a replication origin suitable for appropriate host cells to propagate and express Optimized proislet peptide, including HIP or an analog or derivative thereof in the host cells.

A variety of expression vectors may be used, including but are not limited to, plasmids, cosmids, phage, phagemids or modified viruses. Such host-expression systems represent vehicles by which the coding sequences of a Optimized proislet peptide, including HIP or an analog or derivative thereof gene may be produced and subsequently purified, but also represent cells which may, when transformed or transfected with the appropriate nucleotide coding sequences, express Optimized proislet peptide, including HIP or an analog or derivative thereof in situ. These include, but are not limited to, microorganisms such as bacteria (e.g., *E. coli* and *B. subtilis*) transformed with recombinant bacteriophage DNA, plasmid DNA or cosmid DNA expression vectors containing Optimized proislet peptide, including HIP or an analog or derivative thereof coding sequences; yeast (e.g., *Saccharomyces*, *Pichia*) transformed with recombinant expression vectors containing proislet peptide, including Optimized HIP or an analog or derivative thereof coding sequences; insect cell systems infected with recombinant virus expression vectors (e.g., baculovirus) containing Optimized proislet peptide, including HIP or an analog or derivative thereof coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Optimized proislet peptide, including HIP or an analog or derivative thereof coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli* and eukaryotic cells are used for the expression of a recombinant Optimized proislet peptide, including HIP or an analog or derivative thereof. For example, mammalian cells such as Chinese hamster ovary cells (CHO) can be used with a vector bearing promoter element from major intermediate early gene of cytomegalovirus for effective expression of a Optimized proislet peptide, including HIP or an analog or derivative thereof sequence.

In bacterial systems, a number of expression vectors may be advantageously selected depending upon the use intended for the Optimized proislet peptide, including HIP or an analog or derivative thereof being expressed. For example, when a large quantity of a Optimized proislet peptide, including HIP or an analog or derivative thereof is to be produced, for the generation of pharmaceutical compositions of a Optimized proislet peptide, including HIP or an analog or derivative thereof, vectors that direct the expression of high levels of fusion protein products that are readily purified may be desirable. Vectors include, but are not limited to, the *E. coli* expression vector pCR2.1 TOPO (Invitrogen); pIN vectors, and the like. Series of vectors like pFLAG (Sigma), pMAL (NEB), and pET (Novagen) may also be used to express the foreign proteins as fusion proteins with FLAG peptide, malE-, or CBD-protein. These recombinant proteins may be directed into periplasmic space for correct folding and maturation. The fused part can be used for affinity purification of the expressed protein. Presence of cleavage sites for specific proteases like enterokinase allows one to cleave off the Optimized proislet peptide, including HIP or an analog or derivative thereof. The pGEX vectors may also be used to express foreign proteins as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, many vectors to express foreign genes can be used, e.g., *Autographa californica* nuclear polyhedrosis virus (AcNPV) can be used as a vector to express foreign genes. The virus grows in cells like *Spodoptera frugiperda* cells. An Optimized proislet peptide, including HIP or an analog or derivative thereof coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, an Optimized proislet peptide, including HIP or an analog or derivative thereof coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Optimized proislet peptide, including HIP or an analog or derivative thereof in infected hosts. Specific initiation signals may also be required for efficient translation of inserted Optimized proislet peptide, including HIP or an analog or derivative thereof coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, and the like.

In addition, a host cell strain may be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript and post-translational modification of the gene product, e.g., glycosylation and phosphorylation of the gene product, may be used. Such mammalian host cells include, but are not limited to, PC12, CHO, VERY, BHK, HeLa, COS, MDCK, 293, 3T3, W138, BT483, Hs578T, HTB2, BT2O and T47D, NS0 (a murine myeloma cell line that does not endogenously produce any immunoglobulin chains), CRL7O3O, and HsS78Bst cells. Expression in a bacterial or yeast system can be used if post-translational modifications are found to be non-essential for a desired activity of Optimized HIP or an analog or derivative thereof.

For long-term, high-yield production of properly processed Optimized proislet peptide, including HIP or an analog or derivative thereof, stable expression in cells is preferred. Cell lines that stably express Optimized proislet peptide, including HIP or an analog or derivative thereof may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and may, depending on the vector construct and host cell employed, allow cells to stably integrate the expression construct into their chromosomes and to grow in culture and to be expanded into cell lines. Such cells can be cultured for a long period of time while Optimized proislet peptide, including HIP or an analog or derivative thereof is expressed continuously.

A number of selection systems may be used, including but not limited to, antibiotic resistance (markers like Neo, which confers resistance to geneticine, or G-418; Zeo, for resistance to Zeocin; and Bsd, for resistance to blasticidin); antimetabolite resistance (markers like Dhfr, which confers resistance to methotrexate; gpt, which confers resistance to mycophenolic acid; and hygro, which confers resistance to hygromycin. In addition, mutant cell lines including, but not limited to, tk-, hgprt- or aprt-cells, can be used in combination with vectors bearing the corresponding genes for thymidine kinase, hypoxanthine, guanine or adenine phosphoribosyl-transferase. Methods commonly known in the art of recombinant DNA technology may be routinely applied to select the desired recombinant clone, 150:1.

The recombinant cells may be cultured under standard conditions of temperature, incubation time, optical density and media composition. However, conditions for growth of recombinant cells may be different from those for expression of Optimized proislet peptide, including HIP or an analog or derivative thereof. Modified culture conditions and media may also be used to enhance production of Optimized proislet peptide, including HIP or an analog or derivative thereof. Any techniques known in the art may be applied to establish the optimal conditions for producing Optimized proislet peptide, including HIP or an analog or derivative thereof.

An alternative to producing Optimized proislet peptide, including HIP or a fragment thereof by recombinant techniques or purification from natural sources is peptide synthesis. For example, an entire Optimized HIP or an analog or derivative thereof, or a protein corresponding to a portion of Optimized HIP or an analog or derivative thereof, can be synthesized by use of a peptide synthesizer. Conventional peptide synthesis or other synthetic protocols well known in the art may be used.

Proteins having the amino acid sequence of Optimized proislet peptide, including HIP or an analog or derivative thereof or a portion thereof may be synthesized by solid-phase peptide synthesis. During synthesis, N-a-protected amino acids having protected side chains are added stepwise to a growing polypeptide chain linked by its C-terminal and to an insoluble polymeric support, i.e., polystyrene beads. The proteins are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile. Details of appropriate chemistries, resins, protecting groups, protected amino acids and reagents are well known in the art and so are not discussed in detail herein.

Purification of the resulting Optimized proislet peptide, including HIP or an analog or derivative thereof is accomplished using conventional procedures, such as preparative HPLC using gel permeation, partition and/or ion exchange chromatography. The choice of appropriate matrices and buffers are well known in the art and so are not described in detail herein.

With the foregoing detailed description of the reagents and methods of the invention, the following Examples are provided to illustrate various aspects of the invention.

EXAMPLE 1

In Vitro HIP Activity. The in vitro studies were conducted at the University of Pennsylvania Human Islet Laboratory. Human pancreatic islet and ductal fractions were cultured over 10 days and then treated in a blinded study. Radioimmunoassay methods were used to measure insulin levels in the human pancreatic cultures treated with a scrambled peptide serving as a negative control, HIP3, HIP1, HIP2 and hamster-derived INGAP serving as a positive control. Peptides were synthesized by Bachem BioScience (95% pure, research grade).

Duplicate cultures were treated on day 10 and day 12 and then lysed for detection of insulin content after 1 week of treatment HIP peptides, control and INGAP. During 10-day culture, the insulin production goes down and then after treatment with HIP peptides, insulin is produced again.

The ductal fraction graph as shown in FIG. 1 depicts the insulin levels on the y axis as measured by radioimmunoassay after incubation in culture with human pancreatic ductal tissue. The islet fraction graph indicates insulin levels after incubation in human pancreatic islet tissue. Baseline insulin levels are significantly higher in the islet fraction at baseline than in the ductal fractions at baseline.

The ductal and islet tissue were separated using the Ricordi method. Neither ductal cell nor islet culture was completely homogeneous in nature. The studies also suggest that progenitor cells, which are the target for HIP, are found both in islet and ductal cultures. The studies were repeated with similar findings shown in the following chart, with as much as a four-fold increase in insulin levels by radioimmunoassay among human ductal tissue cultured with HIP 2.

Repeated studies confirmed the increase in insulin both in predominately human ductal cell cultures and islet cultures, with baseline insulin levels consistently about ⅓ lower in the baseline ductal cultures compared to islet cultures, with similar rises in insulin content after incubation with HIP peptides compared to a negative control.

EXAMPLE 2

In Vivo Studies. HIP3, HIP1 and HIP2 has been the subject of in vivo studies in mice. Studies have shown that these HIP variants, when introduced into diabetic mice, stimulate differentiation of progenitor cells within the pancreas into new islet structures A model of diabetes has been developed in the mouse (Rosenberg et. al., 2004). The subject number was selected to yield a sufficient number of diabetic animals for the study and animals were randomly assigned to study groups. All animals were dosed via intraperitoneal injections twice daily (am and pm) for 28 consecutive days. The timing of dose administration remained consistent (±2 hours) during the dosing phase. After confirmation that the mice had been diabetic (blood glucose greater than 16.7 mmol/L (300 mg/dL) for at least 1 week, mice were dosed.

Mice were injected intraperitoneally with streptozocin at 40 mg/kg in citrate buffer, pH 4.5, on 5 consecutive days in an attempt to render them diabetic. Mice must have had blood glucose greater than 16.7 mmol/L (300 mg/dL) for at least 1 week to be considered diabetic. If the blood glucose level in any animal rose to above 400 mg/dL, the animal was treated with insulin. Every 3 days, at the same time each day, a nick was made on the tail and a drop of blood was collected. Glucose measurements were determined using a glucose meter. Group assignments and dose levels were as follows in Table 1:

TABLE 2

| Group | Treatment | Dose Level | Dose Volume | Number of Animals |
|---|---|---|---|---|
| 1 | Vehicle | 0 | 100 μl | 6 |
| 2 | HIP3 | 250 μg | 100 μl | 6 |
| 3 | HIP1 | 250 μg | 100 μl | 6 |
| 4 | HIP2 | 250 μg | 100 μl | 6 |

Study endpoints included the following: changes in glucose; changes in insulin requirements; and histology of postmortem pancreata.

Figure 2:
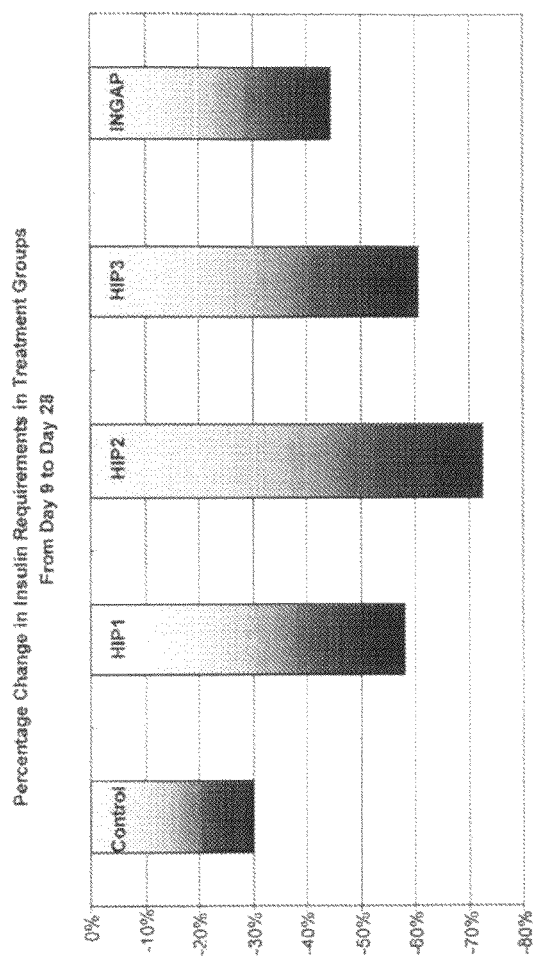
FIG. 2 is a graph depicting the insulin requirements in mice treated with HIP1, HIP2 and HIP3.

Changes in Insulin Requirements. Significant reductions in both the insulin requirements and the rate of decrease in insulin requirements were seen among HIP-treated mice, as shown in FIG. 2. The HIP 2-treated mice were completely insulin-free by day 21.

Figure 3:
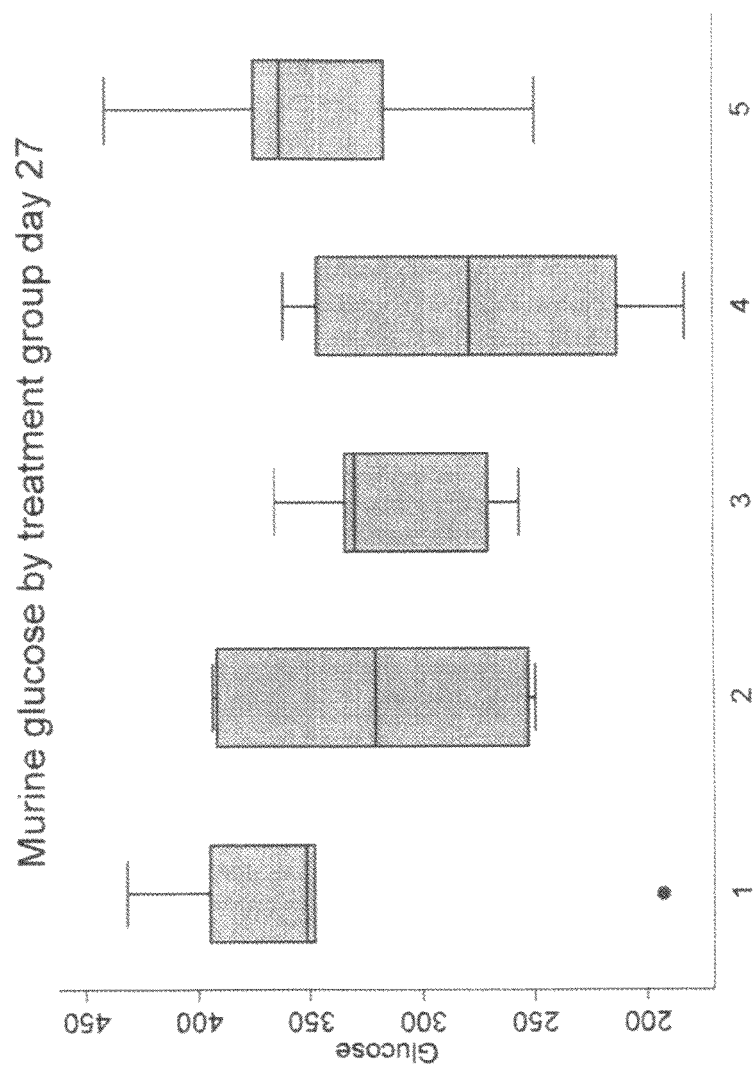
FIG. 3 is a graph depicting the mean reduction in glucose from baseline in mice treated with HIP1, HIP2 and HIP3.

Changes in Glucose Levels. There was a mean reduction in glucose from baseline compared with controls in all of the HIP-treated groups and this reduction was significant in all HIP-treated groups, as shown in FIG. 3. There was a 14.7% lower mean glucose between HIP1 and control, a 29.4% lower mean glucose between HIP 2 and control, and a 57.3% mean lower glucose between HIP3 and the control group. The data indicates the significantly faster rate of decline in insulin requirements among all HIP-treated mouse groups compared to control diabetic mice. There were significantly greater numbers of islets after HIP treatment observed in mouse pancreata, which were sectioned and reviewed on each mouse studied. The pancreata were evaluated by a histologist blinded the specimens with the following data in Table 3.

TABLE 3

|  | Total Islets (% increase) | Total Islet Mass (μm2) (% increase) |
| --- | --- | --- |
| Placebo | 280 | 854364 |
| HIP2 | 454 (62%) | 2161782 (153%) |
| HIP3 | 410 (46%) | 1703513 (99%) |

Figure 4B:
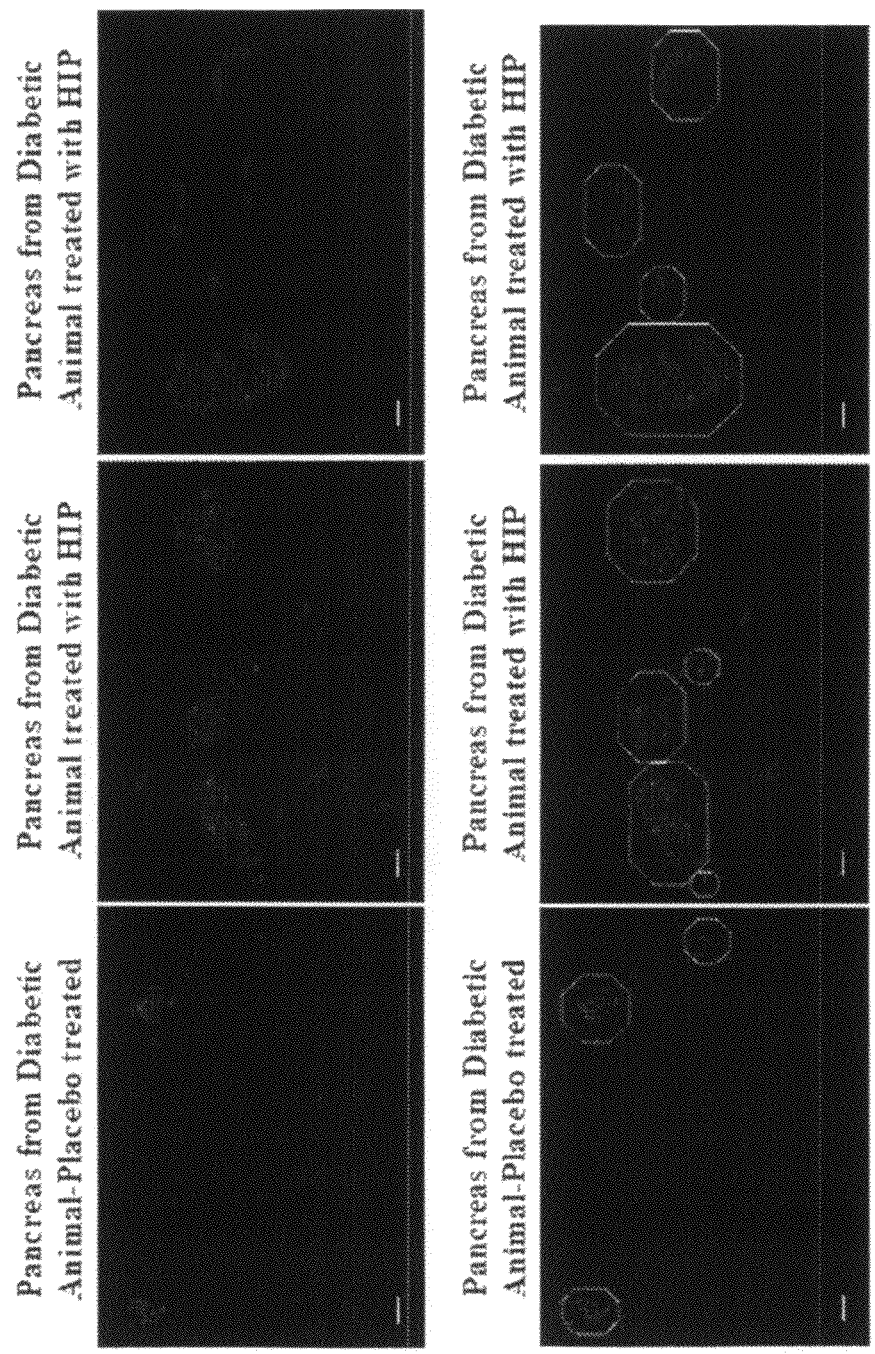
FIG. 4B provides representative images of insulin immunostaining in placebo- and HIP-treated mice and insulin-stained islets are outlined in yellow to differentiate these structures from auto-fluorescent blood cells. Scale bar=50 μm in all images.

The difference in islet number between HIP and placebo was statistically significant (p=0.022). There was even a more profound increase in islet area between the HIP-treated mice and the placebo-treated group. The islet area in the HIP2-treated group was 360,297 μm(2) compared to 142,394 μm(2) in the placebo-treated group with 283,918 μm(2) in the HIP3-treated group (p=0.05), as shown in FIG. 4A. FIG. 4B shows that HIP2B increases islet number in diabetic mice. (a) Representative images of insulin immunostaining in placebo- and HIP-treated mice. (b) Insulin-stained islets are outlined in yellow to differentiate these structures from auto-fluorescent blood cells.

Immunofluorescent staining for insulin was also performed on mouse pancreata demonstrate are greater degree of insulin staining in the HIP-treated mice, as shown in FIG. 5. This mouse pancreas tissue was harvested and fixed in 4% PFA, blocked and sectioned. 10X-Objective, 1.6 optivar.

EXAMPLE 3

The following example describes exemplary methods of synthesizing and purifying HIP and Optimized HIP.

Synthesis of HIP peptides was by the general solid-phase procedure of Merrifield (Merrifield, R. B. 1963, J. Am. Chem. Soc. 85:2149-2154) using standard Fmoc protection chemistry (Fields, G. B. and Noble, R. L. 1990, Int. J. Peptide Protein Res. 35, 161-214).

Resin bound protected peptide was cleaved and deprotected by treatment with trifluoroacetic acid (TFA) in the presence of scavenger to give crude product. Purified peptide product was obtained by reverse-phase high performance liquid chromatography (HPLC).

Derivatization of peptides with polyethylene glycol (PEG) may consist of the introduction of discrete PEG units in a molecular weight range of 300 to 43,000.

Example A: Ac-IGLHDPTQGTEPNG-NH$_2$ (HIP2B) (SEQ ID NO: 7). Starting with the Rink amide resin, 4-[2',4'-Dimethoxyphenyl-Fmoc-aminomethyl)-phenoxy resin, Fmoc protected amino acids are introduced sequentially and coupled using HOBt and DCC (N-hydroxybenzotriazole and dicyclohexylcarbodiimide). Fmoc deprotection of the starting resin and the Fmoc protecting group of each amino acid was achieved with 20% piperidine in dimethylformamide. Following removal of the Fmoc protecting group of the N-terminal amino acid, Ile, the resin bound protected peptide was acetylated with 20% acetic anhydride in methylene chloride. Deprotection of the side chain groups and cleavage of the peptide from the resin was achieved with 95% trifluoroacetic acid with 2.5% water and 2.5% triisopropylsilane. Following a one hour treatment the peptide was precipitated from the cleavage solution with diethylether, filtered and dried.

Purification. The crude product was purified by reverse phase high performance liquid chromatography (HPLC) on a C-18 support using 0.1% TFA in water and a 0.1% TFA in acetonitrile as buffers A and B respectively. An increasing gradient of buffer B was used to elute the product. Exchange of residual TFA to acetate was achieved by reapplying the product fractions onto a C-18 HPLC column, washing with aqueous 0.1M NH$_4$OAc and eluting the product with a gradient of 1% acetic acid in water and acetonitrile as the mobile phase. Pure product fractions were pooled and lyophilized. Identity and homogeneity of the peptide was confirmed by amino acid compositional analysis, analytical HPLC, and mass spectral analysis.

Example B: IGLHDPTQGTEPNG (HIP2) (SEQ ID NO: 4). Starting with Fmoc-Gly-Wang resin, the peptide sequence was assembled as in Example A. The amino terminus was not acetylated as to provide the peptide with an unblocked free amino and carboxyl terminus. Purified product was isolated as in Example A.

Example C: (Ac-IGLHDPTQGTEPNGC-NH$_2$)$_2$ (HIP2B CysDimer) (SEQ ID NO: 19). Synthesis of the peptide in its' free thiol form was as described in Example A. The crude product was oxidized to form dimer by dissolving about 2g of peptide with 2 ml acetic acid and dilution with ~500 ml distilled water, the pH was adjusted to ~8.2 by adding 20% NH$_4$OH solution drop-wise. The solution was allowed to stir overnight at room temperature. The reaction did not reach completion overnight. To complete the reaction a 1% solution of potassium ferricyanide was added until a permanent yellowish green color persisted. The reaction was judged to be complete as determined by the Ellman test and HPLC analysis. The solution of oxidized peptide was then stirred with 3-5g of AG-1×2 ion exchange (chloride form) resin for 30 minutes, filtered and the pH adjusted to ~5 with acetic acid prior to HPLC purification.

Example D: (IGLHDPTQGTEPNGC)$_2$ (HIP2 Cys Dimer) (SEQ ID NO: 13). Starting with Fmoc-Cys(Trt)-Wang resin the peptide sequence was prepared as in Example 2. Ether precipitation of the crude product, oxidation to dimer and HPLC purification was achieved as described in Example C.

Example E: Ac-IGLHDPTQGTEPNGC-NH$_2$ (HIP2B Cys) (SEQ ID NO: 16). Synthesis and purification of the monomeric primary sequence is accomplished as in Example A.

The following example describes an exemplary method of preparing blocked HIPs: The HIP blocked peptides were prepared by Solid Phase Peptide Synthesis (SPPS). The fundamental premise of solid phase synthesis is that amino acids can be assembled into a peptide of any desired sequence while one end of the chain is anchored to an insoluble support. As mentioned above, in practical SPPS the carboxyl terminus of the peptide is linked to the polymer. After the desired sequence of amino acids has been linked together on the support, a reagent can be applied to cleave the peptide chain from the support and liberate the crude peptide into solution.

All the reactions involved in the synthesis are carried to completion if possible, so that a homogeneous product could be obtained.

When the C-terminal of a peptide is an amide the derivative is a peptide amide. Peptide-amides are extremely important derivatives since many naturally occurring peptide hormones are present as the amide. To synthesize peptide amides solid phase resins have been developed which yield peptide amides directly upon cleavage. When the N-terminal is an acetyl group, the peptide is assembled from the C-terminal to the N-terminal. The N-terminal is then acetylated using acetic anhydride in the presence of a base.

Fmoc-amino acid derivatives are used to build the sequence. After the desired sequence of amino acids was linked together on the support the peptide is acetylated, filtered and dried. The acetylated peptide-resin is then cleaved with Trifluoroacetic acid (TFA) containing scavengers to release the peptide from the support as well as all protecting groups. Purification is then performed on the crude material using High Performance Liquid Chromatography (HPLC).

Example F: Ac-IGLHDPTQGTEPNGC(PEG)-NH$_2$ (HIP2B Cys-PEG) (SEQ ID NO: 25). The monomeric purified form of the peptide from Example 5 (1.1 equivalent) was dissolved in acetate buffer (0.1M, pH=6.5). A solution (1 equivalent) of maleimide derivatized polyethylene glycol (PEG maleimide) was prepared in distilled water and added to the peptide solution with stirring. The pH of the resulting solution was adjusted to ~6.5 with dilute NH$_4$OH solution, stirred at room temperature for 30 minutes, acidified with a few drops of acetic acid and purified by HPLC.

Example G: IGLHDPTQGTEPNGC(PEG) (HIP2 Cys-PEG) (SEQ ID NO: 22). Starting with Fmoc-Cys(Trt)-Wang resin, synthesis and purification of the primary sequence is as described in Example B. Derivatization with PEG maleimide followed by HPLC purification is as in Example F.

Example H: (PEG)-IGLHDPTQGTEPNG (PEG-HIP2) (SEQ ID NO: 91). The primary resin bound peptide sequence was prepared as in Example 2. Following Fmoc deprotection of the N-terminal Ile the protected peptide resin was derivatized with PEG-carboxylic acid using HOBT and DCC as coupling agents. Cleavage and purification of the (PEG)-peptide from the resin was as described in Example A.

EXAMPLE 4

The following example illustrates the pharmacokinetics of the intramuscular and subcutaneous administration of HIP1, which is cleaved into HIP2.

Figure 6:
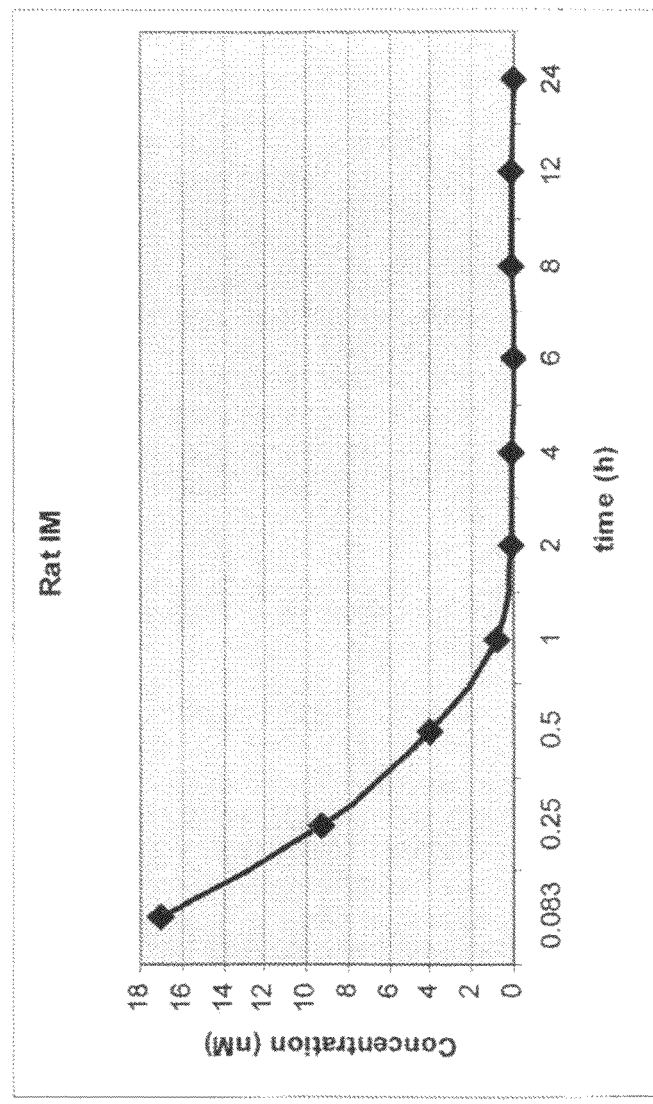
FIG. 6 is a graph depicting the half-life of HIP delivered intramuscularly in rats.

The pharmacokinetics of HIP delivery with 20 rats with 5 rats per route of administration was evaluated. Similar to hamster-derived INGAP findings, the intramuscular (IM) route provided a better blood concentration of the material, but half-life determinations were under 30 minutes by ELISA measurements, as shown in FIG. 6.

Figure 7:
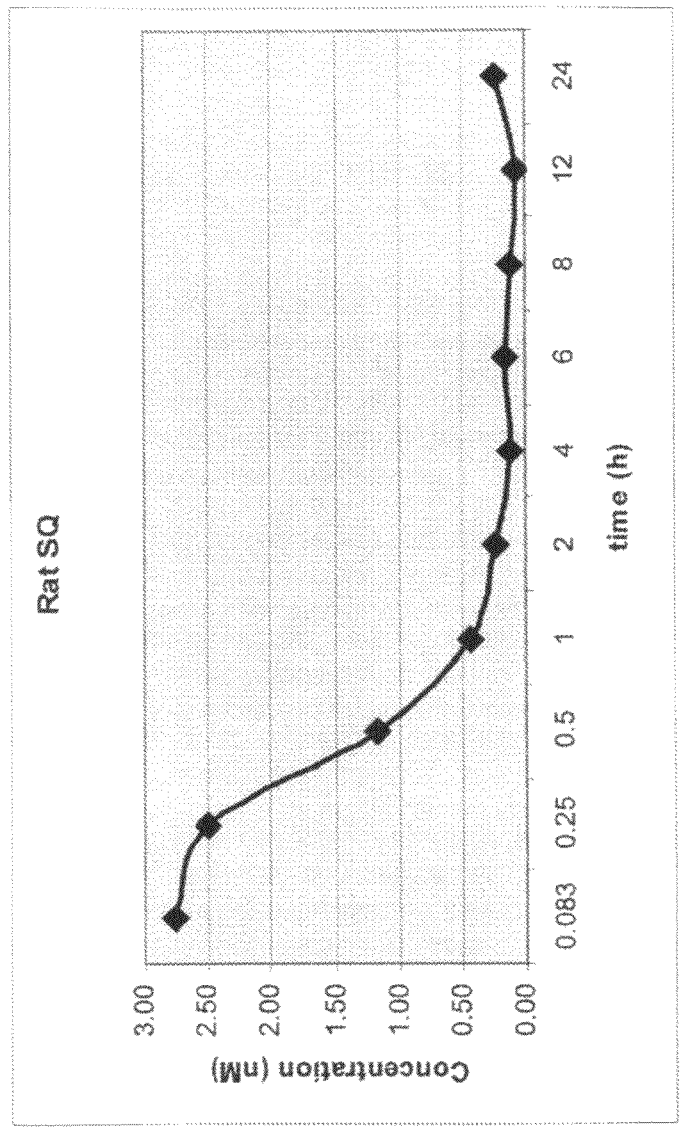
FIG. 7 is a graph depicting the half-life of HIP delivered subcutaneously to rats.

The subcutaneous (SQ) route of administration showed a slightly longer half-life, as shown in FIG. 7, but the levels detected by ELISA were less than by the IM route. The IM route provides a slightly longer half-life in the blood than SQ.

EXAMPLE 5

The following example shows the stability of HIP2B peptide in a freeze-thaw study.

Experimental Procedure. The study was initiated with two groups of eight samples each. One group is maintained at 4-8° C. and the other at 25° C., as part of a 2 month stability study. Each sample contains 4.57 milligrams of HIP2B in 5 micro liters of distilled water. One sample from each temperature group is removed and placed in a minus 20° C. freezer, for storage, every seven days until an LC/MS analysis can be performed. A series of samples were evaluated after 1, 2, and 3 weeks in the stability study against a control sample of HIP2B which had been prepared at the initiation of the study and stored at −20° C. After three weeks of stability testing at each of the temperatures described above, all of the samples were unchanged as determined by LC/MS and therefore deemed stable at 1, 2, and three weeks. This stability freeze-thaw studies suggest that a carbon shift occurs at the junction of Pro-Asn in the HIP sequence when it is stored in dimethyl sulfoxide (DMSO), the sequence remains stable for several months when stored in isotonic saline at −20° C.

EXAMPLE 6

Optimized HIP Demonstrates Increased Peptide Stability to Serum Proteases In Vitro Over Time (T).

The peptides were incubated in human plasma, at 37° C. Sample incubations were performed over a period of 1 hr. Individual time points of 1, 5, 10, 30, and 60 minutes were used to follow the reactions. Deactivation of plasma proteases at each time point was achieved by heating the samples at 100° C. for 1 min. Following work-up the plasma treated samples were evaluated by reverse phase chromatography in series with at mass spectrometer, HPLC/LC-MS, against control samples.

Plasma Treated with HIP and Optimized HIP peptides were evaluated over 1, 5, 10, 30 and 60 minutes. For each time point 0.70 ml of plasma was pipetted into a 10 ml test tube. To each was added 0.30 ml of a stock solution of HIP or Optimized HIP peptide (1.66 mg/ml) prepared in phosphate buffered saline. The plasma/peptide samples were incubated at 37° C. for each time point followed by heating at 100° C. to inactivate the proteolytic activity of plasma proteases. Following inactivation, the samples were diluted with 1 ml of H$_2$O, centrifuged and the supernatant liquid removed for analysis.

Samples were analyzed on a C-18 reverse phase column (50 mm×2.0 mm) using 0.07% TFA in H$_2$O as buffer A and 0.07% TFA in acetonitrile as buffer B. A linear gradient of 98% A/2% B progressing to 30% A/70% B over 10 min. was used at a flow rate of 0.4 ml/min. Eluant was monitored by UV at a wavelength of 220 nm and by mass spectroscopy. Comparisons of chromatographic profiles of plasma treated peptides (37° C.) against peptide reference samples and plasma controls were used to determine the relative stability of peptide to plasma treatment.

Controls

T=0: Plasma (0.7 ml) plus peptide stock solution (0.3 ml), heat 100° C. 1 min. add 1 ml H$_2$O, centrifuge.

Plasma background control: 0.7 ml plasma plus PBS (0.3 ml), heat 100° C. 1 min, add 1 ml H$_2$O, centrifuge.

Peptide reference heat treated: Peptide stock solution (0.3 ml) plus 0.7 ml PBS, heat 100° C. 1 min., add 1 ml H$_2$O.

Peptide reference no heat: Peptide stock solution (0.3 ml) add 0.7 ml PBS plus 1 ml H$_2$O.

Results.

HIP2 (IGLHDPTQGTEPNG) (SEQ ID NO: 4) Evidence of proteolysis by the appearance of a new component 5%) is evident after only 1 min. of HIP2 incubation. The new component continues to increase over time. At 30 min. it represents ≈50% and at 60 min. the concentration is ≈70%. The major metabolite is identified as GLHDPTQGTEPNG (SEQ ID NO: 92), indicating the primary loss of N-terminal isoleucine. In addition, there is evidence for the presence of a small amount of HDPTQGTEPNG (SEQ ID NO: 93) resulting from the loss of IGL.

HIP2B (Ac-IGLHDPTQGTEPNG-NH$_2$) (SEQ ID NO: 7) The N-acetylated C-amide form of HIP2 appears to be completely stable to plasma proteases after 1 hr of incubation at 37° C.

HIP3 (IGLHDPTQGTEPNGE) (SEQ ID NO: 3) Proteolysis of HIP3 is slower relative to that of HIP2. After 60 min. the starting concentration of HIP3 is ≈50%. The major identified metabolite is HDPTQGTEPNG (SEQ ID NO: 93), indicating a loss of IG.

HIP3B (Ac-IGLHDPTQGTEPNGE-NH$_2$) (SEQ ID NO: 5) The blocked form of HIP3 is completely stable up to 1 hr of plasma incubation.

HIP2B Cys-Dimer (Ac-IGLHDPTQGTEPNGC-NH$_2$)$_2$ (SEQ ID NO: 19)

This compound appears to be stable to plasma proteases for at least 1 hr. However, 100° C. heat treatment of the incubated samples, as well as the T=0 control, indicated the conversion of the starting material to a cystine adduct whose structure is Ac-IGHDPTQGTEPNGC(C)—NH$_2$. (SEQ ID NO: 94) Conversion appears to be due to displacement by cysteine, from plasma, when the samples are heated at 100° C.

HIP2B Cys-PEG (Ac-IGLHDPTQGTEPNGC(PEG)-NH$_2$) (SEQ ID NO: 22). This high molecular construct is stable to plasma proteases for up to 1 hr.

Figure 8:
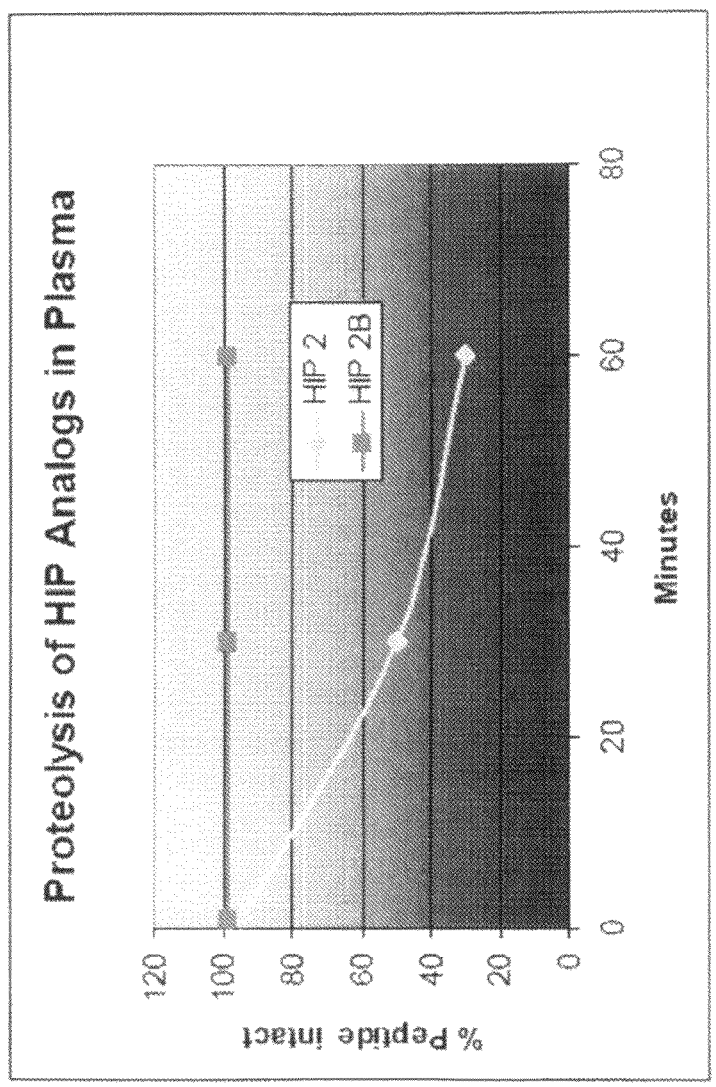
FIG. 8 is a graph depicting the in vitro stability of HIP 2 and HIP 2B in plasma over time.

Results. The proteolysis of the HIP2 and HIP2B peptides in plasma is shown in FIG. 8. The results of HIP2 showed appearance of a new component (~5%) after only 1 minute of incubation in plasma. This new component continues to increase over time and represents and the major metabolite is identified as the HIP2 sequence with primary loss of the N-terminal isoleucine and secondarily the loss of the first three amino acids. HIP2B appeared completely stable to plasma proteases after 1 hour of incubation at 37° C. Blocked forms of HIP2 and HIP3 referred to as HIP2B and HIP3B are clearly more stable to plasma proteases for up to 1 hr relative to the unblocked structures. Dimer and PEG derivatives of HIP2B are also very stable.

EXAMPLE 7

Utilizing a technique of growing an established immortalized human cell line from human pancreatic epithelioid cells known as PANC-1, the impact in vitro of impact of HIPs and Optimized HIPs on insulin production was evaluated. This cell line demonstrates the ability to differentiate into other pancreatic cell types upon appropriate signaling. Therefore, PANC-1 cells were used as a surrogate to the naturally occurring progenitor cells of the pancreas.

Panc-1 cells were seeded in T75 flasks in DMEM media containing 10% fetal bovine serum. The cells were incubated at 37° C., 5% CO2 for 24 hours and then treated with HIPs at the final concentration of 167 nM. This treatment was performed once a day for four days. On the fifth day the cells were broken to obtain the cell lysates. In these cell extracts the total protein levels were determined, and 50 micrograms of total protein were used to perform the western blot analysis. The samples containing 50 micrograms of proteins were diluted in loading buffer containing or not 5% of the reducing agent beta-mercaptoethanol, and loaded into each well of the gel. After the electrophoresis and transfer of the proteins to nitrocellulose membranes, the presence of insulin was detected by using as a primary antibody the polyclonal chicken anti insulin antibody (ab14042, dilution of 1/2000), and as secondary antibody the rabbit polyclonal-HRP conjugated anti-chicken (dilution 1/1000 for the NIT gel and 1/2000 for the PANC-1 gel).

Figure 9:
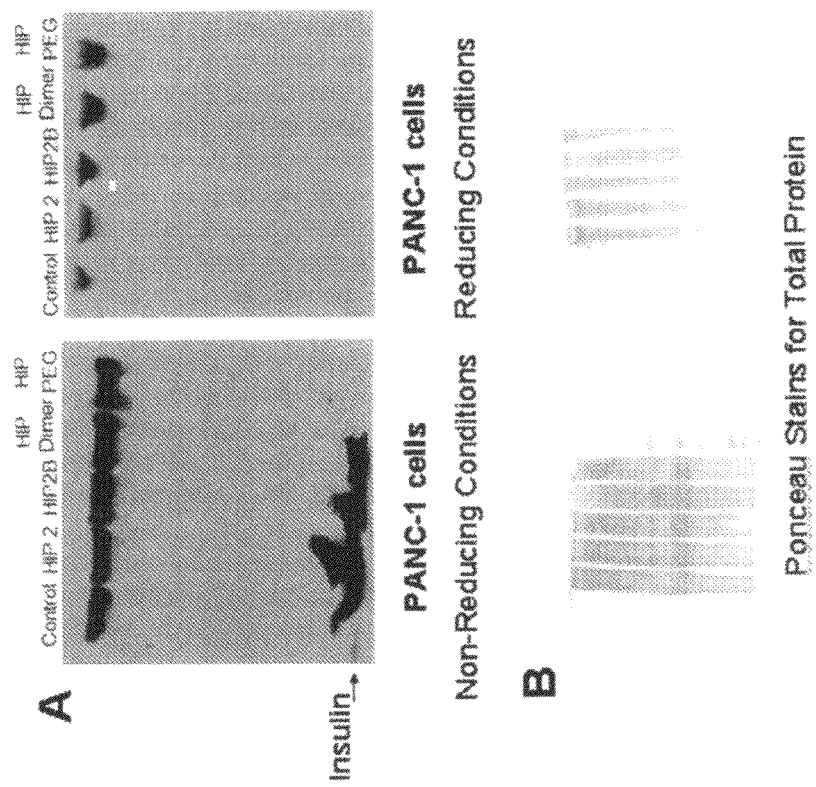
FIG. 9A is a Western Blot analysis demonstrating human insulin expression from PANC-1 cells under non-reducing and reducing conditions in response to incubation with various HIP and Optimized HIPs.
FIG. 9B are Ponceau Stains under non-reducing and reducing conditions in response to incubation with various HIP and Optimized HIPs.

FIG. 9 is the Western Blot analysis demonstrating expression of human insulin from PANC-1 cells in response to incubation with HIP optimized HIP. The panel below labeled A demonstrates bands for insulin in the Panc-1 cells when the samples were loaded in non-reducing conditions. The results indicate that HIP2, HIP2B, and 1-11P2 dimerized stimulate more insulin production than the HIP2 PEGylated or control. In reducing conditions, the disulphide bonds connecting the two polypeptide chain in the insulin are reduced and therefore the chain are separated and, in this condition, the insulin antibody does not react with insulin. In contrast to non-reducing conditions, the insulin molecule is complete and is recognized by the antibody.

FIG. 9B show the total protein contained in the same membranes as in FIG. 9A. The determination of the levels of total protein via Ponceau staining demonstrates that the different lanes contain similar amount of proteins. The total protein levels in the NIT-1 and PANC-1 cells were determined, and 50 micrograms of total protein were used to perform the Western Blot analysis. The samples containing 50 micrograms of proteins were diluted in loading buffer containing or not 5% of the reducing agent beta-mercaptoethanol, and loaded into each well of the gel.

The Ponceau staining demonstrates that the differences in insulin expression respond to different HIPs and Optimized HIPs are not related with amount of protein loaded in the wells. Also the lack of signal for insulin, for example, the membrane in the reducing conditions, is not attributed to a lack of protein.

EXAMPLE 8

Figure 10A:
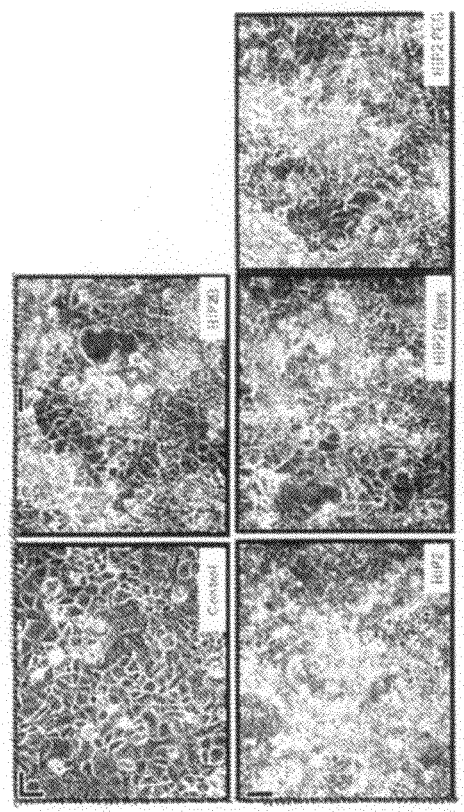
FIG. 10A demonstrates PANC-1 cells treated with HIP2, and Optimized HIP peptides for four days, with pictures taken on day 7 at 200× magnification.
Figure 10B:
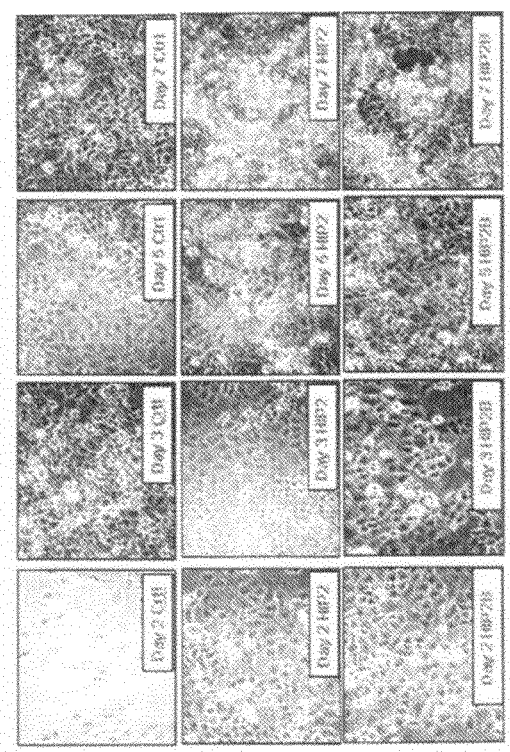
FIG. 10B demonstrates the progression of PANC-1 cell morphology changes through 7 days (control, HIP2 and HIP2B), with pictures taken on days 1, 2, 3, 5 and 7 at 200× magnification.
Figure 10C:
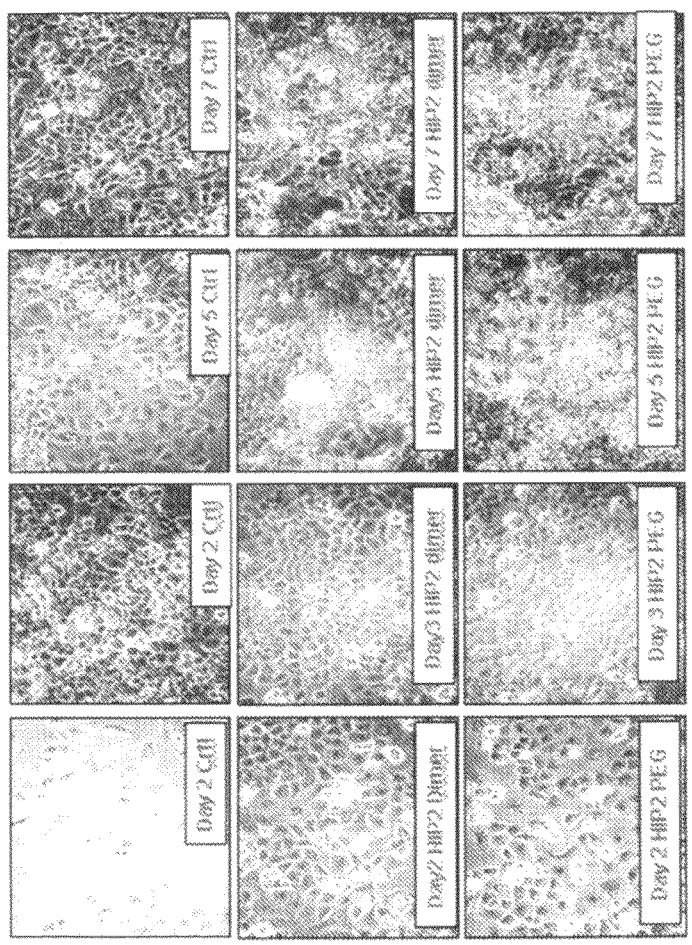
FIG. 10C demonstrates progression morphological changes of PANC-1 cells treated with control and Optimized HIPs (HIP2 Dimer and HIP2 PEG).

Effects of HIP and Optimized HIP Peptides on Cell Morphology of PANC-1 Cell Lines. The cells were treated with HIP and Optimized HIP peptides for four days. In FIG. 10A, taken on day 7 at 200× magnification, morphological differences can be seen between the control condition and the cells treated with HIPs and Optimized HIPS with histologically more differentiated cells, particularly in the HIP2B-treated cells. FIG. 10B show the progression of the cell morphology changes through 7 days, with the control on the top, HIP2 in the middle, and HIP2B on the bottom. Pictures were taken on days 1, 2, 3, 5, and 7 at 200× magnification. While the control-treated cells did not appear to undergo any changes, the cells treated with HIP2 and HIP2B deviate significantly from their initial appearance. FIG. 10C demonstrates the progression of morphological changes when HIP2 Dimer and HIP2 PEG are treated in PANC-1 cell cultures. Overall, the control-treated cells did not undergo any significant visual changes, the cells treated with HIP2 and HIP2B deviate significantly from their initial appearance.

EXAMPLE 9

Figure 11:
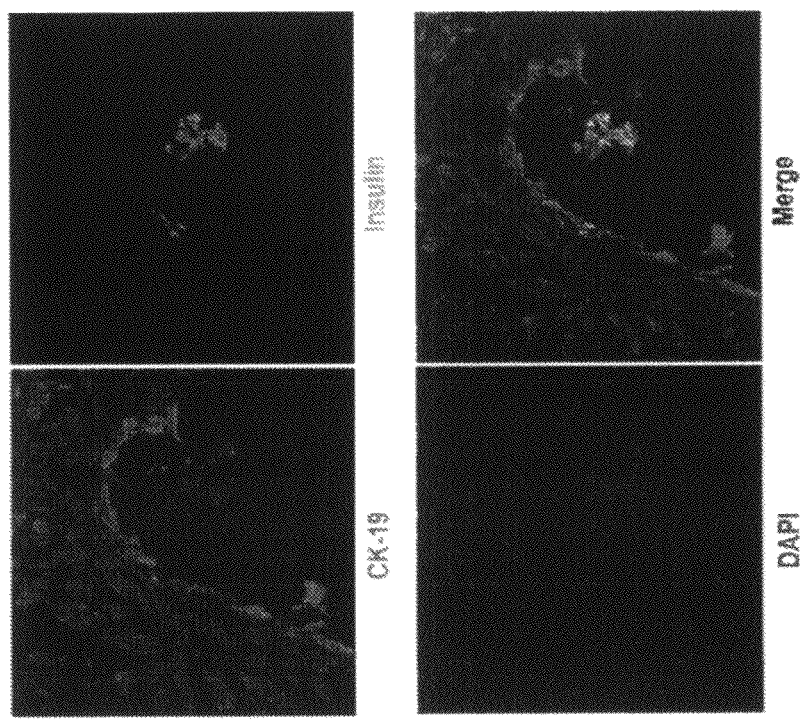
FIG. 11 is a stain for CK19 and DAP1 to show nuclei and insulin in human pancreatic cells following administration of HIP2B.

HIP 2B Activity in Human Pancreatic Tissue Culture. The University of Pennsylvania Human Islet Lab demonstrated the impact of HIP and Optimized HIP peptides in, human pancreatic ductal cell cultures. The ductal fraction of human pancreatic cells were cultured for 10 days in a collagen matrix and then treated every other day with HIP2B. Cells were labeled by double antibody staining for CK19, a marker for ductal tissue, and DAP1 staining to show nuclei and insulin. As shown in FIG. 11, the cells underwent morphological changes that induced insulin expression in otherwise insulin negative cells.

EXAMPLE 10

Pilot Data of Impact of HIP and Optimized Hip Peptides in the Non Obese Diabetic Model.

Consistent with the data in the STZ-treated mice (above) of increased islet mass, area and number, the pilot NOD mouse model demonstrated preliminary evidence of the potential for Optimized HIP to provide better efficacy in terms of islet neogenesis as measured by C-peptide levels in mice following HIP treatment for 39 days.

The non obese diabetic (NOD) model is used as a model for type 1 autoimmune diabetes. This form of diabetes is the most challenging in that the underlying damage to the pancreas and its insulin production is due to autoimmune attack. Therefore, in order to show definitive islet neogenesis in this form of diabetes an immune tolerance agent must be used in combination with HIP. The NOD mouse model is extremely difficult model because many of the mice may only transiently become diabetic and go into remission, whereas others develop severe diabetes. The timing intervention in this transgenic mouse model is difficult to determine.

Figure 12:
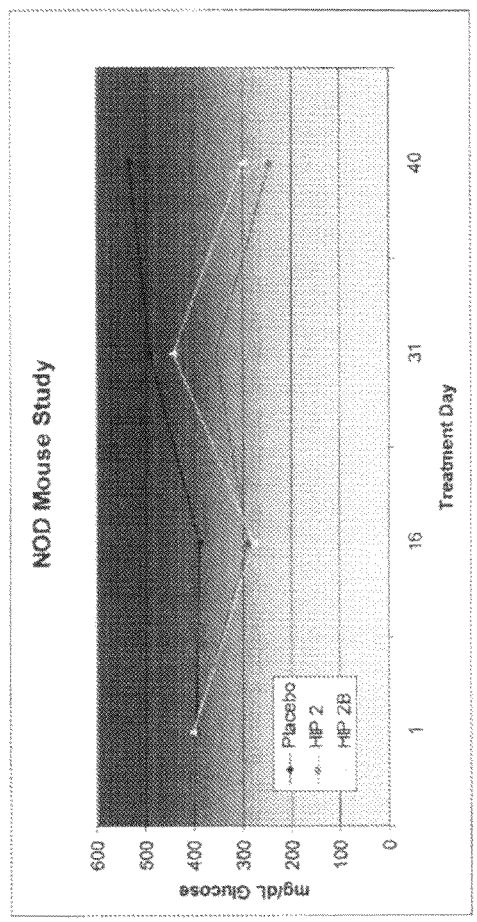
FIG. 12 is graph depicting glucose levels of three NOD mice after treatment with placebo and lysophylline (LSF), HIP 2 and LSF, and HIP2B and LSF.

In a preliminary study that utilizing the immune tolerance agent, lysophylline (LSF) under development, three NOD mice that became diabetic and were randomized to placebo plus LSF, HIP2 plus LSF and HIP2B plus LSF. As shown in FIG. 12, of the group who received LSF at the appropriate time, the two treated with HIP responded with steadily improved glucose levels during the study compared to the NOD mouse treated with LSF alone that had gradual elevations in glucose throughout the study. While not a statistically significant study, these data provide very compelling evidence for pursuit of the combination of an immune tolerance agent and HIP for type 1 diabetes.

EXAMPLE 11

Impact of HIP2B and HIP2 on HIP Receptor. The following sets of studies demonstrate that HIP2B is as effective as HIP2 in the interaction with the cytoplasmic membrane receptor for HIP and trafficking from the receptor to the nucleus. The receptor for Human ProIslet Peptide was labeled using a double antibody method in a stable human pancreatic cell line. The first antibody was a rabbit polyclonal and the second was a goat-anti-rabbit labeled with Cy3 fluorescent dye.

These cells grow normally in serum free media and when treated with trypsin, are destabilized and made competent to undergo developmental changes. Cells were cultured in serum free media (SFM) with and without HIP, and in serum free media with trypsin (TSFM). This is to show that simply destabilizing, does not activate developmental changes.

When treated with HIP under stable conditions, no changes result. When treated with HIP under developmentally competent conditions, the labeled receptor responds to the presence of HIP by being encapsulated by the cytoplasmic membrane and moving to the nuclear membrane where the signals for differentiation are received.

When treated with HIP under stable conditions, no changes result. When treated with HIP under developmentally competent conditions, the labeled receptor responds to the presence of HIP by being encapsulated by the cytoplasmic membrane and moving to the nuclear membrane where the signals for differentiation are received.

Figure 13:
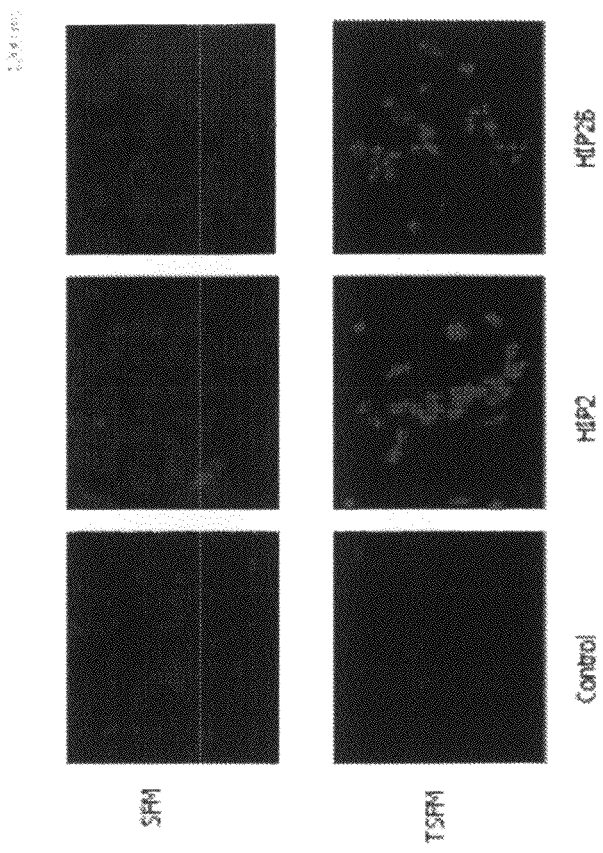
FIG. 13 is a Cy3 double antibody immunohistochemical staining of PANC-1 cells after treatment with 150 μM HIP and Optimized HIP peptides for 48 hours, demonstrating the translocation of the HIP receptor from the cell membrane of PANC-1 cells to the cytoplasm upon stimulation with HIP and Optimized HIP.

FIG. 13 demonstrates PANC-1 cells treated with trypsin and incubated in serum free medium differentiate into islet cell aggregates. HIP receptor is upregulated during differentiation of human pancreatic cells and appears to interact with HIP2 and HIP2B interact with HIP receptor. HIP2 and Optimized HIP2B stimulated traffic from the HIP receptor on the cytoplasmic membrane into the nucleus of the cells stimulating differentiation of pancreatic progenitor cells into insulin-producing new islets.

Figure 14:
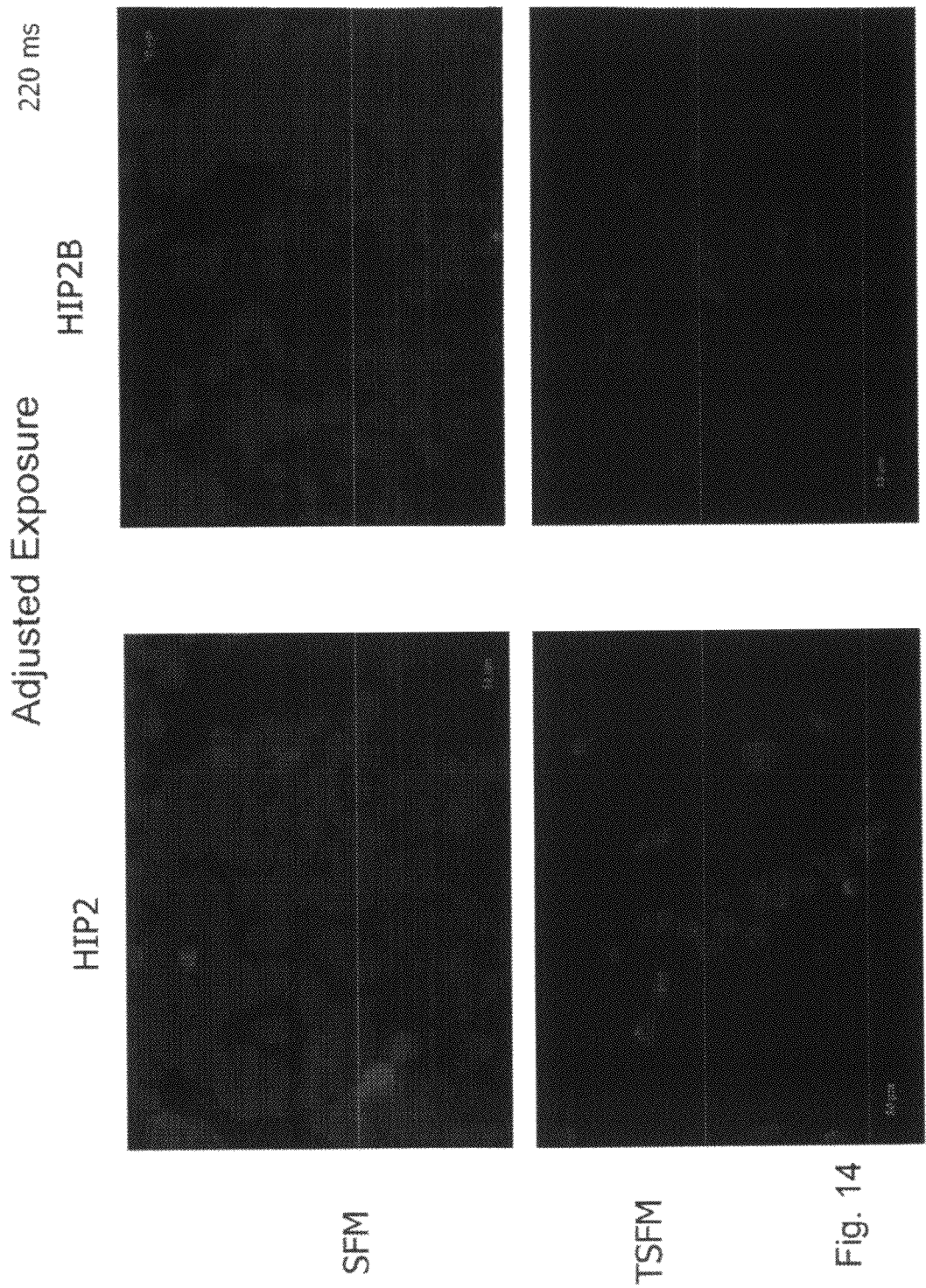
FIG. 14 demonstrates exposure adjusted PANC-1 cells in SFM and TSFM with HIP and Optimized HIP2B peptides.

FIG. 14 demonstrates rabbit anti-human HIP receptor antibody labeled with Cy3 in (A) TSFM alone and (B) TSFM with 150 μM (Optimized HIP2B) for 48 hours. HIP stimulates the receptor membrane bound protein to be engulfed by the cytoplasmic membrane and transported to the nuclear membrane.

Figure 15:
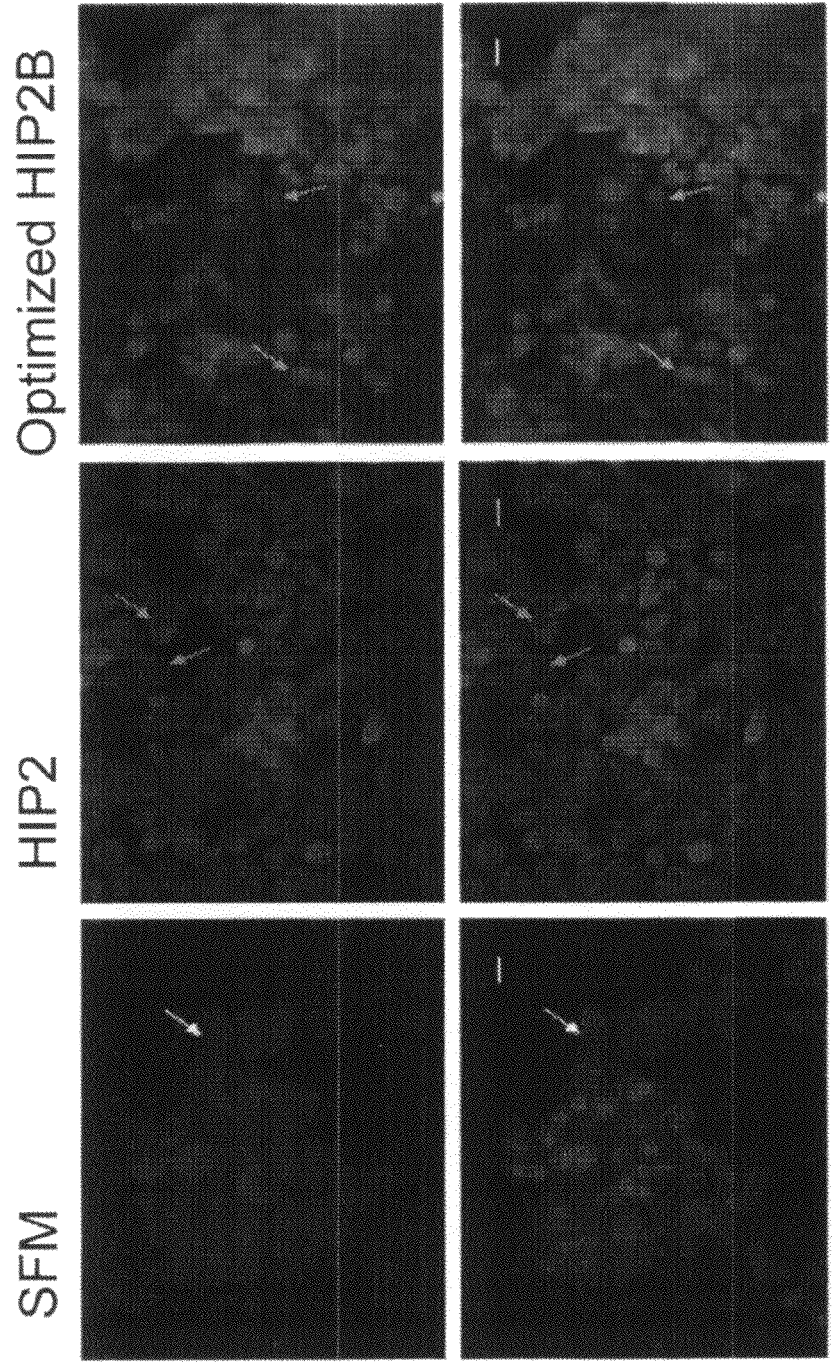
FIG. 15 demonstrates repeat evaluation of the impact of Optimized HIP2 peptides on PANC-1 cells utilizing immunofluorescent analyses indicating that HIP2B interacts with the HIP receptor (EXTL) resulting in engulfment of the HIP receptor from the cytoplasmic membrane into the cytoplasm to the nucleus upon stimulation with HIP.

FIG. 15 demonstrates repeated immunofluorescent analyses of the impact of Optimized HIP2B on the HIP receptor (EXTL3). The upper panels indicated by the Cy3 immunofluorescent staining of EXTL3 (red). In the lower panel of images the Cy3 immunostaining of EXTL3 has been overlaid with DAPI (blue) staining of the nuclei. Cells were grown in standard growth medium as a control and compared to cells grown serum-free medium (SFM) in the presence or absence of HIP. The yellow arrows demonstrate examples of the surface expression of EXTL3 grown in standard growth medium. The cell borders are well-defined indicating surface expression of EXTL3 on the plasma membrane. The yellow arrows delineate the cell borders while the nuclei are shown in blue. The middle images are cells grown in SFM. EXTL3 is localized in the cytoplasm as indicated by cytoplasmic Cy3 staining. The green arrows show the lack of staining in the position of the nuclei. The green arrows in the lower image of cells grown in SFM demonstrate intense blue DAPI staining of the nuclei indicating a lack of EXTL3 in the nucleus. In the upper image of the cells grown in SFM and HIP, the presence of EXTL3 immunostaining in the nucleus indicated by the blue arrows suggests a translocation of EXTL3 into the nucleus. In the lower image of cells grown in SFM and HIP, the blue arrows indicate the position of the nuclei. In the lower image there is an overlap of EXTL3-Cy3 staining and nuclear DAPI staining that corroborates the nuclear localization of EXTL3 (blue arrows). Scale bar=20 μm in all images.

Figure 16:
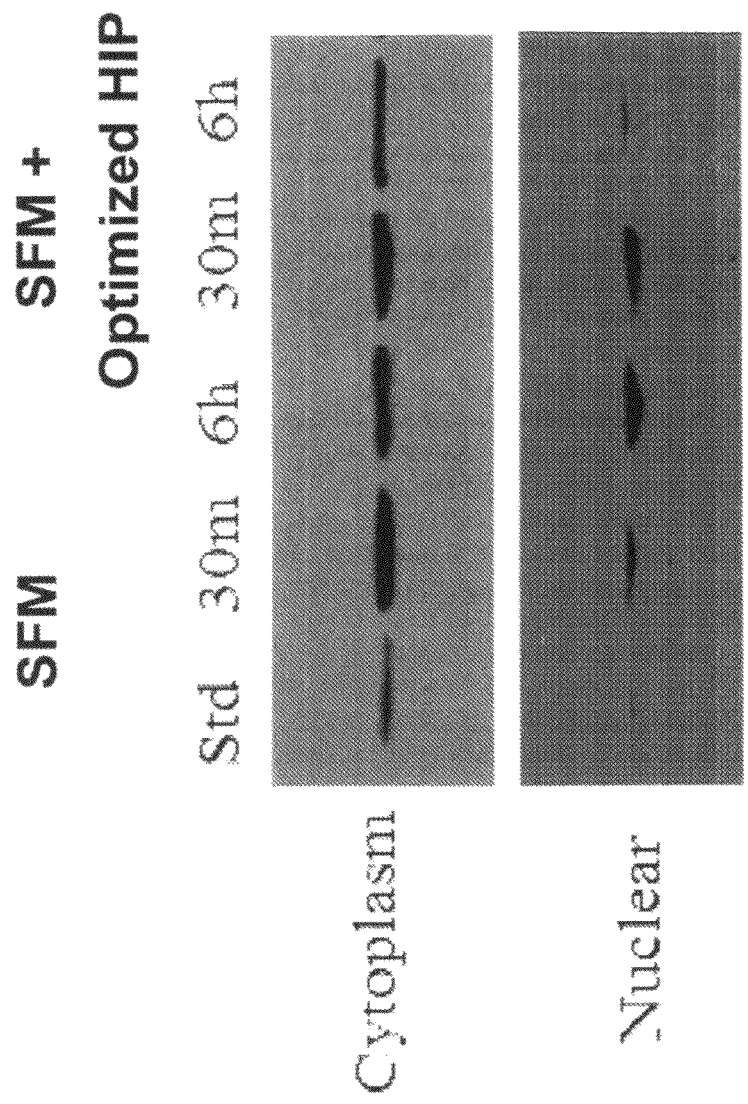
FIG. 16 demonstrates a western blot of Optimized HIP2B enhances HIP receptor (EXTL3) translocation time from the cytoplasmic membrane to the nucleus in PANC-1 cells.

FIG. 16 demonstrates Optimized HIP2B enhances HIP receptor (EXTL3) translocation from the cytoplasmic membrane to the nucleus in PANC-1 cells. Western blot analysis of HIP (EXTL3) levels in cytosolic and nuclear fractions isolated at the indicated time points. Western blot analysis demonstrates higher nuclear levels of HIP receptor (EXTL3) were observed at 6 hours after culture in SFM without HIP. Addition of HIP2 and HIP2B in culture media enhanced EXTL3 nuclear translocation, demonstrated by higher nuclear levels of this protein at 30 minutes. These comparisons demonstrate that in the presence of HIP, there is enhanced the translocation time of EXTL3 from the cytoplasmic compartment to the nucleus and that EXTL3 nuclear translocation can be modulated by both the presence of HIP Western blots are repeated results using these cells and time points.

EXAMPLE 12

In a randomized, placebo-controlled study of HIP2, HIP2B v. placebo, eighty (80) mice were treated with STZ to induce diabetes. Mice were monitored until they reached a level of hyperglycemia consistent with the onset of diabetes. Baseline glucose levels for intervention mice averaged 300+/−6 mg/dL and there were no statistically significant differences in the glucose levels among the HIP intervention groups and the placebo group (p=0.301).

After 36 days, all HIP treated mice are off insulin and glucoses have trended downward significantly as compared to the placebo group. Randomly selected mice were sacrificed during the course of the study the immunohistochemistry on their pancreata. C-peptide analyses on serum are underway. After 39 days of intervention, the remaining mice will be tested daily for glucose levels and overall health for the next 60 days.

Preliminary evaluation demonstrates that HIP treatment results in a 38.7% reduction as compared to placebo (p<0.05). In addition, the stabilization of HIP2 to formulate HIP2B did not decrease the activity in vivo.

Figure 17:
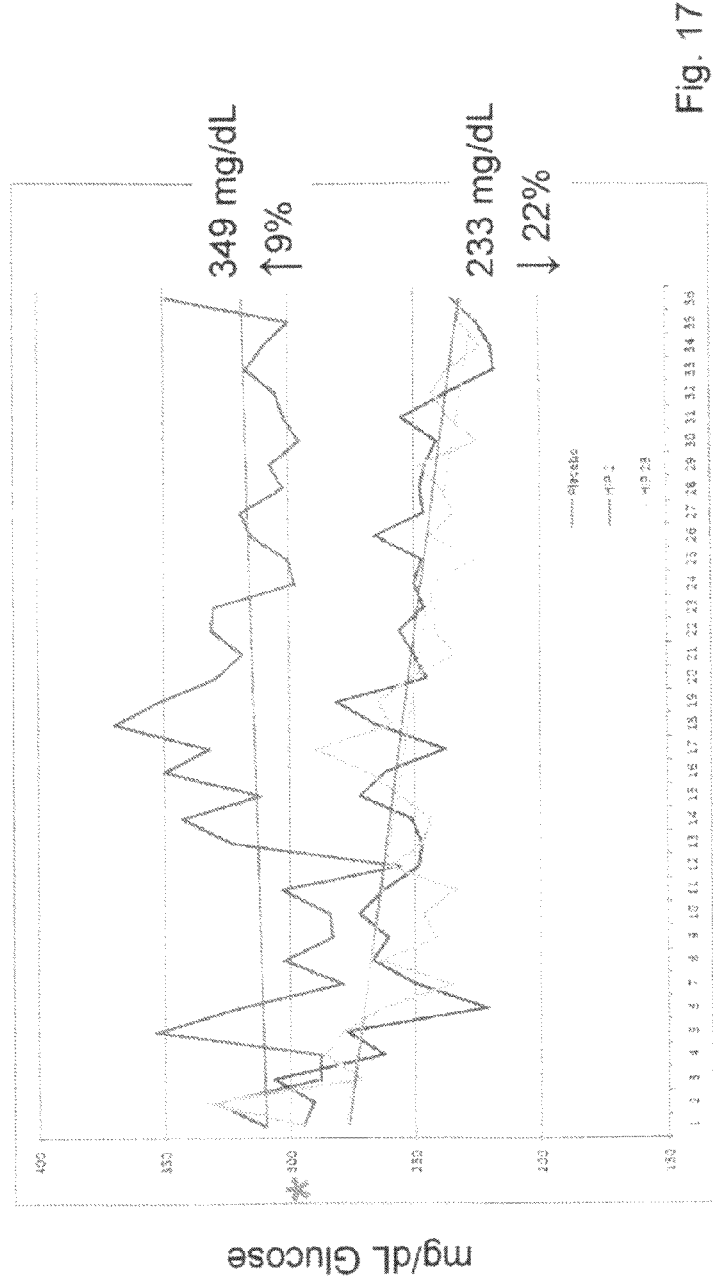
FIG. 17 is a graph depicting the average daily glucose levels in an STZ-Diabetic Mouse Model following administration of HIP2, HIP2B and placebo.

As shown in FIG. 17, HIP treatment resulted in glucose levels that were 116 mg/dL lower than placebo (↓38.7% p<0.05). All HIP treated mice came off of insulin. 56% (9/16) of HIP-treated mice had glucose levels <230 mg/dL. 9% (1/11) of placebo-treated mice had glucose levels <230 mg/dL. HIP 2B is significantly more a more stable in vitro in serum at 37 degrees. HIP 2B has a longer half-life in saline also. Modifications to HIP 2 to form HIP 2B have not diminished activity in vivo.

To evaluate the therapeutic potential of HIP2B, a STZ-induced diabetes mouse model was utilized. Sixty C57BL/6J mice were injected intraperitoneally with STZ at 50 mg/kg in citrate buffer, pH 4.5, for 5 consecutive days to render them diabetic. Mice were randomized into the study when the blood glucose level was ≥200 mg/dl for two consecutive days. Blood glucose was monitored daily using a drop of blood collected from a nick made on the tip of the tail. Glucose measurements were determined using a glucose meter. If the blood glucose level in any animal rose to ≥324 mg/dL, the animal was treated with insulin (1 Unit per day, glargine insulin, intramuscularly) until blood glucose dropped below 324 mg/dL. A record was kept of insulin dosing, so that insulin requirement comparisons could be performed. An additional 3 animals were not treated with STZ and were used to establish non-diabetic baseline values.

Animals were assigned into three groups, as shown in Table 4. Diabetic animals were injected intraperitoneally twice daily (am and pm) for 39 consecutive days with either vehicle control, HIP2 (300 μg) or HIP2B (300 μg). Mice from each of the treatment arms (Groups 1-3) were sacrificed on Day 39. On the evening prior to sacrifice, all mice were fasted with a morning glucose level measured prior to sacrifice, which was considered as a fasting glucose level. The remaining animal groups were maintained with no medical intervention from Day 40-60. They received daily morning glucose measurements and insulin administration, when appropriate. Study endpoints included the following: 1) changes in blood glucose and 2) changes in insulin requirements.

TABLE 4

Randomization of STZ-rendered diabetic mice

| Group | Treatment | Dosage | Dose Level | Dose Volume | Number of Animals |
| --- | --- | --- | --- | --- | --- |
| 1 | Vehicle | 2 IP injections daily × 39 days | 0 | 100 μl | 20 |
| 2 | HIP2 | 2 IP injections daily × 39 days | 300 μg | 100 μl | 20 |
| 3 | HIP2B | 2 IP injections daily × 39 days | 300 μg | 100 μl | 20 |

Over the course of the study, both HIP2 and HIP2B groups had a significant decrease in blood glucose levels from the control group. There was, however, no difference in blood glucose level between the two HIP groups. FIG. 17 demonstrates that by day 36, Modifications to HIP 2 to form HIP 2B have not diminished activity in vivo. HIP treatment resulted in glucose levels that were 116 mg/dL lower than placebo (↓38.7% p<0.05). All HIP treated mice came off of insulin. Fifty-six (56) % (9/16) of HIP-treated mice had glucose levels <230 mg/dL. Nine (9) % (1/11) of Placebo-treated mice had glucose levels <230 mg/dL.

FIG. 17 is a graph depicting the average daily glucose levels in an STZ-Diabetic Mouse Model following administration of HIP2, HIP2B and placebo. The mean baseline glucose level was 300 mg/dL±2 mg/dL with no significant differences between the placebo or HIP-treated groups (p=0.301).

Figure 18:
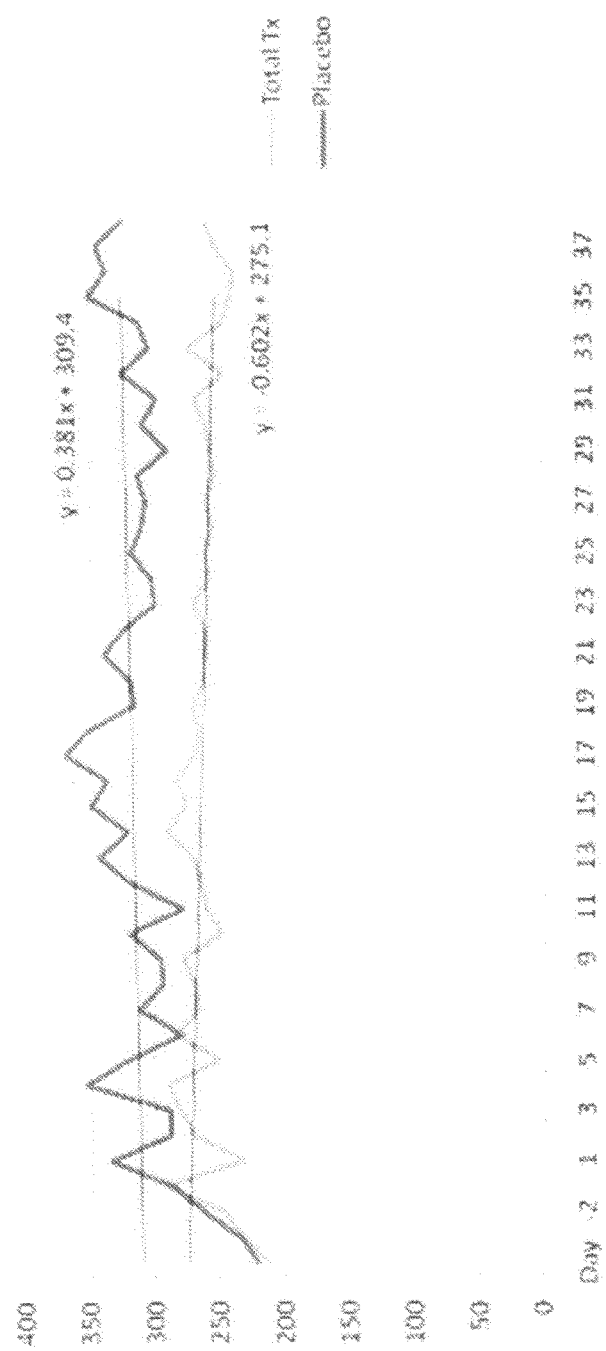
FIG. 18 is a graph depicting the daily glucose levels among HIP2B treated (green) and control (purple) and placebo groups of mice.

FIG. 18 is a graph depicting the daily glucose levels among HIP2B treated (green) and control (purple) and placebo groups of mice. The slopes of the lines of each group (FIG. 18) represent the rate of change in glucose levels, which we refer to as "regeneration speed." HIP2B treatment resulted in rate of fall (regeneration speed) in glucose levels of −0.602 as compared to rate of rise in glucose in levels within the placebo-treated group having a rate of rise in glucose of +0.381 over the course of the study from days 1-39.

Figure 19:
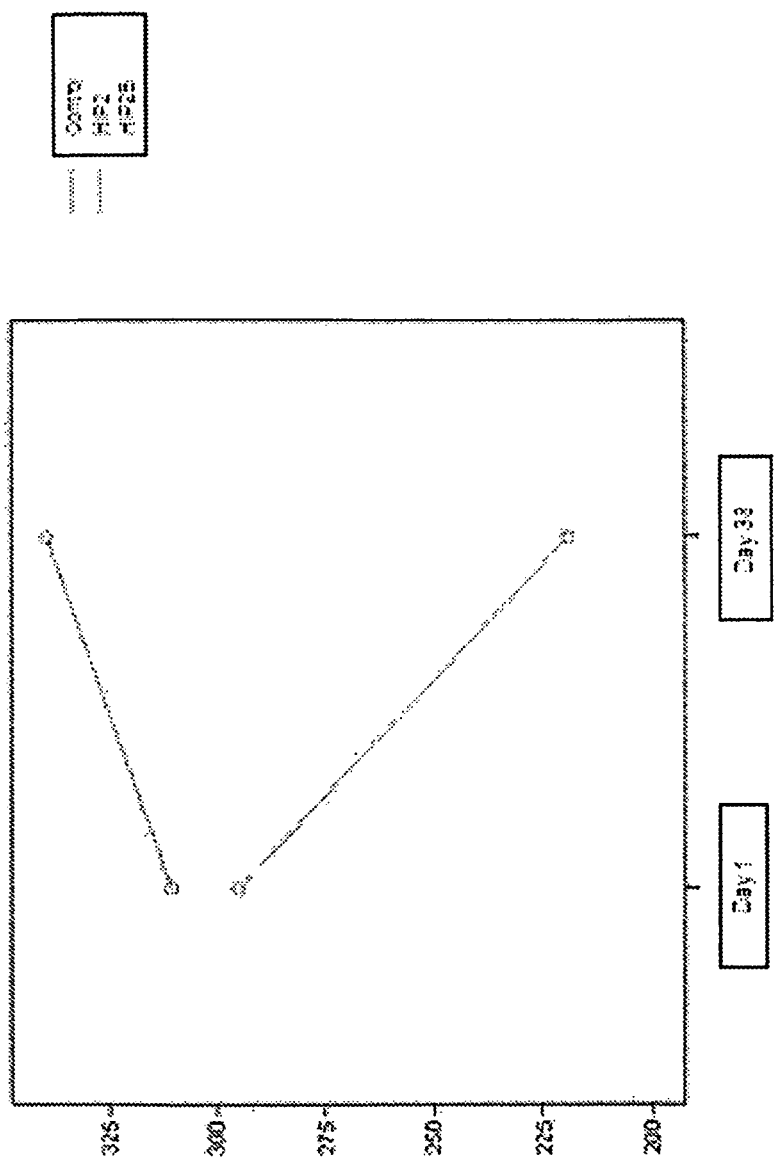
FIG. 19 is a graph depicting the glucose levels among HIP2B (yellow), HIP2 (green) and control (blue) treated groups of mice at the beginning and end of intervention.

FIG. 19 demonstrates the differences in glucose between day 1 and day 38 of the study comparing HIP2B, HIP2 and placebo. FIG. 19 demonstrates the improved glucose control among Optimized HIP2B recipients (yellow), HIP2 (green) and control (blue) treated groups of mice at the beginning and end of intervention. The control group had a mean increase from baseline by 28.9 mg/dL to 334.6 mg/dL. The HIP2B and HIP2 groups had significant reductions from baseline with a mean nonfasting glucose of 235.3 mg/dL in the HIP2B group (p=0.024 from control) and 231.6 mg/dL in the HIP2 group (p=0.029 from control).

Figure 20:
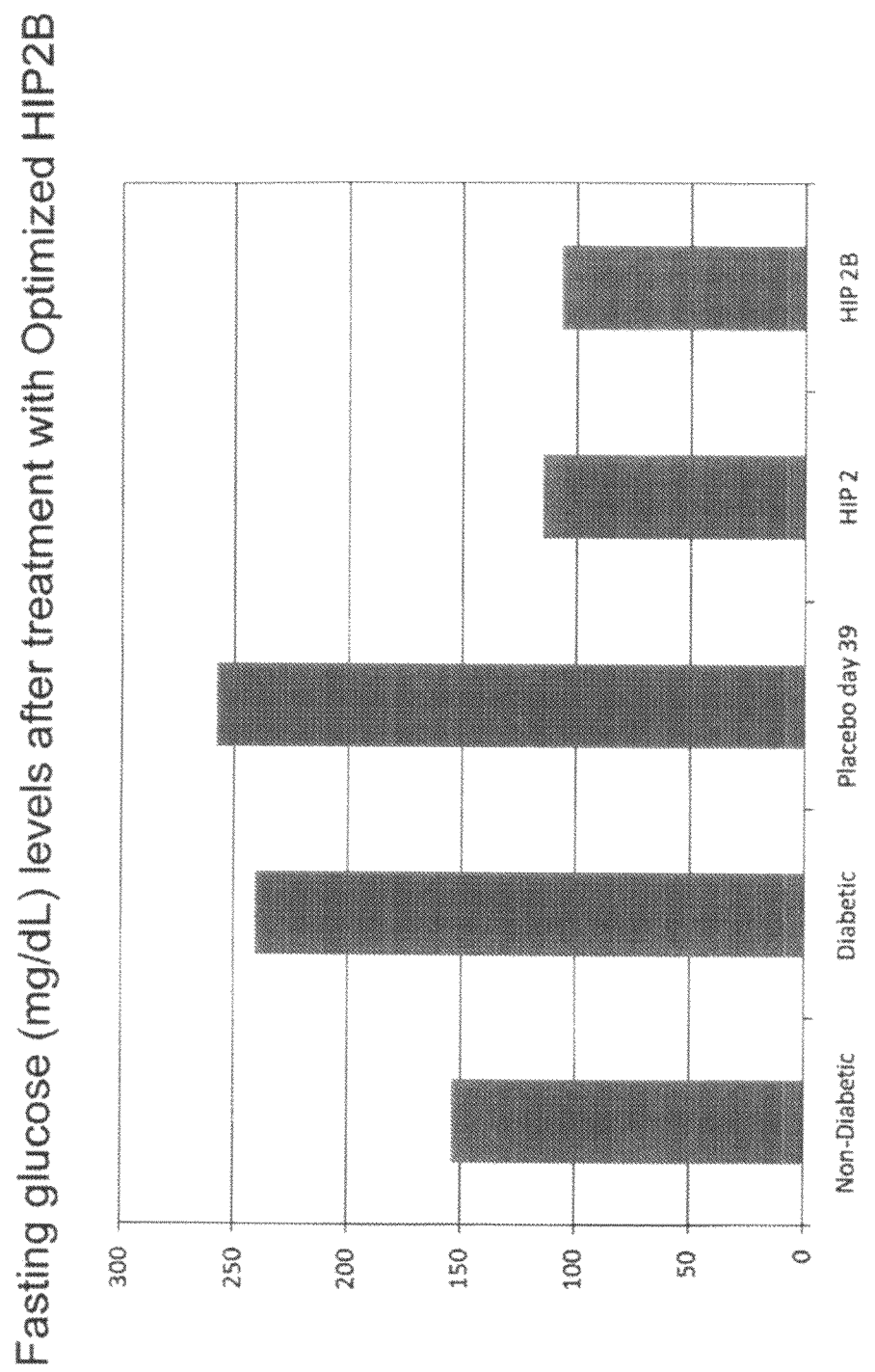
FIG. 20, demonstrates the impact of Optimized HIP2B restoring fasting glucose levels to nondiabetic ranges and to levels below that of baseline glucose levels prior to STZ treatment.

FIG. 20 demonstrates fasting glucose levels at the study close between treatment groups. The Optimized HIP2B treatment group had a fasting glucose at study end of 106.7 mg/dL±0.58 mg/dL (p=0.046) compared to placebo-treated controls with a mean fasting glucose of 258.00±84.5 mg/dL. The unblocked HIP2-treated mice had a mean fasting glucose of 115.3 mg/dL±16.5 mg/dL (p=0.050) compared to the placebo-treated group.

Figure 21:
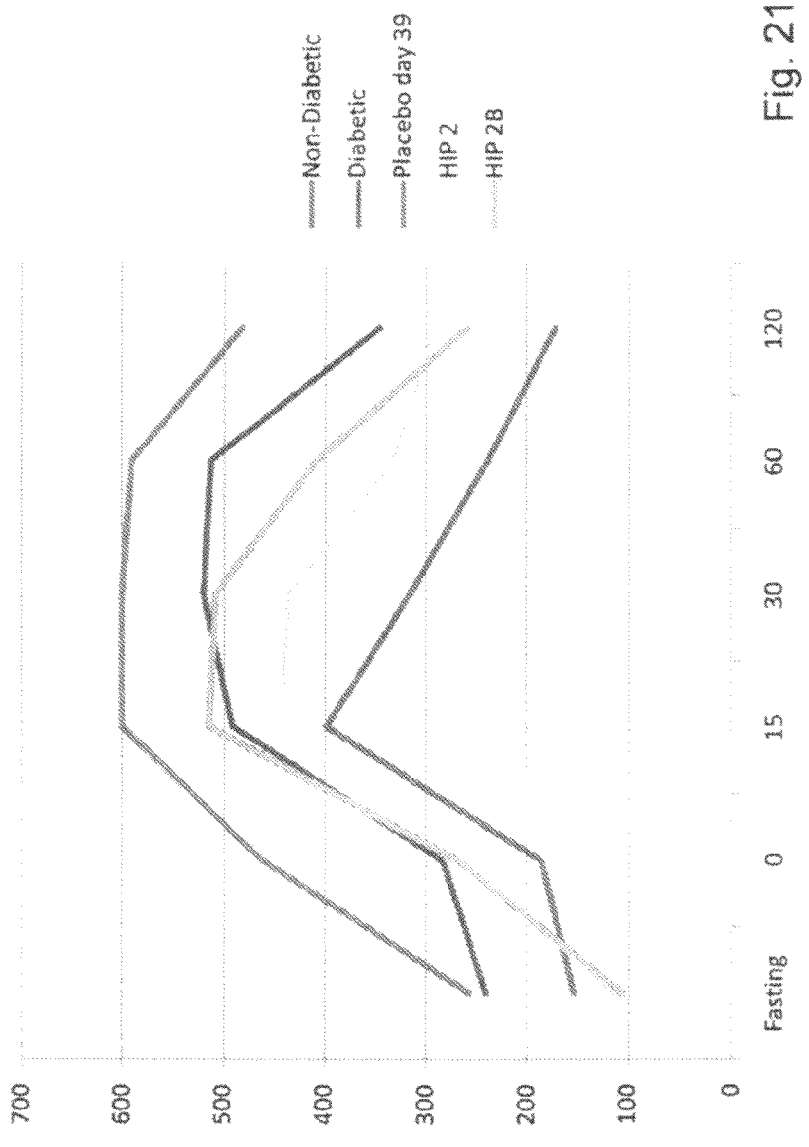
FIG. 21 demonstrates the results of glucose tolerance testing among treatment groups at the close of the study with lower glucose levels seen in the Optimized HIP2B treatment group.

FIG. 21 demonstrates the results of glucose tolerance testing performed on animals following the treatment course and prior to sacrifice. Optimized HIP 2B is significantly more a more stable in vitro in serum at 37 degrees. Optimized HIP 2B has a longer half-life in saline also. Modifications to HIP 2 to form HIP 2B have not diminished activity in vivo

EXAMPLE 13

Figure 22:
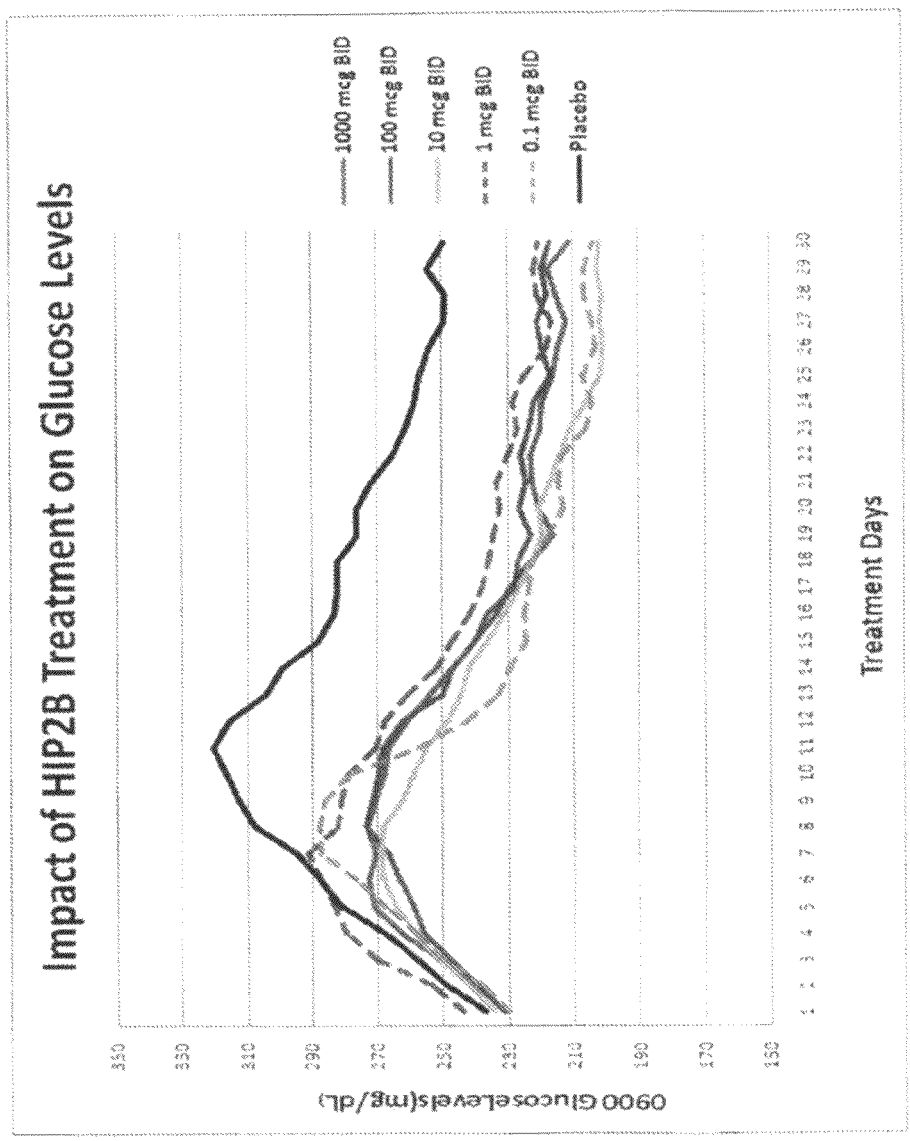
FIG. 22 demonstrates a dose response analysis study of Optimized HIP2B in STZ-rendered diabetic mice to compare the effects of Optimized HIP2B on glucose control when delivered at differing dosages in a diabetes model in mice in order to determine the lowest potential dosage that produces the maximum efficacy.

To evaluate the therapeutic potential and lowest efficacious dose of HIP2B necessary to significantly improve glycemic control, a dose-response study utilizing STZ-induced diabetes mouse model was conducted FIG. 22 demonstrates the results of a dose response analysis of HIP2B conducted to evaluate and compare the effects of Optimized HIP2B on glucose control when delivered at differing dosages in a diabetes model in mice in order to determine the lowest potential dosage producing the maximum efficacy. This study was a randomized trial to determine the impact of five concentrations of HIP2B on glycemic control and attenuation of diabetes in an STZ-treated mouse model. Treatment groups ranged from a maximum of 1000 micrograms BID to 0.1 micrograms BID of Optimized HIP2B in 100 ul of isotonic saline. The six study groups are listed below.

| Test Article | Equivalent Dosage in Man (60 kg) | Mouse Dose day = mg · kg · day (mouse weight <20 grams) |
|---|---|---|
| 1 | 100 mg kg day 6000 mg day | 1000 mcg 100 μl BID = 2 mg day = 100 mg kg · day |
| 2 | 10 mg kg day 600 mg · day | 100 mcg 100 μl BID = 0.2 mg · day = 10 mg · kg day |
| 3 | 1 mg kg day 60 mg. day | 10 mcg 100 μl BID = 0.02 mg · day = 1 mg kg day |
| 4 | 0.1 mg kg day 6 mg day | 1 mcg 100 ul BID = 0.002 mg · day = 0.1 mg · kg day |
| 5 | 0.01 mg kg · day 0.6 mg day | 0.1 mcg 100 ul BID = 0.0002 mg day = 0.01 mg kg day |
| 6 | Saline placebo | Saline placebo 100 μl BID |

Glucose levels were checked daily in mice at ~0900-1100, independent of feeding patterns in the mice. Because of the potential glucose variations at the time of the daily glucose measurements, five-day moving average glucose values were calculated daily in each treatment group. The impact of HIP2B concentrations was evaluated by 1) the average glucose levels and 2) the extent to which the differing concentrations of HIP2B attenuated the development of glucose toxicity as determined by the glycemic excursions among intervention groups compared to the control group.

FIG. 22 depicts the dose response study conducted in STZ-treated mice and confirms that the efficacy among diabetic mice treated with 10, 100 and 1000 micrograms BID are equivalent. At less than 1 mg/kg dosing there was a diminished efficacy signal in mice which corresponds to a 0.1 and 0.01 mg/kg dose levels.

Optimized HIP2B is distinct in many ways from traditional therapies such as insulin for the treatment of diabetes. HIP2B initiates a signaling cascade leading to islet neogenesis. In contrast to insulin, in which the efficacy of the response is measured primarily by its immediate glucose-lowering capacity, the pharmacodynamic response of any islet neogenesis agent is measured over days and weeks. Thus, the efficacy of islet neogenesis agents such as HIP2B and INGAP may be evaluated not only by long term restoration of glycemic control following repeated daily dosing, but also by the attenuation of hyperglycemia, and/or the rate at which euglycemia is achieved. All HIP treatment groups approached euglycemia.

The dose attenuation response was calculated as the change in average glucose with the greatest attainable response equal to the maximum extent to which diabetes is attenuated. In this evaluation, we report the change in response per unit dose as calculated by the difference in maximal glycemic excursions in each treatment group throughout the study compared to that of the control group's glycemic excursions. The control group had no disease attenuation and achieved 100% disease induction. The extent to which the HIP2B doses attenuated this effect is described as the % attenuation of disease in each treatment group relative to the placebo group.

FIG. 23 depicts the impact of differing concentration of HIP2B on the attenuation of diabetes. Each of the three highest treatment levels attenuated the severity of diabetes to the same extent. The two lowest treatment dosage of HIP (0.1 and 1 microgram per day delivered BID) did not demonstrate as optimal a response as did the three higher dosages.

At dosage levels 0.1 and 1 micrograms BID, the HIP2B response demonstrated disease attenuation over that of the placebo. As the HIP2B concentration increased to 10 micrograms BID, the greatest efficacy and attenuation of diabetes resulted. At dose levels 1000, 100, and 10 micrograms BID, diabetes was attenuation between 60-70% of the maximum disease state seen in the placebo group. From these results, we conclude that the lowest dose level of HIP2B that will provide optimal efficacy in is in the range of 1-10 micrograms BID in mice or a human dose equivalent of 0.5-1.0 mg/kg in humans (30-60 mg BID). This dose is about $\frac{1}{10}$ of the dosage used in the Phase2B INGAP trials (600 mg/day).

EXAMPLE 14

A pharmacokinetic study was undertaken to confirm the improvement in bioavailability that was achieved with the Optimized HIP2B structure. The absolute bioavailability and pharmacodynamic study was conducted in Sprague Dawley rats following intravenous and subcutaneous dose administration of HIP2 (FIG. 24), Optimized HIP2B and INGAP. The purpose was to determine the absorption, absolute bioavailability and plasma levels of HIP2, Optimized HIP2B and INGAP in male rats following two different routes of administration.

Six Groups of five male Sprague Dawley rats were administered HIP2, HIP2B or INGAP by intravenous and subcutaneous routes as follows in table below.

| Group | Route of Administration | Test Article | Nom Conc. (mg/ml) | Dose Vol (ml/kg) | Nom Dose Level (mg/kg) |
|---|---|---|---|---|---|
| 1 | Subcutaneous | HIP2 | 2 | 2 | 4 |
| 2 | Intravenous | HIP2 | 2 | 2 | 4 |
| 3 | Subcutaneous | HIP2B | 2 | 2 | 4 |
| 4 | Intravenous | HIP2B | 2 | 2 | 4 |
| 5 | Subcutaneous | INGAP | 2 | 2 | 4 |
| 6 | Intravenous | INGAP | 2 | 2 | 4 |

Ten serial blood plasma samples (0.03 ml each) were collected from a jugular vein catheter from five animals per group at 5, 10, 15, 30 minutes, 45 minutes followed by samples at 1, 2, 3, 8, and 24 hours post-dose. Plasma was collected into tubes containing EDTA. Following collection, samples were kept chilled on cool packs before centrifugation and transfer to pre-labeled microfuge tubes for storage at −70° C. or below.

Rat plasma samples of 200 μl each were added to a micro centrifuge tube containing 1 ml of acetonitrile (0.07% trifluoroacetic acid, TFA) and stirred with a vortex mixer for 1 min. followed by centrifugation to remove precipitated plasma proteins. The supernatant solution was removed and evaporated, using a Speed Vac, to dryness. To the micro centrifuge tube containing the dry pellet was added 200 μl of 20:80 acetonitrile:water (containing 0.07% TFA). The sample was centrifuged to remove any insoluble material and the supernatant solution transferred to analytical vials for LC/MS MS analysis. The mass spectrometer was calibrated to detect the most abundant daughter ion/ions observed for each of the respective reference samples of HIP2B (M=286.0), HIP2 (M=287.1) and INGAP (M=212.2, 356.1, 373.9). Optimized HIP2B, HIP2 and INGAP plasma samples were analyzed on a C-18 reverse phase column (50 mm×2.0 mm, Varian Pursuit XRS3) using 0.07% TFA in $H_2O$ as buffer A and 0.07% TFA in acetonitrile as buffer B. A linear gradient of 98% A/2% B progressing to 100% B over 9 minutes was used at a flow rate of 0.4 ml/min.

The following plasma controls were treated as described above and used to establish a standard concentration curve:
1. Blank plasma as a background control
2. Five standard plasma samples containing $6.7\times10^4$, $6.7\times10^3$, $6.7\times10^2$, 6.7 and 6.7 ng/ml of HIP2B, HIP2 and INGAP Retained dosage samples of Optimized HIP2B, HIP2 and INGAP were also analyzed by LC/MSMS in order to determine the concentration of each at the time of injection. Analysis confirmed the concentration, within experimental error, to be 2 mg/ml. All animals appeared normal at all times post-dosing and following each route of administration. HIP2 and INGAP: Following intravenous or subcutaneous administration of HIP2, very low levels of HIP2 were observed only at five minutes post dosage with all subsequent samples being below the limit of quantitation. Following intravenous or subcutaneous administration of INGAP, all plasma samples measured were below the lower limit of quantitation. As a result, the plasma pharmacokinetic parameters for HIP2 and INGAP following intravenous and subcutaneous dose administration could not be calculated.

Following intravenous administration of HIP2B, HIP2B plasma concentrations declined in a monophasic manner, with a mean terminal phase plasma half-life of 0.19 hours (11 minutes). Mean $C_{max}$ was 8237 ng/ml which occurred at the first sampling time point of 5 minutes. Mean C0 was estimated to be 18805 ng/ml. Mean $AUC_{0-\infty}$ was 2231 ng*hr/ml. Apparent mean plasma clearance was 1.9 l/hr/kg with an apparent mean volume of distribution of 0.48 l/kg.

Figure 25:
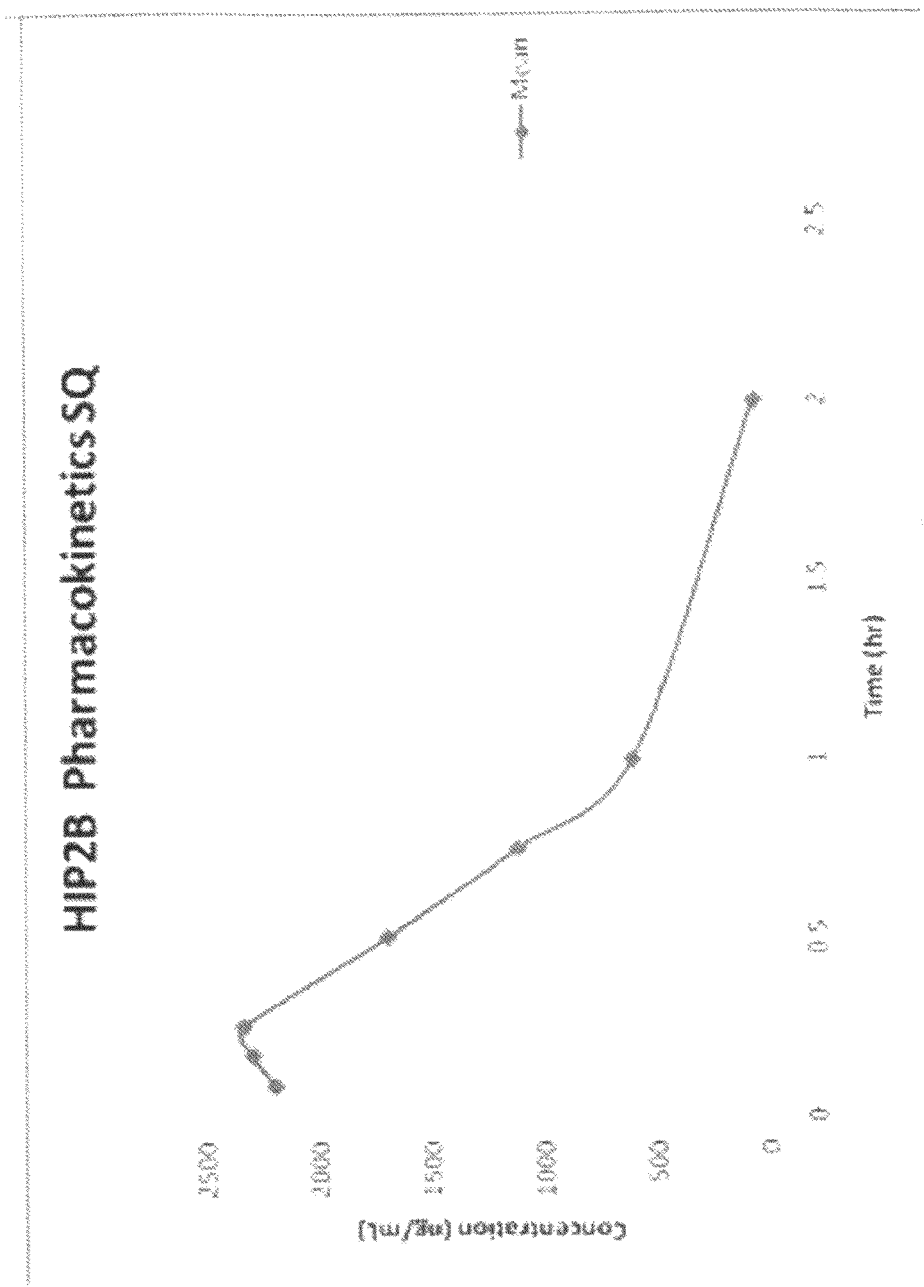
FIG. 25 demonstrates the pharmacokinetic analysis of Optimized HIP2B delivered subcutaneously.

Following subcutaneous administration of Optimized HIP2B, absorbed HIP2B declined in a monophasic manner with a mean terminal phase plasma half-life of 0.34 hours (20 minutes). Mean $AUC_{0-\infty}$, was 1932 ng*hr/ml. Apparent mean Cl/F was 2.1 l/hr/kg with an apparent mean $V_2/F$ of 1 l/kg. The absolute subcutaneous bioavailability of HIP2B was 87%. FIG. 25 demonstrates that pharmacokinetics of subcutaneous administration of Optimized HIP2B, Optimized HIP2B plasma levels were detectable up to 2 hours with a $t_{1/2,e}$ of ~20 minutes.

INGAP plasma concentrations were undetectable at any time point indicating that INGAP is rapidly cleared and/or metabolized.

Optimized HIP2B plasma levels are significantly higher relative to HIP2 or INGAP following subcutaneous dose administration. Based on the observed multi-peak LC/MS chromatographic plasma profiles, Optimized HIP2B is much less likely to be rapidly metabolized in vivo compared to HIP2 and INGAP. The bioavailability of HIP2B is 87%.

Figure 24:
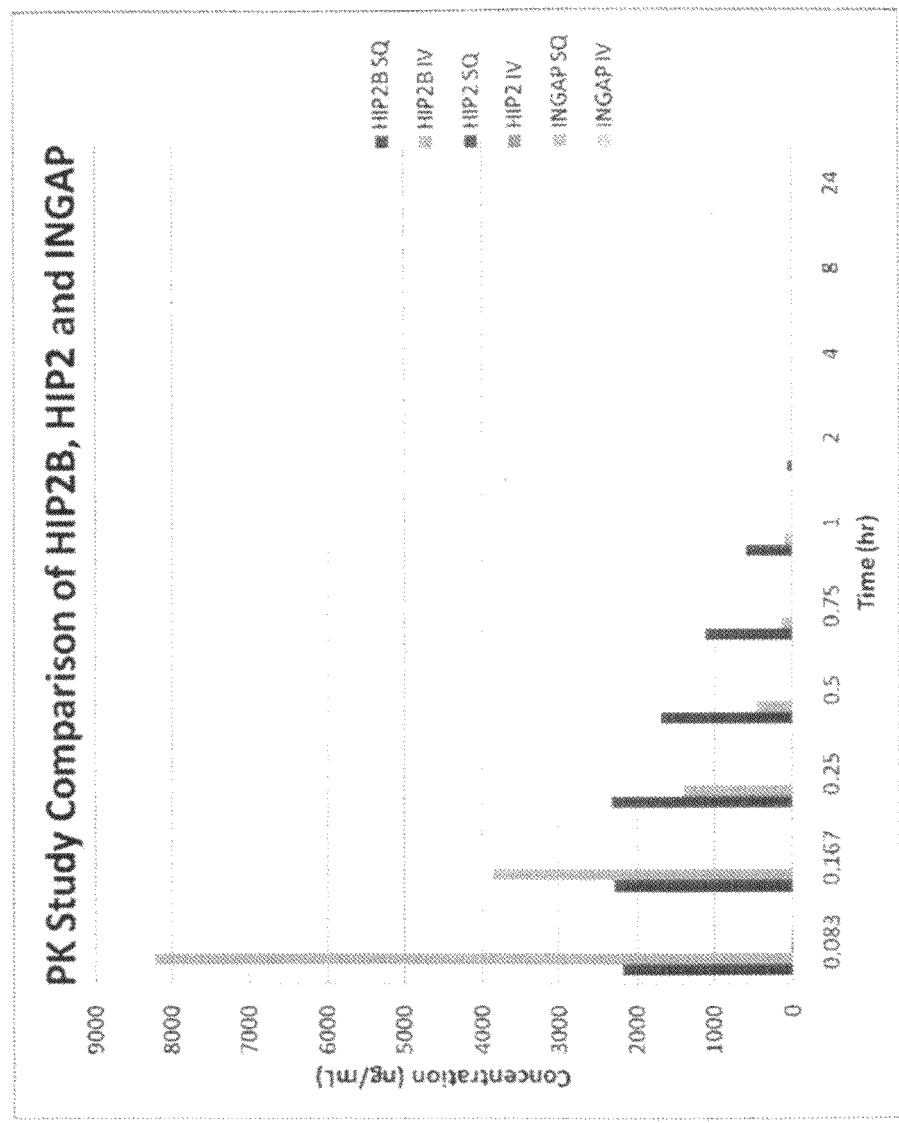
FIG. 24 demonstrates the pharmacokinetic analysis of HIP2B, HIP2 and INGAP post subcutaneous and intravenous administration to Sprague Dawley rats at 4 mg/kg.

FIG. 24 demonstrates the LC/MS MS analysis of Optimized HIP2B, HIP2 and INGAP samples derived from rat plasma as part of a PK analysis in which HIP2B, HIP2 and INGAP were dose administered by subcutaneously or via intravenous injection at 4 mg/kg.

Following subcutaneous administration, HIP2B levels were detectable up to 1.5 hrs. The $T_{1/2}$ is approximately 0.5 hrs. Very low levels of HIP2 were detected at 5 minutes with no subsequent detection post 5 min. Based on the observed multi-peak LC/MS chromatographic profile of optimized HIP2B is less rapidly metabolized in vivo compared to HIP2.

Concentrations of INGAP were undetectable at any time point, indicating that it is rapidly cleared and or metabolized. The below table summarizes this data.

| | | | | | | | | | |
|---|---|---|---|---|---|---|---|---|---|
| Comparative PK Analysis | | | | | | | | | |
| Peptide | Route | Dose (mg/kg) | $C_0$ (ng/ml) | $C_{max}$ (ng/ml) | $T_{max}$ (h) | $C_{1h}$ (ng/ml) | $AUC_{(0-\infty)}$ (ng * h/ml) | $T_{1/2}$ (h) | F |
| HIP2B | SQ | 4 | na | 2739 | 0.167 | 611.5 | 1932 | 0.34 | 0.87 |
| | IV | 4 | 18805 | 8237 | 0.083 | 114 | 1614.3 | 0.19 | na |
| HIP2 | SQ | 4 | na | 32 | 0.083 | 0 | 2.7 | 0.02 | 0.01 |
| | IV | 4 | 18805 | 29 | 0.083 | 0 | 441.9 | 0.02 | na |
| INGAP | SQ | 4 | na | 0 | na | 0 | 0.0 | <0.025 | 0.00 |
| | IV | 4 | 18805 | 0 | na | 0 | 439.5* | <0.025 | na | n = 5;
na, not applicable,
*extrapolated

We conclude that plasma levels of optimized HIP2B are significantly higher relative to HIP2 or INGAP following subcutaneous administration administration.

HIP2B plasma levels are significantly higher relative to HIP or INGAP following IV administration. Following intravenous injection, optimized HIP2B shows a time dependent depletion with undetectable concentrations by 45 min. The $T_{1/2}$ is approximately 9 minutes. HIP2 was observed only at the 5 minute time point and INGAP was undetectable at any time point, indicating that both are rapidly cleared and or metabolized.

Although the present invention has been described in considerable detail with reference to certain preferred embodiments thereof, other versions are possible. Therefore the spirit and scope of the appended claims should not be limited to the description and the preferred versions contained within this specification.

We claim:

1. A peptide consisting of the sequence of SEQ ID NO: 7 (HIP2B).

2. A pharmaceutical composition comprising a peptide consisting of the sequence of SEQ ID NO: 7 (HIP2B).

3. The pharmaceutical composition of claim 2, wherein said peptide is present in a therapeutically effective amount.

4. The pharmaceutical composition of claim 3, wherein said therapeutically effective amount is selected from the group consisting of about 20 mg and about 30-60 mg.

5. The pharmaceutical composition of claim 3, wherein said therapeutically effective amount is equivalent to a dose selected from a group consisting of about 0.5 to about 5 mg/kg, about 0.5 to about 1.0 mg/kg, about 0.1 mg/kg, about 0.5 mg/kg, about 1.0 mg/kg, about 5 mg/kg, and 8-20 mg/kilogram.

6. The pharmaceutical composition of claim 3, wherein the therapeutically effective amount is from about 400-800 mg per day, 60 to about 180 mg/day, or from about 60 to about 120 mg/day.

7. The pharmaceutical composition of claim 2 further comprising a pharmaceutically acceptable excipient.

8. A method of treating type 2 diabetes in a subject in need thereof comprising administering to the subject the peptide of claim 1.

9. A method of treating type 2 diabetes in a subject in need thereof comprising administering to the subject a pharmaceutical composition comprising a peptide consisting of the sequence of SEQ ID NO: 7 (HIP2B).

10. The method of claim 8, wherein said peptide is administered in a therapeutically effective amount.

11. The method of claim 9, wherein said pharmaceutical composition comprises a therapeutically effective amount of the peptide.

12. The method of claim 8, further comprising administering a pancreatic islet cell regeneration agent, wherein said agent is selected from the group consisting of amylin, pramlintide, exendin-4, GIP, GLP-1, GLP-1 receptor agonists, GLP-1 analogs, hamster INGAP peptide, liraglutide, dipeptidyl peptidase inhibitor and combinations thereof.

13. The method of claim 9, further comprising administering an agent selected from the group consisting of: teplizumab, abatacept, rapamycin, FK506, IL-2, aldesleukin, lisofylline (1-[(5R)-5-Hydroxyhexyl]-3,7-dimethyl-3,7-dihydro-1H-purine-2,6-dione), interferon-alpha, diazoxide, a statin, mycophenolate mofetil, daclizumab, rituximab; campath-1H, polyclonal anti-T-lymphocyte globulin, pegfilgrastim, vitamin D, anakinra, deoxyspergualin and combinations thereof.

14. The method of claim 13, wherein the statin is atorvastatin.

15. The method of claim 11, wherein the therapeutically effective amount is about 20 mg.

16. The method of claim 11, wherein the therapeutically effective amount is about 30 to about 60 mg.

17. The method of claim 11, wherein the therapeutically effective amount is equivalent to a dose selected from a group consisting of about 0.5 to about 5 mg/kg, about 0.5 to about 1.0 mg/kg, and about 8-20 mg/kilogram.

18. The method of claim 11, wherein the therapeutically effective amount is equivalent to a dose selected from a group consisting of about 0.1 mg/kg, about 0.5 mg/kg, about 1.0 mg/kg, and about 5 mg/kg.

19. The method of claim 11, wherein the therapeutically effective amount is from about 400 to about 800 mg/day, 60 to about 180 mg/day, or from about 60 to about 120 mg/day.

\* \* \* \* \*

UNITED STATES PATENT AND TRADEMARK OFFICE
CERTIFICATE OF CORRECTION

| | |
|---|---|
| PATENT NO. | : 8,816,047 B2 |
| APPLICATION NO. | : 12/674573 |
| DATED | : August 26, 2014 |
| INVENTOR(S) | : Levetan et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1006 days.

Signed and Sealed this
Fifteenth Day of December, 2015

Michelle K. Lee
*Director of the United States Patent and Trademark Office*

SEQUENCE LISTING

<160> NUMBER OF SEQ ID NOS: 94

<210> SEQ ID NO 1
<211> LENGTH: 528
<212> TYPE: DNA
<213> ORGANISM: Homo sapiens

<400> SEQUENCE: 1

```
atgctgcctc ccatggccct gcccagtgta tcttggatgc tgctttcctg cctcatgctg      60
ctgtctcagg ttcaaggtga agaaccccag agggaactgc cctctgcacg gatccgctgt     120
cccaaaggct ccaaggccta tggctcccac tgctatgcct tgttttgtc accaaaatcc      180
tggacagatg cagatctggc ctgccagaag cggccctctg gaaacctggt gtctgtgctc     240
agtggggctg agggatcctt cgtgtcctcc ctggtgaaga gcattggtaa cagctactca     300
tacgtctgga ttgggctcca tgaccccaca cagggcaccg agcccaatgg agaaggttgg     360
gagtggagta gcagtgatgt gatgaattac tttgcatggg agagaaatcc ctccaccatc     420
tcaagccccg ccactgtgc gagcctgtcg agaagcacag catttctgag gtggaaagat     480
tataactgta atgtgaggtt accctatgtc tgcaagttca ctgactag                  528
```

<210> SEQ ID NO 2
<211> LENGTH: 15
<212> TYPE: PRT
<213> ORGANISM: Homo sapiens

<400> SEQUENCE: 2

Ile Gly Leu His Asp Pro Thr Gln Gly Thr Glu Pro Asn Gly Glu
1               5                   10                  15

<210> SEQ ID NO 3
<211> LENGTH: 15
<212> TYPE: PRT
<213> ORGANISM: Homo sapiens

<400> SEQUENCE: 3

Trp Ile Gly Leu His Asp Pro Thr Gln Gly Thr Glu Pro Asn Gly
1               5                   10                  15

<210> SEQ ID NO 4
<211> LENGTH: 14
<212> TYPE: PRT
<213> ORGANISM: Homo sapiens

<400> SEQUENCE: 4

Ile Gly Leu His Asp Pro Thr Gln Gly Thr Glu Pro Asn Gly
1               5                   10

<210> SEQ ID NO 5
<211> LENGTH: 15
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: AMIDATION
<222> LOCATION: (15)..(15)

<400> SEQUENCE: 5

Ile Gly Leu His Asp Pro Thr Gln Gly Thr Glu Pro Asn Gly Glu
1               5                   10                  15

-continued

```
<210> SEQ ID NO 6
<211> LENGTH: 15
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: AMIDATION
<222> LOCATION: (15)..(15)

<400> SEQUENCE: 6

Trp Ile Gly Leu His Asp Pro Thr Gln Gly Thr Glu Pro Asn Gly
1               5                   10                  15

<210> SEQ ID NO 7
<211> LENGTH: 14
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: AMIDATION
<222> LOCATION: (14)..(14)

<400> SEQUENCE: 7

Ile Gly Leu His Asp Pro Thr Gln Gly Thr Glu Pro Asn Gly
1               5                   10

<210> SEQ ID NO 8
<211> LENGTH: 16
<212> TYPE: PRT
<213> ORGANISM: Homo sapiens

<400> SEQUENCE: 8

Ile Gly Leu His Asp Pro Thr Gln Gly Thr Glu Pro Asn Gly Glu Cys
1               5                   10                  15

<210> SEQ ID NO 9
<211> LENGTH: 16
<212> TYPE: PRT
<213> ORGANISM: Homo sapiens

<400> SEQUENCE: 9

Trp Ile Gly Leu His Asp Pro Thr Gln Gly Thr Glu Pro Asn Gly Cys
1               5                   10                  15

<210> SEQ ID NO 10
<211> LENGTH: 15
<212> TYPE: PRT
<213> ORGANISM: Homo sapiens

<400> SEQUENCE: 10

Ile Gly Leu His Asp Pro Thr Gln Gly Thr Glu Pro Asn Gly Cys
1               5                   10                  15

<210> SEQ ID NO 11
<211> LENGTH: 15
<212> TYPE: PRT
<213> ORGANISM: Homo sapiens
<220> FEATURE:
<221> NAME/KEY: DISULFID
<222> LOCATION: (15)..(15)

<400> SEQUENCE: 11
```

```
Ile Gly Leu His Asp Pro Thr Gln Gly Thr Glu Pro Asn Gly Cys
1               5                   10                  15

<210> SEQ ID NO 12
<211> LENGTH: 17
<212> TYPE: PRT
<213> ORGANISM: Homo sapiens
<220> FEATURE:
<221> NAME/KEY: DISULFID
<222> LOCATION: (17)..(17)

<400> SEQUENCE: 12

Trp Ile Gly Leu His Asp Pro Thr Gln Gly Thr Glu Pro Asn Gly Glu
1               5                   10                  15

Cys

<210> SEQ ID NO 13
<211> LENGTH: 15
<212> TYPE: PRT
<213> ORGANISM: Homo sapiens
<220> FEATURE:
<221> NAME/KEY: DISULFID
<222> LOCATION: (15)..(15)

<400> SEQUENCE: 13

Ile Gly Leu His Asp Pro Thr Gln Gly Thr Glu Pro Asn Gly Cys
1               5                   10                  15

<210> SEQ ID NO 14
<211> LENGTH: 16
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: AMIDATION
<222> LOCATION: (16)..(16)

<400> SEQUENCE: 14

Ile Gly Leu His Asp Pro Thr Gln Gly Thr Glu Pro Asn Gly Glu Cys
1               5                   10                  15

<210> SEQ ID NO 15
<211> LENGTH: 16
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: AMIDATION
<222> LOCATION: (16)..(16)

<400> SEQUENCE: 15

Trp Ile Gly Leu His Asp Pro Thr Gln Gly Thr Glu Pro Asn Gly Cys
1               5                   10                  15

<210> SEQ ID NO 16
<211> LENGTH: 15
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
```

```
<220> FEATURE:
<221> NAME/KEY: AMIDATION
<222> LOCATION: (15)..(15)

<400> SEQUENCE: 16

Ile Gly Leu His Asp Pro Thr Gln Gly Thr Glu Pro Asn Gly Cys
1               5                   10                  15

<210> SEQ ID NO 17
<211> LENGTH: 16
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: DISULFID
<222> LOCATION: (16)..(16)
<220> FEATURE:
<221> NAME/KEY: AMIDATION
<222> LOCATION: (16)..(16)

<400> SEQUENCE: 17

Ile Gly Leu His Asp Pro Thr Gln Gly Thr Glu Pro Asn Gly Glu Cys
1               5                   10                  15

<210> SEQ ID NO 18
<211> LENGTH: 16
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: DISULFID
<222> LOCATION: (16)..(16)
<220> FEATURE:
<221> NAME/KEY: AMIDATION
<222> LOCATION: (16)..(16)

<400> SEQUENCE: 18

Trp Ile Gly Leu His Asp Pro Thr Gln Gly Thr Glu Pro Asn Gly Cys
1               5                   10                  15

<210> SEQ ID NO 19
<211> LENGTH: 15
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: DISULFID
<222> LOCATION: (15)..(15)
<220> FEATURE:
<221> NAME/KEY: AMIDATION
<222> LOCATION: (15)..(15)

<400> SEQUENCE: 19

Ile Gly Leu His Asp Pro Thr Gln Gly Thr Glu Pro Asn Gly Cys
1               5                   10                  15

<210> SEQ ID NO 20
<211> LENGTH: 16
<212> TYPE: PRT
<213> ORGANISM: Homo sapiens
<220> FEATURE:
<221> NAME/KEY: SITE
```

```
<222> LOCATION: (16)..(16)
<223> OTHER INFORMATION: PEGYLATION

<400> SEQUENCE: 20

Ile Gly Leu His Asp Pro Thr Gln Gly Thr Glu Pro Asn Gly Glu Cys
1               5                   10                  15

<210> SEQ ID NO 21
<211> LENGTH: 16
<212> TYPE: PRT
<213> ORGANISM: Homo sapiens
<220> FEATURE:
<221> NAME/KEY: SITE
<222> LOCATION: (16)..(16)
<223> OTHER INFORMATION: PEGYLATION

<400> SEQUENCE: 21

Trp Ile Gly Leu His Asp Pro Thr Gln Gly Thr Glu Pro Asn Gly Cys
1               5                   10                  15

<210> SEQ ID NO 22
<211> LENGTH: 15
<212> TYPE: PRT
<213> ORGANISM: Homo sapiens
<220> FEATURE:
<221> NAME/KEY: SITE
<222> LOCATION: (15)..(15)
<223> OTHER INFORMATION: PEGYLATION

<400> SEQUENCE: 22

Ile Gly Leu His Asp Pro Thr Gln Gly Thr Glu Pro Asn Gly Cys
1               5                   10                  15

<210> SEQ ID NO 23
<211> LENGTH: 16
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: SITE
<222> LOCATION: (16)..(16)
<223> OTHER INFORMATION: PEGYLATION
<220> FEATURE:
<221> NAME/KEY: AMIDATION
<222> LOCATION: (16)..(16)

<400> SEQUENCE: 23

Ile Gly Leu His Asp Pro Thr Gln Gly Thr Glu Pro Asn Gly Glu Cys
1               5                   10                  15

<210> SEQ ID NO 24
<211> LENGTH: 16
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: SITE
<222> LOCATION: (16)..(16)
<223> OTHER INFORMATION: PEGYLATION
<220> FEATURE:
<221> NAME/KEY: AMIDATION
<222> LOCATION: (16)..(16)

<400> SEQUENCE: 24
```

```
Trp Ile Gly Leu His Asp Pro Thr Gln Gly Thr Glu Pro Asn Gly Cys
1               5                   10                  15
```

<210> SEQ ID NO 25
<211> LENGTH: 15
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: SITE
<222> LOCATION: (15)..(15)
<223> OTHER INFORMATION: PEGYLATION
<220> FEATURE:
<221> NAME/KEY: AMIDATION
<222> LOCATION: (15)..(15)

<400> SEQUENCE: 25

```
Ile Gly Leu His Asp Pro Thr Gln Gly Thr Glu Pro Asn Gly Cys
1               5                   10                  15
```

<210> SEQ ID NO 26
<211> LENGTH: 15
<212> TYPE: PRT
<213> ORGANISM: Mesocricetus auratus

<400> SEQUENCE: 26

```
Ile Gly Leu His Asp Pro Ser His Gly Thr Leu Pro Asn Gly Ser
1               5                   10                  15
```

<210> SEQ ID NO 27
<211> LENGTH: 15
<212> TYPE: PRT
<213> ORGANISM: Mesocricetus auratus

<400> SEQUENCE: 27

```
Ile Gly Leu His Asp Pro Ser His Gly Thr Leu Pro Asn Gly Ser
1               5                   10                  15
```

<210> SEQ ID NO 28
<211> LENGTH: 175
<212> TYPE: PRT
<213> ORGANISM: Homo sapiens

<400> SEQUENCE: 28

```
Met Leu Pro Pro Met Ala Leu Pro Ser Val Ser Trp Met Leu Leu Ser
1               5                   10                  15

Cys Leu Ile Leu Leu Cys Gln Val Gln Gly Glu Thr Gln Lys Glu
                20                  25                  30

Leu Pro Ser Pro Arg Ile Ser Cys Pro Lys Gly Ser Lys Ala Tyr Gly
                35                  40                  45

Ser Pro Cys Tyr Ala Leu Phe Leu Ser Pro Lys Ser Trp Met Asp Ala
50                  55                  60

Asp Leu Ala Cys Gln Lys Arg Pro Ser Gly Lys Leu Val Ser Val Leu
65                  70                  75                  80

Ser Gly Ala Glu Gly Ser Phe Val Ser Leu Val Arg Ser Ile Ser
                85                  90                  95

Asn Ser Tyr Ser Tyr Ile Trp Ile Gly Leu His Asp Pro Thr Gln Gly
                100                 105                 110

Ser Glu Pro Asp Gly Asp Gly Trp Glu Trp Ser Ser Thr Asp Val Met
            115                 120                 125
```

```
Asn Tyr Phe Ala Trp Glu Lys Asn Pro Ser Thr Ile Leu Asn Pro Gly
        130                 135                 140

His Cys Gly Ser Leu Ser Arg Ser Thr Gly Phe Leu Lys Trp Lys Asp
145                 150                 155                 160

Tyr Asn Cys Asp Ala Lys Leu Pro Tyr Val Cys Lys Phe Lys Asp
                165                 170                 175

<210> SEQ ID NO 29
<211> LENGTH: 14
<212> TYPE: PRT
<213> ORGANISM: Homo sapiens

<400> SEQUENCE: 29

Ile Gly Leu His Asp Pro Thr Gln Gly Ser Glu Pro Asp Gly
1               5                   10

<210> SEQ ID NO 30
<211> LENGTH: 16
<212> TYPE: PRT
<213> ORGANISM: Homo sapiens

<400> SEQUENCE: 30

Trp Ile Gly Leu His Asp Pro Thr Gln Gly Thr Glu Pro Asn Gly Glu
1               5                   10                  15

<210> SEQ ID NO 31
<211> LENGTH: 16
<212> TYPE: PRT
<213> ORGANISM: Pan troglodytes

<400> SEQUENCE: 31

Trp Ile Gly Leu His Asp Pro Thr Gln Gly Ser Glu Pro Asp Gly Gly
1               5                   10                  15

<210> SEQ ID NO 32
<211> LENGTH: 16
<212> TYPE: PRT
<213> ORGANISM: Mesocricetus auratus

<400> SEQUENCE: 32

Trp Ile Gly Leu His Asp Pro Ser His Gly Thr Leu Pro Asn Gly Ser
1               5                   10                  15

<210> SEQ ID NO 33
<211> LENGTH: 16
<212> TYPE: PRT
<213> ORGANISM: Mus musculus

<400> SEQUENCE: 33

Trp Ile Gly Leu His Asp Pro Thr Met Gly Gln Gln Pro Asn Gly Gly
1               5                   10                  15

<210> SEQ ID NO 34
<211> LENGTH: 16
<212> TYPE: PRT
<213> ORGANISM: Rattus norvegicus

<400> SEQUENCE: 34

Trp Ile Trp Leu His Asp Pro Thr Met Gly Gln Gln Pro Asn Gly Gly
1               5                   10                  15

<210> SEQ ID NO 35
<211> LENGTH: 16
<212> TYPE: PRT
```

<213> ORGANISM: Bos taurus

<400> SEQUENCE: 35

Trp Ile Gly Leu His Asp Pro Thr Glu Gly Ser Glu Pro Asp Ala Gly
1               5                   10                  15

<210> SEQ ID NO 36
<211> LENGTH: 16
<212> TYPE: PRT
<213> ORGANISM: Canis familiaris

<400> SEQUENCE: 36

Trp Met Gly Leu His Asp Pro Thr Glu Gly Tyr Glu Pro Asn Ala Asp
1               5                   10                  15

<210> SEQ ID NO 37
<211> LENGTH: 16
<212> TYPE: PRT
<213> ORGANISM: Ovis aries

<400> SEQUENCE: 37

Trp Ile Gly Leu His Asp Pro Thr Glu Gly Ser Glu Pro Asn Ala Gly
1               5                   10                  15

<210> SEQ ID NO 38
<211> LENGTH: 15
<212> TYPE: PRT
<213> ORGANISM: Pan troglodytes

<400> SEQUENCE: 38

Trp Ile Gly Leu His Asp Pro Thr Gln Gly Ser Glu Pro Asp Gly
1               5                   10                  15

<210> SEQ ID NO 39
<211> LENGTH: 15
<212> TYPE: PRT
<213> ORGANISM: Mesocricetus auratus

<400> SEQUENCE: 39

Trp Ile Gly Leu His Asp Pro Ser His Gly Thr Leu Pro Asn Gly
1               5                   10                  15

<210> SEQ ID NO 40
<211> LENGTH: 15
<212> TYPE: PRT
<213> ORGANISM: Mus musculus

<400> SEQUENCE: 40

Trp Ile Gly Leu His Asp Pro Thr Met Gly Gln Gln Pro Asn Gly
1               5                   10                  15

<210> SEQ ID NO 41
<211> LENGTH: 15
<212> TYPE: PRT
<213> ORGANISM: Rattus norvegicus

<400> SEQUENCE: 41

Trp Ile Trp Leu His Asp Pro Thr Met Gly Gln Gln Pro Asn Gly
1               5                   10                  15

<210> SEQ ID NO 42
<211> LENGTH: 15
<212> TYPE: PRT
<213> ORGANISM: Bos taurus

-continued

<400> SEQUENCE: 42

Trp Ile Gly Leu His Asp Pro Thr Glu Gly Ser Glu Pro Asp Ala
1               5                   10                  15

<210> SEQ ID NO 43
<211> LENGTH: 15
<212> TYPE: PRT
<213> ORGANISM: Canis familiaris

<400> SEQUENCE: 43

Trp Met Gly Leu His Asp Pro Thr Glu Gly Tyr Glu Pro Asn Ala
1               5                   10                  15

<210> SEQ ID NO 44
<211> LENGTH: 15
<212> TYPE: PRT
<213> ORGANISM: Ovis aries

<400> SEQUENCE: 44

Trp Ile Gly Leu His Asp Pro Thr Glu Gly Ser Glu Pro Asn Ala
1               5                   10                  15

<210> SEQ ID NO 45
<211> LENGTH: 14
<212> TYPE: PRT
<213> ORGANISM: Pan troglodytes

<400> SEQUENCE: 45

Ile Gly Leu His Asp Pro Thr Gln Gly Ser Glu Pro Asp Gly
1               5                   10

<210> SEQ ID NO 46
<211> LENGTH: 14
<212> TYPE: PRT
<213> ORGANISM: Mesocricetus auratus

<400> SEQUENCE: 46

Ile Gly Leu His Asp Pro Ser His Gly Thr Leu Pro Asn Gly
1               5                   10

<210> SEQ ID NO 47
<211> LENGTH: 14
<212> TYPE: PRT
<213> ORGANISM: Mus musculus

<400> SEQUENCE: 47

Ile Gly Leu His Asp Pro Thr Met Gly Gln Gln Pro Asn Gly
1               5                   10

<210> SEQ ID NO 48
<211> LENGTH: 14
<212> TYPE: PRT
<213> ORGANISM: Rattus norvegicus

<400> SEQUENCE: 48

Ile Trp Leu His Asp Pro Thr Met Gly Gln Gln Pro Asn Gly
1               5                   10

<210> SEQ ID NO 49
<211> LENGTH: 14
<212> TYPE: PRT
<213> ORGANISM: Bos taurus

<400> SEQUENCE: 49

Ile Gly Leu His Asp Pro Thr Glu Gly Ser Glu Pro Asp Ala
1               5                   10

<210> SEQ ID NO 50
<211> LENGTH: 14
<212> TYPE: PRT
<213> ORGANISM: Canis familiaris

<400> SEQUENCE: 50

Met Gly Leu His Asp Pro Thr Glu Gly Tyr Glu Pro Asn Ala
1               5                   10

<210> SEQ ID NO 51
<211> LENGTH: 14
<212> TYPE: PRT
<213> ORGANISM: Ovis aries

<400> SEQUENCE: 51

Ile Gly Leu His Asp Pro Thr Glu Gly Ser Glu Pro Asn Ala
1               5                   10

<210> SEQ ID NO 52
<211> LENGTH: 15
<212> TYPE: PRT
<213> ORGANISM: Pan troglodytes

<400> SEQUENCE: 52

Ile Gly Leu His Asp Pro Thr Gln Gly Ser Glu Pro Asp Gly Gly
1               5                   10                  15

<210> SEQ ID NO 53
<211> LENGTH: 15
<212> TYPE: PRT
<213> ORGANISM: Mus musculus

<400> SEQUENCE: 53

Ile Gly Leu His Asp Pro Thr Met Gly Gln Gln Pro Asn Gly Gly
1               5                   10                  15

<210> SEQ ID NO 54
<211> LENGTH: 15
<212> TYPE: PRT
<213> ORGANISM: Rattus norvegicus

<400> SEQUENCE: 54

Ile Trp Leu His Asp Pro Thr Met Gly Gln Gln Pro Asn Gly Gly
1               5                   10                  15

<210> SEQ ID NO 55
<211> LENGTH: 14
<212> TYPE: PRT
<213> ORGANISM: Bos taurus

<400> SEQUENCE: 55

Ile Gly Leu His Asp Pro Thr Glu Ser Glu Pro Asp Ala Gly
1               5                   10

<210> SEQ ID NO 56
<211> LENGTH: 15
<212> TYPE: PRT
<213> ORGANISM: Canis familiaris

<400> SEQUENCE: 56

Met Gly Leu His Asp Pro Thr Glu Gly Tyr Glu Pro Asn Ala Asp
1               5                   10                  15

```
<210> SEQ ID NO 57
<211> LENGTH: 15
<212> TYPE: PRT
<213> ORGANISM: Ovis aries

<400> SEQUENCE: 57

Ile Gly Leu His Asp Pro Thr Glu Gly Ser Glu Pro Asn Ala Gly
1               5                   10                  15

<210> SEQ ID NO 58
<211> LENGTH: 15
<212> TYPE: PRT
<213> ORGANISM: Homo sapiens

<400> SEQUENCE: 58

Trp Ile Gly Leu His Asp Pro Thr Gln Gly Ser Glu Pro Asp Gly
1               5                   10                  15

<210> SEQ ID NO 59
<211> LENGTH: 15
<212> TYPE: PRT
<213> ORGANISM: Homo sapiens

<400> SEQUENCE: 59

Ile Gly Leu His Asp Pro Thr Gln Gly Ser Glu Pro Asp Gly Asp
1               5                   10                  15

<210> SEQ ID NO 60
<211> LENGTH: 14
<212> TYPE: PRT
<213> ORGANISM: Pan troglodytes

<400> SEQUENCE: 60

Ile Gly Leu His Asp Pro Thr Gln Gly Ser Glu Pro Asp Gly
1               5                   10

<210> SEQ ID NO 61
<211> LENGTH: 14
<212> TYPE: PRT
<213> ORGANISM: Mesocricetus auratus

<400> SEQUENCE: 61

Ile Gly Leu His Asp Pro Ser His Gly Thr Leu Pro Asn Gly
1               5                   10

<210> SEQ ID NO 62
<211> LENGTH: 14
<212> TYPE: PRT
<213> ORGANISM: Mus musculus

<400> SEQUENCE: 62

Ile Gly Leu His Asp Pro Thr Met Gly Gln Gln Pro Asn Gly
1               5                   10

<210> SEQ ID NO 63
<211> LENGTH: 14
<212> TYPE: PRT
<213> ORGANISM: Rattus norvegicus

<400> SEQUENCE: 63

Ile Trp Leu His Asp Pro Thr Met Gly Gln Gln Pro Asn Gly
1               5                   10
```

```
<210> SEQ ID NO 64
<211> LENGTH: 14
<212> TYPE: PRT
<213> ORGANISM: Bos taurus

<400> SEQUENCE: 64

Ile Gly Leu His Asp Pro Thr Glu Gly Ser Glu Pro Asp Ala
1               5                   10

<210> SEQ ID NO 65
<211> LENGTH: 14
<212> TYPE: PRT
<213> ORGANISM: Canis familiaris

<400> SEQUENCE: 65

Met Gly Leu His Asp Pro Thr Glu Gly Tyr Glu Pro Asn Ala
1               5                   10

<210> SEQ ID NO 66
<211> LENGTH: 14
<212> TYPE: PRT
<213> ORGANISM: Ovis aries

<400> SEQUENCE: 66

Ile Gly Leu His Asp Pro Thr Glu Gly Ser Glu Pro Asn Ala
1               5                   10

<210> SEQ ID NO 67
<211> LENGTH: 14
<212> TYPE: PRT
<213> ORGANISM: Homo sapiens

<400> SEQUENCE: 67

Ile Gly Leu His Asp Pro Lys Lys Asn Arg Arg Trp His Trp
1               5                   10

<210> SEQ ID NO 68
<211> LENGTH: 14
<212> TYPE: PRT
<213> ORGANISM: Homo sapiens

<400> SEQUENCE: 68

Ile Gly Leu His Asp Pro Lys Lys Asn Arg Arg Trp His Trp
1               5                   10

<210> SEQ ID NO 69
<211> LENGTH: 14
<212> TYPE: PRT
<213> ORGANISM: Rattus norvegicus

<400> SEQUENCE: 69

Ile Gly Leu His Asp Pro Lys Asn Asn Arg Arg Trp His Trp
1               5                   10

<210> SEQ ID NO 70
<211> LENGTH: 14
<212> TYPE: PRT
<213> ORGANISM: Mus musculus

<400> SEQUENCE: 70

Thr Gly Leu His Asp Pro Lys Arg Asn Arg Arg Trp His Trp
1               5                   10

<210> SEQ ID NO 71
<211> LENGTH: 14
```

```
<212> TYPE: PRT
<213> ORGANISM: Mus musculus

<400> SEQUENCE: 71

Thr Gly Leu His Asp Pro Lys Ser Asn Arg Arg Trp His Trp
1               5                   10

<210> SEQ ID NO 72
<211> LENGTH: 14
<212> TYPE: PRT
<213> ORGANISM: Mesocricetus auratus

<400> SEQUENCE: 72

Ile Gly Leu His Asp Pro Lys Asn Asn Arg Arg Trp His Trp
1               5                   10

<210> SEQ ID NO 73
<211> LENGTH: 14
<212> TYPE: PRT
<213> ORGANISM: Rattus norvegicus

<400> SEQUENCE: 73

Ile Trp Leu His Asp Pro Thr Met Gly Gln Gln Pro Asn Gly
1               5                   10

<210> SEQ ID NO 74
<211> LENGTH: 14
<212> TYPE: PRT
<213> ORGANISM: Rattus norvegicus

<400> SEQUENCE: 74

Ile Gly Leu His Asp Pro Thr Leu Gly Gly Glu Pro Asn Gly
1               5                   10

<210> SEQ ID NO 75
<211> LENGTH: 14
<212> TYPE: PRT
<213> ORGANISM: Rattus norvegicus

<400> SEQUENCE: 75

Ile Gly Leu His Asp Pro Thr Leu Gly Gln Glu Pro Asn Arg
1               5                   10

<210> SEQ ID NO 76
<211> LENGTH: 14
<212> TYPE: PRT
<213> ORGANISM: Mus musculus

<400> SEQUENCE: 76

Ile Gly Leu His Asp Pro Thr Met Gly Gln Gln Pro Asn Gly
1               5                   10

<210> SEQ ID NO 77
<211> LENGTH: 14
<212> TYPE: PRT
<213> ORGANISM: Mus musculus

<400> SEQUENCE: 77

Ile Gly Leu His Asp Pro Thr Leu Gly Ala Glu Pro Asn Gly
1               5                   10

<210> SEQ ID NO 78
<211> LENGTH: 14
<212> TYPE: PRT
<213> ORGANISM: Mus musculus
```

<400> SEQUENCE: 78

Ile Gly Leu His Asp Pro Thr Leu Gly Tyr Glu Pro Asn Arg
1               5                   10

<210> SEQ ID NO 79
<211> LENGTH: 14
<212> TYPE: PRT
<213> ORGANISM: Rattus norvegicus

<400> SEQUENCE: 79

Ile Gly Leu His Asp Pro Thr Leu Gly Gln Glu Pro Asn Arg
1               5                   10

<210> SEQ ID NO 80
<211> LENGTH: 14
<212> TYPE: PRT
<213> ORGANISM: Mesocricetus auratus

<400> SEQUENCE: 80

Ile Gly Leu His Asp Pro Thr Leu Gly Gln Glu Pro Asn Gly
1               5                   10

<210> SEQ ID NO 81
<211> LENGTH: 14
<212> TYPE: PRT
<213> ORGANISM: Homo sapiens

<400> SEQUENCE: 81

Ile Gly Leu His Asp Pro Thr Gln Gly Ser Glu Pro Asp Gly
1               5                   10

<210> SEQ ID NO 82
<211> LENGTH: 14
<212> TYPE: PRT
<213> ORGANISM: Mus musculus

<400> SEQUENCE: 82

Ile Gly Leu His Asp Leu Ser Leu Gly Ser Leu Pro Asn Glu
1               5                   10

<210> SEQ ID NO 83
<211> LENGTH: 14
<212> TYPE: PRT
<213> ORGANISM: Bos taurus

<400> SEQUENCE: 83

Ile Gly Leu His Asp Pro Thr Glu Gly Ser Glu Ala Asn Ala
1               5                   10

<210> SEQ ID NO 84
<211> LENGTH: 14
<212> TYPE: PRT
<213> ORGANISM: Mesocricetus auratus

<400> SEQUENCE: 84

Ile Gly Leu His Asp Pro Ser His Gly Thr Leu Pro Asn Gly
1               5                   10

<210> SEQ ID NO 85
<211> LENGTH: 14
<212> TYPE: PRT
<213> ORGANISM: Homo sapiens

<400> SEQUENCE: 85

Ile Gly Leu His Asp Pro Gln Lys Arg Gln Gln Trp Gln Trp
1               5                   10

<210> SEQ ID NO 86
<211> LENGTH: 14
<212> TYPE: PRT
<213> ORGANISM: Mus musculus

<400> SEQUENCE: 86

Ile Gly Leu His Asp Pro Gln Lys Lys Gln Leu Trp Gln Trp
1               5                   10

<210> SEQ ID NO 87
<211> LENGTH: 14
<212> TYPE: PRT
<213> ORGANISM: Pan troglodytes

<400> SEQUENCE: 87

Ile Gly Leu His Asp Pro Thr Gln Gly Ser Glu Pro Asp Gly
1               5                   10

<210> SEQ ID NO 88
<211> LENGTH: 14
<212> TYPE: PRT
<213> ORGANISM: Bos taurus

<400> SEQUENCE: 88

Ile Gly Leu His Asp Pro Thr Glu Gly Ser Glu Pro Asp Ala
1               5                   10

<210> SEQ ID NO 89
<211> LENGTH: 14
<212> TYPE: PRT
<213> ORGANISM: Canis familiaris

<400> SEQUENCE: 89

Met Gly Leu His Asp Pro Thr Glu Gly Tyr Glu Pro Asn Ala
1               5                   10

<210> SEQ ID NO 90
<211> LENGTH: 14
<212> TYPE: PRT
<213> ORGANISM: Ovis aries

<400> SEQUENCE: 90

Ile Gly Leu His Asp Pro Thr Glu Gly Ser Glu Pro Asn Ala
1               5                   10

<210> SEQ ID NO 91
<211> LENGTH: 14
<212> TYPE: PRT
<213> ORGANISM: Homo sapiens
<220> FEATURE:
<221> NAME/KEY: SITE
<222> LOCATION: (1)..(1)
<223> OTHER INFORMATION: PEGYLATION

<400> SEQUENCE: 91

Ile Gly Leu His Asp Pro Thr Gln Gly Thr Glu Pro Asn Gly
1               5                   10

<210> SEQ ID NO 92
<211> LENGTH: 13
<212> TYPE: PRT
<213> ORGANISM: Homo sapiens

```
<400> SEQUENCE: 92

Gly Leu His Asp Pro Thr Gln Gly Thr Glu Pro Asn Gly
1               5                   10

<210> SEQ ID NO 93
<211> LENGTH: 11
<212> TYPE: PRT
<213> ORGANISM: Homo sapiens

<400> SEQUENCE: 93

His Asp Pro Thr Gln Gly Thr Glu Pro Asn Gly
1               5                   10

<210> SEQ ID NO 94
<211> LENGTH: 15
<212> TYPE: PRT
<213> ORGANISM: Homo sapiens
<220> FEATURE:
<221> NAME/KEY: SITE
<222> LOCATION: (1)..(1)
<223> OTHER INFORMATION: ACYLATION
<220> FEATURE:
<221> NAME/KEY: AMIDATION
<222> LOCATION: (15)..(15)
<220> FEATURE:
<221> NAME/KEY: SITE
<222> LOCATION: (15)..(15)
<223> OTHER INFORMATION: CYSTEINE ADDUCT

<400> SEQUENCE: 94

Ile Gly His Asp Pro Thr Gln Gly Thr Glu Pro Asn Gly Cys Cys
1               5                   10                  15
```